US006737052B1

(12) United States Patent
Goodrich et al.

(10) Patent No.: US 6,737,052 B1
(45) Date of Patent: May 18, 2004

(54) INDUCTION OF PROGRAMMED CELL DEATH BY N5 GENE

(75) Inventors: David W. Goodrich, Sugar Land, TX (US); Jaleh Doostzadeh, Fremont, CA (US); Shenmin Yin, Houston, TX (US)

(73) Assignee: Board of Regents, University of Texas System, Austin, TX (US)

( * ) Notice: Subject to any disclaimer, the term of this patent is extended or adjusted under 35 U.S.C. 154(b) by 0 days.

(21) Appl. No.: 09/653,465

(22) Filed: Aug. 31, 2000

(65) Prior Publication Data (65)

Related U.S. Application Data
(60) Provisional application No. 60/151,687, filed on Aug. 31, 1999.

(51) Int. Cl.[7] .......................... A01N 63/00; A61K 48/00
(52) U.S. Cl. .................. 424/93.2; 424/93.21; 424/93.6; 435/320.1; 435/455; 435/456
(58) Field of Search .............................. 435/320.1, 455, 435/456; 536/23.1; 514/44; 424/93.2, 93.21, 93.6

(56) References Cited

U.S. PATENT DOCUMENTS 5,654,145 A * 8/1997 Fukuda .......................... 435/6

FOREIGN PATENT DOCUMENTS

WO      WO 96/31603     10/1996

OTHER PUBLICATIONS

IM Verma et al., Nature, "Gene therapy–promises, problems and prospects," Sep. 1997, vol. 389, pp. 239–2242.*
WF Anderson, Nature, "Human gene therapy," Apr. 1998, vol. 392, pp. 25–30.*
Durfee et al., The amino–terminal region of the retinoblastoma gene product binds a novel nuclear matrix protein that co–localizes to centers for RNA processing, 1994, The Journal of Cell Biology, vol. 127, pp. 609–622.*
Ngo et al., Computational complexity, protein structure prediction, and the levinthal paradox, 1994, The Protein Folding Problem and Tertiary Structure Position, pp. 491–494.*
Chiu et al., Optimizing energy potentials for success in protein tertiary structure prediction, 1998, Folding & Design, vol. 3, pp. 223–228.*
Vile et al., cancer gene therapy: hard lessons and new courses, 2000, Gene Therapy, vol. 7, pp. 2–8.*
Gomez–Navarro et al., Gene therapy for cancer, 1999, European Journal of Cancer, vol. 35, pp. 867–885.*
Feinstein et al., The death domain: a module shared by proteins with diverse cellular functions, 1995, TIBS 20, pp. 342–344.*

Boldin et al., "Self–association of the 'Death Domains' of the p55 Tumor Necrosis Factor (TNF) Receptor and Fas/APO1 Prompts Signaling for TNF and Fas/APO1 Effects," *J. Biol. Chem.*270(1):387–391, 1995.
Bookstein et al., "Promoter deletion and loss retinoblastoma gene expression in human prostate carcinoma," *Proc. Nat'l Acad. Sci. U S A.*87:7762–7766, 1990.
Chandar et al., "Inactivation of p53 gene in human and murine osteosarcoma cells," *Br. J. Cancer,* 65: 208–214, 1992.
Chen et al., "Phosphorylation of the retinoblastoma gene product is modulated during the cell cycle and cellular differentiation," Cell, 58:1193–1198, 1989.
Connell–Crowley et al., "Cyclin D1/Cdk4 regulates retinoblastoma protein–mediated cell cycle arrest by site–specific phosphorylation," *Mol. Biol. Cell,* 8: 287–301, 1997.
Doostzadeh–Cizeron and Goodrich, "The Nuclear Death Domain Protein p84N5 Activates a $G_2$/M Cell Cycle Checkpoint Prior ot the Onset of Apoptosis," *J.Biol.Chem.,* 267(2):1127–1132, 2001.
Dryja et al., "Molecular etiology of low–penetrance retinoblastoma in two pedigrees," *Am. J. Hum. Genet.,* 52:1122–1128, 1993.
Goodrich and Lee, "Molecular characterization of the retinoblastoma susceptibility gene," *Biochim. Biophys. Acta.,* 1155:43–61, 1993.
Goodrich et al., "The retinoblastoma gene product regulates progression through the G1 phase of the cell cycle," *Cell,* 67: 293–302, 1991.
Haas–Kogan et al., "Inhibition of apoptosis by the retinoblastoma gene product," *EMBO J.,* 14:461–472, 1995.
Inoue et al., "70–kDa heat shock cognate protein interacts directly with the N–terminal region of the retinoblastoma gene product pRb. Identification of a novel region of pRb–-mediating protein intraction," *J. Biol. Chem.*270(38): 22571–22576, 1995.
Itoh et al., "A Novel Protein Domain Required for Apoptosis," *J. Biol. Chem.*268(15):10932–10937, 1993.
Letsou et al., "Genetic and molecular characterization of tube, a Drosophila gene maternally required for embryonic dorsoventral polarity," *Proc. Nat'l Acad. Sci. USA*88:810–814, 1991.
Park and Baichwal, "Systematic mutational analysis of the death domain of the tumor necrosis factor receptor 1–associated protein TRADD," *J.Biol.Chem.* 271, 9858–9862, 1996.

(List continued on next page.)

Primary Examiner—Scott D. Priebe
Assistant Examiner—Brian Whiteman
(74) Attorney, Agent, or Firm—Fulbright & Jaworski L.L.P.

(57) ABSTRACT

The present invention concerns methods and compositions for treating cancer in a subject. These methods and compositions utilize the activities associated with the N5 gene product, p84N5. p84N5 contains a functional death domain, can interact with the retinoblastoma gene product and is normally localized to the nucleus of cells. Increasing the activity level of p84N5 in cancer cells is beneficial for the treatment of cancer.

17 Claims, 29 Drawing Sheets

OTHER PUBLICATIONS

Riley et al., "Mutations of N–terminal regions render the retinoblastoma protein insufficient for functions in development and tumor suppression," *Mol. Cell. Biol.*17(12):7342–7352, 1997.

Shelton and Wasserman,"*pelle* Encodes a Protein Kinase Required to Establish Dorsoventral Polarity in the Drosophila Embryo," *Cell*72: 515–525, 1993.

Sterner et al., "Negative regulation DNA replication by the retinoblastoma protein is mediated by its association with MBM7" *Mol. Cell. Biol.*18(5): 2748–2757, 1998.

Sterner et al., "The amino terminus of the retinoblastoma (Rb) protein associates with a cyclin–dependent kinase–like kinase via Rb amino acids required for growth suppression," *Cell Growth Differ.* 7, 53–64, 1996.

Tartaglia et al., "A novel domain within the 55 kd TNF receptor signals cell death," *Cell*74:845–853, 1993.

Vaishnaw et al., "The molecular basis for apoptotic defects in patients with CD95 (Fas/Apo–1) mutations," *J.Clin.Invest.*103(3):355–363, 1999.

Wang et al., "Rb functions to inhibit apoptosis during myocyte differentiation," *Cancer Res.,*57:351–354, 1997.

Wang, "Retinoblastoma protein in growth suppression and death protection," *Curr. Opin. Genet. Dev.,*7:39–45, 1997.

Wiegmann et al., "Functional Dichotomy of Neutral and Acidic Sphingomyelinases in Tumor Necrosis Factor Signaling," *Cell*78:1005–1015, 1994.

Yin et al., "Adenovirus–mediated N5 gene transfer inhibits tumor cell proliferation by induction of apoptosis," *Cancer Gene Therapy,*7(7):985–990, 2000.

* cited by examiner

INDUCTION OF PROGRAMMED CELL DEATH BY N5 GENE

The present application claims the priority of co-pending U.S. Provisional Patent Application Serial No. 60/151,687, filed Aug. 31, 1999, the entire disclosure of which is incorporated herein by reference without disclaimer.

The government owns rights in the present invention pursuant to grant numbers CA-70292-01 and CA-16672 from the National Institutes of Health.

BACKGROUND OF THE INVENTION

1. Field of the Invention

The present invention relates generally to the fields of cancer and biochemistry. More particularly, it concerns induction of programmed cell death or apoptosis in tumor cells by the p84N5 gene.

2. Description of Related Art

Coordination of cell proliferation and cell death is required for normal development and tissue homeostasis in multicellular organisms. A defect in the normal coordination of these two processes is a fundamental requirement for tumorigenesis. Progression through the cell cycle is highly regulated, requiring the transit of numerous checkpoints (for review, see Hunter, 1993). The extent of cell death is physiologically controlled by activation of a programmed suicide pathway that results in a morphologically recognizable form of death termed apoptosis (Jacobson et al., 1997; Vaux et al., 1994). Both extra-cellular signals, such as tumor necrosis factor, and intracellular signals, like p53, can induce apoptotic cell death. Although many proteins involved in apoptosis or the cell cycle have been identified, the mechanisms by which these two processes are coordinated are not well understood.

Mutation of the retinoblastoma tumor suppressor gene (Rb) alone is sufficient to cause retinoblastoma in humans, suggesting it might play a role in the normal coordination of cell proliferation and cell death (Goodrich and Lee, 1993). The retinoblastoma tumor suppressor protein (p110Rb) can inhibit progression through the G1 phase of the cell cycle (Goodrich et al., 1991). This is accomplished largely by modulation of cellular transcription factors, like E2F1, through direct physical association (Bagchi et al., 1991; Flemington et al., 1993; Kaelin, Jr. et al., 1992; Weintraub et al., 1992). Cyclin-dependent kinase phosphorylation of Rb protein (p110Rb) allows transit through the Rb-enforced checkpoint (Connell-Crowley et al., 1997) by disrupting physical association with these cellular proteins. Several lines of evidence suggest that p110Rb may also regulate apoptosis. Ectopic expression of p110Rb inhibits apoptosis triggered by radiation (Haas-Kogan et al., 1995), E2F1 (Hsieh et al., 1997), p53 (Haupt et al., 1995), myocyte differentiation (Wang et al., 1997), or ceramide (McConkey et al., 1996). Rb protein also is a target for cleavage by caspases during apoptosis (Janicke et al., 1996; An and Dou, 1996). Finally, mouse embryos lacking functional Rb have inappropriately high levels of apoptosis in the central nervous system, the liver, the eye lens, and skeletal muscle (Zacksenhaus et al., 1996). Although these findings suggest that p110Rb may regulate apoptosis, it is unclear whether this regulation is a novel function, or an indirect consequence of Rb-mediated effects on the cell cycle.

The C-terminal half of p110Rb is sufficient for many of its known molecular activities, including modulation of transcription factor function and induction of cell cycle arrest. The purpose of the N-terminal half of p110Rb is undefined. Several observations suggest that this region may be important for normal function. First, some mutations causing low penetrance retinoblastoma specifically alter the N-terminal half of the protein (Dryja et al., 1993; Hogg et al., 1993; Lohmann et al., 1994). Second, the amino acid sequence of the N-terminal half of p110Rb is conserved between mouse, rat, chicken, frog, newt, and human. Finally, N-terminally truncated Rb transgenes are incapable of rescuing developmental defects observed in mice deficient in wild-type Rb (Riley et al., 1997).

The N5 gene was isolated based on its ability to encode a protein that specifically associates with the N-terminal half of p110Rb (Durfee et al., 1994b). Three other proteins, a 70 kDa heat shock protein (Inoue et al., 1995), a kinase (Sterner et al., 1996), and MCM7 (Sterner et al., 1998), have been discovered to bind the N-terminal half of p110Rb. The relevance of these interactions for Rb function is not completely understood, although association of p110Rb with MCM7 does inhibit DNA replication in vitro (Sterner et al., 1998). The N5 protein (p84N5) normally is localized exclusively to the nucleus during interphase and has a region of structural similarity to the death domains of several well-characterized proteins involved in apoptosis, including tumor necrosis factor receptor 1 (TNFR-1) (Feinstein et al., 1995).

Rb gene-associated tumors, including retinoblastomas, small cell lung-carcinoma, osteosarcoma, bladder carcinoma, prostate carcinoma and breast cancer, are a difficult class of tumors to treat. Current therapies are not specific for these tumors and have serious treatment-associated side effects. There exists a need for a treatment that is specific for tumor cells that does not have side effects and specifically targets Rb gene associated tumors.

SUMMARY OF THE INVENTION

The present invention concerns methods and compositions for treating cancer in a subject. These methods and compositions utilize the activities associated with the N5 gene product, p84N5. p84N5 contains a functional death domain, can interact with the retinoblastoma gene product, and is normally localized to the nucleus of cells. Increasing the activity level of p84N5 in cancer cells is, therefor, beneficial for the treatment of cancer.

Claimed in the present invention is a viral composition comprising a recombinant viral vector encoding a p84N5 death domain. In other embodiments, the p84N5 death domain may be fused to other protein sequences. Alternatively, the p84N5 may be as shown in SEQ ID NO:1. In preferred embodiments, the recombinant viral vector is an adenoviral, adeno-associated viral, retroviral, herpes viral, papilloma viral, or hepatitis B viral vector.

Also claimed in the present invention is a protein composition comprising purified p84N5 protein. Purified p84N5 contains the p84N5 death domain and the p84N5 protein or portion of said p84N5 protein including a death domain may be fused to a second protein. In preferred embodiments, the p84N5 protein is as shown in SEQ ID NO:2.

Also claimed in the present invention is a recombinant cell exhibiting lower amounts of p84N5 activity when compared to the starting, non-engineered cell, comprising an alteration in transcription, translation, messenger RNA or protein stability, or protein half-life of endogenous p84N5. Alternatively, a recombinant cell exhibiting increased amounts of p84N5 activity when compared to the starting, non-engineered cell, comprising an alteration in transcription, translation, messenger RNA or protein stability, or protein half-life of endogenous p84N5 is claimed. Such cells exhibiting lower or increased amounts of p84N5 activity may be cell lines or cells in transgenic animals.

A method of treating cancer in a subject, comprising contacting said subject with a recombinant vector encoding a p84N5 death domain operably linked to a promoter that functions in said cell. In preferred embodiments, the p84N5 death domain is as shown in SEQ ID NO:1. In preferred embodiments, the recombinant vector encoding a p84N5 death domain is a viral vector. The viral vector may be an adenovirus, adeno-associated virus, retrovirus, herpes virus, papilloma virus, or hepatitus B virus. In preferred embodiments the virus is an adenovirus and is administered to the subject at a dose of about $10^{10}$ to about $10^{12}$ pfu.

Also claimed in the present invention are methods of treating a subject with cancer with a protein composition comprising purified p84N5. p84N5 may be purified from natural sources or may be recombinant p84N5 produced by a number of means.

Treating cancer is defined as inducing apoptosis, inhibiting cell division, inhibiting metastatic potential, reducing tumor burden, increasing sensitivity to chemotherapy or radiotherapy, killing a cancer cell, inhibiting the growth of a cancer cell, or inducing tumor regression in a subject. In preferred embodiments, the subject is human. The cancer to be treated may be retinoblastoma negative.

In preferred embodiments, treatment of the subject will include a second agent, such as a therapeutic polypeptide, nucleic acid encoding a therapeutic polypeptide, a chemotherapeutic agent, or a radiotherapeutic agent. The second agent may be administered at a different time than the p84N5 treatment. In some embodiments, the second agent may be a nucleic acid encoding p53. Subjects may be treated by intravenous, intraperitoneal, intradermal, intratumoral, intramuscularoral, dermal, nasal, buccal, rectal, vaginal, inhalation, or topical administration of the p84N5 treatment.

The present invention provides the first report that identifies p84N5 as a death domain-containing protein that triggers apoptotic cell death from within the nucleus. Few proteins, other than transcription factors, are known that require nuclear localization to induce apoptosis.

The invention also provides novel mechanisms that transduce nuclear apoptotic signals. The inventors envision that these mechanisms will enable the prediction of tumor responses to genotoxic radiation and/or chemotherapy thereby providing methods for cancer prognosis and new anticancer treatments. Thus, p84N5 induces an ATM-independent, caffeine-sensitive G2/M cell cycle arrest prior to the onset of apoptosis. Furthermore, p84N5-induced apoptosis is preceded by activation of a p53-independent G2/M checkpoint.

The invention also describes identification of the N5 nuclear localization signal and shows that nuclear localization is required to inhibit the clonogenicity of N5 expressing cells. Thus, p84N5 is involved in a Rb-regulated apoptotic pathway that is normally triggered from within the nucleus in response to stimuli, for example, in response to DNA damage. In other studies carried out herein, the inventors have also shown that coexpression of RB can inhibit N5-induced apoptosis, and that their physical association mediates this block.

The inventors have also determined that N5-induced apoptosis is initially accompanied by activation of caspase-6. Activation of caspases-3 and -9 peaks 3 days after the peak of caspase-6 activity. Expression of p84N5 also leads to activation of NF-kB as indicated by nuclear translocation of p65RelA and transcriptional activation of a NF-kB-dependent reporter promoter. Changes are also seen in the relative expression level of Bcl-2 family proteins, including Bak and Bcl-Xs, during p84N5-induced apoptosis. The inventors also demonstrate that p84N5-induced apoptosis does not require p53 and is not inhibited by p53 coexpression.

In another aspect, the inventors demonstrate that expression of p84N5, either by transfection or adenovirus-mediated gene transfer, renders cells inviable. For example, N5 adenovirus infection significantly reduced the proliferation and tumorigenicity of breast, ovarian, and osteosarcoma tumor cell lines. Loss of viability is due to induction of apoptosis. p84N5-expressing cells exhibit many of the typical characteristics of apoptosis, including fragmentation of DNA, exposure of phosphatidylserine on the outer leaflet of the plasma membrane, changes in membrane permeability, and changes in cellular and nuclear morphology. The induction of apoptosis reduced proliferation and tumorigenicity the cancer cells. Thus, N5 encoding nucleic acids provide tools for gene therapy of cancer.

The inventors also demonstrate that co-infection of cancer cells with adenovirus encoding N5 and p53 are highly effective in inducing apoptosis. For example, co-infection of Colo357 X cells with both AdN5 and Adp53 causes a more dramatic reduction growth than infection with either one alone. The invention also explains the mechanism of co-infection as follows; N5 and p53 function in different pathways, N5-induced apoptosis is preceded by a G2/M cell cycle arrest while expression of p53 typically induces a G1 cell cycle arrest. Thus, the invention also provides for anticancer genetherapy using both AdN5 and Adp53.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. SAOS-2 cells were transfected with pCMVN5 (panels b and d) or pCMV (panels a and c). After 16 (panels a and b) or 40 (panels c and d) hours of transfection, cells were photographed under phase contrast at 100×. FIG. 1B. Attached and detached cells transfected as above were collected at the indicated times and stained with trypan blue. Greater than 95% of attached cells were viable and greater than 95% of detached cells were non-viable. The mean number of total viable or non-viable cells present from 3 experiments is indicated. FIG. 1C. The indicated cells were transfecated with pCMVN5 (p84N5) or pCMV (Vector) plus pEGFP-C1 as indicated. Cells were grown in the presence of G418 for two weeks, at which time the number of GFP positive colonies of greater than 20 cells were counted in at least 30 randomly selected 100× fields of view under fluorescent microscopy. Results are expressed as the mean colonies per 100× field of three independent experiments. FIG. 1D. 293 cells were transfected with pCMV or pCMVN5 as shown. Extracts were prepared 24 hours later and equal amounts of total protein were analyzed by western blotting for the protein indicated on the right. The position of molecular weight standards is shown on the left.

FIG. 2A. SAOS-2 cells were cotransfected with pCMVβ-Gal and pCMV (a) or pCMVN5 (b), fixed 24 hours later, and stained with X-Gal. Cells were photographed under phase contrast microscopy at 400×. FIG. 2B. 5637 (lanes 1–3) or SAOS-2 (lanes 4–6) cells were transfected with pCMV (lanes 1,4), pCMVN5 (lanes 3,6), or treated with staurosporine (lanes 2,5). Fragmented DNA was extracted 24 hours later, resolved by agarose gel electrophoresis, and stained with EtBr. Transfection efficiency was approximately 10% for both cell lines. DNA markers are indicated at left. FIG. 2C. SAOS-2 cells were transfected with the indicated expression vectors and apoptosis was measured 24 hours later by TUNEL assay and flow cytometry. The percentage of cells containing fragmented DNA is presented as the mean of three independent experiments. Maximum transfection efficiency under the conditions used was 10%, indicating that nearly all pCMVN5 transfected cells contained fragmented DNA.

FIG. 3A. Top of FIG. indicates sequence identities (shaded boxes) between helix 4 and 5 of the death domains from the indicated proteins which correspond to SEQ ID NO: 6, SEQ ID NO: 7 & SEQ ID NO: 8 respectively. The bar underneath the sequence identifies the extent of the deletion in N5Δα4. The asterisks indicate the positions of point mutations in N5-PP and N5-R. The numbers indicate the corresponding p84N5 amino acids. SAOS-2 or 293 cells were transfected with the indicated plasmids and clonogenicity of transfected cells determined as in FIG. 1C. The results are expressed as the mean of at least 3 experiments. FIG. 3B. 293 cells were transfected with pCMV (lane 1), pCMVN5 (lane 2), pCMVN5Δα4 (lane 3), pCMVN5-PP (lane 4), and pCMVN5-R (lane 5). Extracts were prepared from transfected cells and expression of p84N5 protein analyzed by western blotting with anti-N5 monoclonal antibody 5E10 as indicated in experimental procedures.

FIG. 5A. SAOS-2 cells were treated with the indicated dose of ionizing radiation or staurosporine (S). Attached or detached cells were harvested separately 72 (irradiated) or 12 (staurosporine) hours later and p84N5 expression analyzed in each sample by western blotting as in FIG. 1D. The positions of p84N5, β-actin, or a 64 kDa molecular weight standard are indicated on the left. FIG. 5B. SAOS-2 cells were irradiated with the indicated dose of γ-radiation. Three days later, cells were processed for immunofluorescent staining using the α-N5 5E10 monoclonal antibody as described in the experimental procedures. Cells were photographed at 630×. The arrows indicate two examples of cytoplasmic N5 staining in cells with pyknotic nuclear morphology. Note the more homogeneous α-N5 staining in the irradiated sample.

FIG. 6A. SAOS-2 cells were injected with purified GST (panel a) or GSTN5 (panel b). Ninety minutes later, Hoechst dye was added to the media for 10 minutes prior to photography under fluorescence microscopy at 100×. All cells within the field of view have been injected. FIG. 6B. Cells were injected and analyzed as above with the indicated proteins. The percentage of injected cells with apoptotic morphology and bright Hoechst staining was then counted. The results are the mean of at least 3 experiments. FIG. 6C. Five μl aliquots of GST (lane 1), GSTN5 (lane 2), p110Rb (lane 3), or p56Rb (lane 4) used for microinjection were resolved by SDS-PAGE and stained with coomassie blue. The position of molecular weight standards is indicated at the right. FIG. 6D. SAOS-2 cells were transfected with the indicated expression plasmids and analyzed for apoptosis by TUNEL and flow cytometry as in FIG. 2C. The percentage of cells containing fragmented DNA is shown as the mean of 3 experiments. The maximum transfection efficiency under the conditions used was approximately 10%, indicating that most of the N5 transfected cells contained fragmented DNA.

FIG. 8F. The level of expression of p84N5 after treatment was determined by western blotting. SKOV3 IP-1 cells (lanes 1–4) were treated at an MOI of 50 while U2OS cells (lanes 5–9) were treated at an MOI of 10. Cells were extracted before infection (lanes 1 and 5), 24 hours after infection with AdGFP (lanes 2 and 6) or AdN5 (lanes 3 and 7), 48 hours after infection with AdN5 (lanes 4 and 8), or 72 hours after infection with AdN5 (lane 9). Identical blots were also probed with anti α-actin antibody to control for protein loading (bottom panel). The position of molecular weight standards and the position of α-actin are indicated.

FIG. 10A. SKOV3 IP-1 cells were treated with PBS, AdGFP, or AdN5 at an MOI of 50. Infected cells were subcutaneously injected into the flanks of nude mice and tumor volumes measured weekly thereafter. The data presented represent the mean of at least six mice for each treatment. FIG. 10B. At five weeks post-injection, mice were sacrificed and three representative mice photographed. The left flanks were injected with AdN5 treated cells while the right flanks were injected with AdGFP infected cells. All six mice injected with AdN5 treated cells were tumor free for the entire five weeks of the study.

FIG. 11A. SAOS-2 or FIG. 11B. C33-A cells were infected with the indicated adenovirus and then fixed and processed for PI staining and flow cytometry at the indicated times. Histograms of cell number versus PI staining intensity were generated by flow cytometric analysis of at least 10,000 cells and the cell cycle profiles calculated as described in experimental procedures. The data show the cell cycle profiles of a representative experiment repeated at least three times. FIG. 11C. Protein from SAOS-2 cells infected with the indicated virus was extracted two days post-infection and analyzed for p84N5 or β-actin by western blotting. The positions of molecular weight standards are shown at left. The position of the p84N5 and β-actin bands are shown at right.

FIG. 15A. SAOS-2 cells were transfected with the indicated expression plasmid and nuclear localization of the resulting GFPN5 fusion protein determined under fluorescence microscopy. The schematic indicates the p84N5 amino acids included within each plasmid as well as the position of the p84N5 death domain. FIG. 15B. Photomicrographs of representative cells analyzed as in A. The cells were photographed as in experimental procedures under 630× fold magnification using a fluorescein isothiocyanate filter. FIG. 15C Total cell protein extracted from 293 cells transfected with each of the indicated plasmid constructs was analyzed by western blotting using an anti-GFP antibody. The position of molecular weight standards is indicated on the left. The relative molecular mass of the different GFPN5 fusion proteins is consistent with their predicted mass.

FIG. 16A. SAOS-2 cells were transfected with the indicated expression plasmid and nuclear localization of the resulting GFPN5 fusion protein determined under fluorescence microscopy. The schematic indicates the amino acid sequence of the putative bipartite p84N5 NLS as well as the amino acids contained in the mutant derivatives and the amino acid sequences are represented by SEQ ID NO: 9 for GFPN5, SEQ ID NO: 10 for GFPN5hNLS, and SEQ ID NO: 11 for GFPN5NES. FIG. 16B. Photomicrographs of representative cells analyzed as in A. The cells were photographed as in experimental procedures under 630× fold magnification using a fluorescein isothiocyanate filter. FIG. 16C. Total cell protein extracted from 293 cells transfected with each of the indicated plasmid constructs was analyzed by western blotting using an anti-GFP antibody. The position of molecular weight standards is indicated on the left. In the lower panel, the blot was stripped and re-probed with an antibody directed against β-actin to serve as a protein loading control.

FIG. 18B. SAOS-2 cells were infected at an m.o.i. of 10 with the indicated virus and 72 h later harvested and assayed for fragmented DNA by TUNEL. The percentage of TUNEL-positive cells was determined by flow cytometry. The data presented are the mean of three infections for each virus. FIG. 18C. C-33A cells were infected with the indicated virus at m.o.i. of 10 and harvested 2 days later for annexin V staining. The percentage of annexin V-positive cells was determined by flow cytrometry. The data are the mean of three infections. FIG. 18D. Hoechst 33342 was added to the culture media 3 days following infection of SAOS-2 cells with the indicated virus (10 m.o.i.). The cells were photographed at 1003 under a fluorescent microscope with a UV filter. The results are representative of multiple experiments. FIG. 18E. Extracts prepared from SAOS-2 infected with the indicated virus were analyzed by Western blotting. Blots were stained with monoclonal antibody directed against p84N5. Staining with anti-β-actin served as a protein loading control. The position of molecular weight markers is shown at left for the p84N5 blot.

FIG. 19A. SAOS-2 were infected with AdN5 or AdGFP at an m.o.i. of 10. At the indicated times after infection, cell extracts were prepared and assayed for caspase activity using the colorimetric peptide substrates shown. Cleavage of the peptide causes an increase in OD405. The data presented show the mean OD405 of assays done in triplicate. The data for AdGFP infection are not shown, because none of the extracts demonstrated OD405 readings above background. Only three peptides were cleaved by the AdN5-infected extracts, VEID, DEVD, and LEHD (shown as white symbols). FIG. 19B. Equal quantities of total protein from extracts prepared as above were analyzed for caspases-6 or -9 by Western blotting. The caspase-6 antibody recognizes the zymogen and the p18 processed form. The caspase-9 antibody recognizes the zymogen and the p35 processed form. Processed caspase-6 can be readily detected by day 2 following infection, whereas caspase-9 is not readily detected until day 4.

FIG. 20A. 293 cells were transfected with pCMV or pCMVN5. Cytoplasmic or nuclear extracts were prepared from these cells 24 h later. Equal quantities of total protein were analyzed by Western blotting using an anti-p65RelA antibody. Staining with anti-b-actin served as a protein loading control. FIG. 20B. 293 cells were cotransfected with a luciferase re-porter gene construct whose expression was driven by a wild-type or mutant NF-kB-dependent promoter, pEGFPC-1, and either pCMVN5, a p65RelA expression vector, or the empty vector (CMV). Luciferase activity was determined 24 h after transfection and normalized on the basis of transfection efficiency as determined by the percentage of GFP fluorescent cells. Values shown are the mean of the relative light units for three experiments.

FIG. 21A. 293 cells were transfected with pCMV or pCMVN5. Extracts were prepared 24 h later, and equal quantities of total cell protein were analyzed by Western blotting using anti-Bcl-2, anti-Bax, anti-Bak, anti-Mad, anti-Bcl-Xs, or anti-Bad antibodies. Staining with anti-b-actin served as a protein-loading control. FIG. 21B. SAOS-2 cells were transfected with indicated expression vectors. Apoptosis was measured 24 h later by TUNEL. The data are presented as the ratio of the percentage of TUNEL-positive cells to the percentage of transfected cells. The data are the mean of three experiments.

FIG. 22A. SAOS-2 were cotransfected with indicated expression vectors and analyzed for apoptosis by TUNEL 24 h later as in FIG. 21B. The results are the mean of at least three experiments. FIG. 22B. MCF-7 cells (wild-type p53) or SAOS-2 cells (p53 null) were cotransfected with pCMVN5 and pEG-FPc-1. Transfected cells were analyzed for apoptosis by TUNEL 24 h later as in FIG. 21B. The data are the mean of at least three experiments. FIG. 22C. 293 cells were transfected with pCMV, pCMVN5. Extracts were prepared 24 h later, and equal quantities of total protein analyzed by Western blotting using antibodies directed against the indicated proteins. Staining with anti-β-actin served as a protein loading control.

FIG. 26A. A total of 20,000 cells from each line were plated per well of a 12-well plate and treated as indicated at an MOI of 10, except for SKOV3 IP-1 cells, which were treated at an MOI of 50. Aliquots of the infected cells were harvested at the indicated times, and the number of cells excluding trypan blue were counted. The data presented are the mean of three independent experiments.

FIG. 27A. U2OS cells were infected with the indicated virus, and cell proliferation was measured on subsequent days as described in the legend to FIG. 26. For each infection, cells were treated with a total MOI of 20. For example, for AdN5- plus AdRB-treated cells, an MOI of 10 was used for each virus. The cell number divided by 10,000 is indicated. Data are the mean of three infections. FIG. 27B. The cell number divided by 10,000 is shown on day 5 for cells treated with the indicated virus. Note that cell numbers do not decline when coinfected with AdRB as they do when infected with AdN5 alone. The data are the mean and SD of three infections.

DESCRIPTION OF ILLUSTRATIVE EMBODIMENTS

Figure 1A:
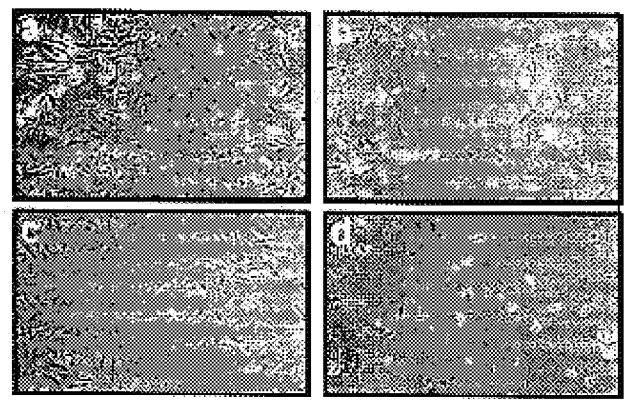
FIG. 1A, FIG. 1B, FIG. 1C and FIG. 1D. Expression of p84N5 decreases cell survival.

The present invention concerns methods and compositions for the treatment of cancer using p84N5. p84N5 encoding nucleic acid or p84N5 protein can be administered by different modes to a cancer patient. The result of this treatment can be the induction of apoptosis, inhibition of cell division, inhibition of metastatic potential, reduction of tumor burden, increased sensitivity to chemotherapy or radiotherapy, killing of a cancer cell, inhibition of the growth of a cancer cell, and induction of tumor regression. p84N5 is known to interact with the retinoblastoma gene product (Rb), to be normally localized to the nucleus of cells and is shown in the present invention to contain a functional death domain. These properties are important attributes of the present invention and are discussed in greater detail in the following sections and examples.

I. Retinoblastoma Gene Product

The retinoblastoma gene (Rb), the first tumor suppressor gene identified, encodes a nuclear phosphoprotein which is ubiquitously expressed in vertebrates (Friend et al., 1986; Lee et al., 1987b; Fung et al., 1987). Mutations of this gene which lead to inactivation of its normal function have been found not only in 100% of retinoblastomas, but also in many other adult cancers including small cell lung-carcinoma (Harbour et al., 1988; Yokota et al., 1988), osteosarcoma (Toguchida et al., 1988), bladder carcinoma (Horowitz et al., 1989), prostate carcinoma (Bookstein et al., 1990a) and breast cancer (Lee et al., 1988). Reconstitution of a variety of Rb-deficient tumor cells with wild-type Rb leads to suppression of their neoplastic phenotypes including their ability to form tumors in nude mice (Huang et al., 1988; Sumegi et al., 1990; Bookstein et al., 1990b; Lee et al., 1990; Goodrich et al., 1992; Takahashi et al., 1991; Chen et al., 1992). These results provide direct evidence that Rb protein is an authentic tumor suppressor.

Rb performs its function at the early G1/G0 phase of the cell cycle as substantiated by several observations: first, the phosphorylation of Rb, presumably by members of the Cdk kinase family (Lin et al., 1991; Lee et al., 1991), fluctuates with the cell cycle (Chen et al., 1989; Buchkovich et al., 1989; DeCaprio et al., 1989); second, the unphosphorylated form of Rb is present predominantly in the G0/G1 stage (Chen et al., 1989; DeCaprio et al., 1989); third, microinjection of the unphosphorylated Rb into cells at early G1 phase inhibits their progression into S phase (Goodrich et al., 1991). These observations suggest that Rb may serve as a critical regulator of entry into cell cycle and its inactivation in normal cells could lead to deregulated growth.

Two known biochemical properties of the Rb protein have been described; one is its intrinsic DNA binding activity which was mapped to its C-terminal 300 amino acid residues (Lee et al., 1987b; Wang et al., 1990b); another is its ability to interact with several oncoproteins of the DNA tumor viruses (DeCaprio et al., 1988; Whyt, et al., 1988; Dyson et al., 1989). This interaction was mapped to two discontinuous regions at amino acids 379–545 and 575–678, designated as the T-binding domains (Hu et al., 1990; Huang et al., 1990). Interestingly, mutations of the Rb proteins in tumors were frequently located in these same regions (Bookstein and Lee, 1991). These results imply that the T-binding domains of Rb proteins are functionally important and the interaction of Rb with these oncoproteins may have profound biological significance. The identification of cellular proteins that mimic the binding of T to Rb revealed a potentially complicated network. Several proteins including c-myc (Rustgi et al., 1991), Rb-p1, p2 (Defeo-Jones et al., 1991) and other proteins (Kaelin et al., 1991; Lee et al., 1991; Huang et al., 1991) have been shown to bind to Rb in vitro. At the present time, approximately 60 proteins have been implicated in binding Rb protein.

Retinoblastoma is a neoplastic condition of the retinal cells, observed almost exclusively in children between the ages of 0 and 4 years. It affects between 1 in 34,000 and 1 in 15,000 live births in the United States (Zimmerman, 1985). If untreated, the malignant neoplastic retinal cells in the intraocular tumor travel to other parts of the body, forming foci of uncontrolled growth which are always fatal. The current treatment for a retinoblastoma is enucleation of the affected eye if the intraocular tumor is large; for small intraocular tumors, radiation therapy, laser therapy, or cryotherapy is preferred. There is no known successful treatment for metastatic retinoblastoma. As with most cancers, morbidity and mortality are reduced if diagnosis can be made early in the course of the disease.

In 30–40% of cases of retinoblastoma, the affected individual carries a heritable predisposition to retinoblastoma and can transmit this predisposition to his or her offspring as a dominant trait (Knudson, 1971). Carriers of this retinoblastoma-predisposing trait are at a greatly elevated risk for development of several other forms of primary cancer, notably osteosarcoma and soft-tissue sarcoma.

II. Death Domains and Apoptosis

The present invention concerns compositions and methods for treating cancer using the p84N5 gene and p84N5 protein. In preferred embodiments, the p84N5 gene sequence or protein sequence contains a functioning death domain. The "death domain" is defined as that portion of p84N5 that, when expressed or introduced into a tumor cell, induces apoptosis, inhibits cell division, inhibits metastatic potential, reduces tumor burden, increases sensitivity to chemotherapy or radiotherapy, kills a cancer cell, inhibits the growth of a cancer cell, or induces tumor regression. A "death domain" has been identified in the C-terminal region of the p84N5 protein, from about amino acid 568 to about amino acid 657 of SEQ ID NO:2, based on sequence alignment (Feinstein and Kimchi, 1995). However, the a functional death domain may be larger or smaller than that defined by this alignment. A functional death domain in p84N5 may therefore be only a small portion of the protein, from about 10 amino acids to about 15 amino acids, or from about 20 amino acids to about 25 amino acids, or from about 30 amino acids to about 35 amino acids, or from about 40 amino acids to about 45 amino acids, or from about 50 amino acids to about 55 amino acids, or from about 60 amino acids to about 70 amino acids, or from about 80 amino acids to about 90 amino acids, or about 100 amino acids in length. Alternatively, a functional death domain, as defined above, may require a larger portion of the p84N5 protein than that simply defined by sequence alignment. A portion of p84N5 from about 110 amino acids to about 115 amino acids, or from about 120 amino acids to 130 amino acids, or from about 140 amino acids to about 150 amino acids, or from about 160 amino acids to about 170 amino acids, or from about 180 amino acids to about 190 amino acids, or from about 200 amino acids to about 250 amino acids, or from about 300 amino acids to about 350 amino acids, or from about 400 amino acids to about 450 amino acids, or from about 500 amino acids to about 600 amino acids, or the full length protein as defined in SEQ ID NO:2 may be required for function.

The p84N5 death domain, while identified based on sequence alignment (Feinstein and Kimchi, 1995), is further defined herein functionally. A p84N5 death domain is the minimum region of p84N5 that is necessary and sufficient for the generation of cytotoxic death signals, anti-viral responses (Tartaglia et al., 1993), and/or the activation of acid sphingomyelinase (Wiegmann et al., 1994) when overexpressed or ectopically expressed in cells. A functional p84N5 death domain, when overexpressed or ectopically expressed in a cancer cell, is further defined as being capable of inducing apoptosis, inhibiting cell division, inhibiting metastatic potential, reducing tumor burden, increasing sensitivity to chemotherapy or radiotherapy, killing a cancer cell, inhibiting the growth of a cancer cell, or inducing tumor regression.

The term "death domain" was originally coined in 1993 by Tartaglia et al. as a result of deletion mutagenesis studies involving TNF-RI (p55)-mediated apoptotic cell death. These studies revealed that an 80 amino acid domain, which is localized to the C-terminal portion of the protein's intracellular region, is responsible for the generation of cytotoxic death signals, anti-viral responses (Tartaglia et al., 1993), and the activation of acid sphingomyelinase (Wiegmann et al., 1994); it also is partially responsible for, in conjunction with residues in the N-terminal portion in the intracellular region, the induction of nitric oxide (NO) synthase activity (Tartaglia et al., 1993). Homology searches have revealed that the TNF-RI death domain is approximately 65% similar (28% identical) to a 65 amino acid region within the intracellular domain of the Fas antigen; mutagenesis studies have confirmed that these 65 amino acids are required for the induction of cell death following treatment with an anti-Fas antibody in conjunction with actinomycin D (Itoh et al., 1993). Supporting evidence for a functional overlap between the domains of these two receptors was achieved through the generation of a "death signal delivering" chimeric receptor which replaced TNF-RI amino acid residues 324–326 with the corresponding amino acids of the Fas antigen (Tartaglia et al., 1993).

The death domain, aside from being the only homologous intracellular domain that is shared by two members of the TNFR superfamily, generates a cytotoxic signal irrespective of its position with respect to the extracellular domain (Tartaglia et al., 1993). In addition, this domain appears to mediate self-association of both TNF-RI and Fas, thereby mimicking the aggregation of events which are induced by ligand binding to each of these receptors (Boldin et al., 1995). These results, which demonstrate that the death domain is an independent domain at both the structural and functional levels, were recently confirmed by the identification and subsequent characterization of three death domain-containing proteins, each of which can generate an apoptotic signal when overexpressed in cells.

Other proteins containing death domains have more recently been defined based on sequence alignments (Feinstein and Kimchi, 1995). These include the low affinity nerve growth factor receptor and MORT1 (Boldin et al., 1995), the ankyrins (Boldin et al., 1995; Cleveland and Ihle, 1995), two Drosophila proteins, PELLE (Shelton and Wasserman, 1993) and TUBE (Letsou et al., 1991), and the p84N5 protein described in the present application.

Death domains mediate protein-protein interactions with analogous death domain sequences. It is not clear whether the transduction of a cytocidal signal is the only function of death domains. Death domains probably participate in transduction of other signals through unique protein-protein interactions.

The rapid induction of cell death via the death domain is heretofore unique to TNF-RI and Fas; however, despite the characterization of a defined "death inducing" region within each of these receptors, the intermediates involved in the transmission of their signals were, until recently, completely unknown. As with other receptors which are devoid of catalytic activity, TNF-RI and Fas were suspected to utilize cellular protein as "downstream messengers of death." Many charged residues that are well conserved in both proteins were suspected to be widely dispersed throughout portions of the death domains which are oriented to interact with protein components of the cytoplasm (Tartaglia et al., 1993).

To date, three death domain-containing proteins which associate with either TNF-RI or Fas have been identified and characterized with respect to their ability to induce apoptosis and other downstream signaling events which are activated in immune responses achieved through ligand binding to each of these receptors.

III. P84N5 Genes and DNA Segments

Important aspects of the present invention concern isolated DNA segments and recombinant vectors encoding P84N5, and the creation and use of recombinant host cells through the application of DNA technology, that express wild-type, polymorphic or allelic variants of P84N5, using the sequence of SEQ ID NO:1, and biologically functional equivalents thereof.

As used herein, the term "DNA segment" refers to a DNA molecule that has been isolated free of total genomic DNA of a particular species. Therefore, a DNA segment encoding P84N5 refers to a DNA segment that contains wild-type, polymorphic or mutant P84N5 coding sequences yet is isolated away from, or purified free from, genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified P84N5 gene refers to a DNA segment including p84N5 protein coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences and smaller engineered gene segments that express, or may be adapted to express, proteins, polypeptides, domains, peptides, fusion proteins and mutants.

"Isolated substantially a way from other coding sequences" means that the gene of interest, in this case the P84N5 gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that encode a P84N5 protein or peptide that includes within its amino acid sequence a contiguous amino acid sequence in accordance with, or essentially as set forth in, SEQ ID NO:2.

The term "a sequence essentially as set forth in SEQ ID NO:2" means that the sequence substantially corresponds to a portion of SEQ ID NO:2 and has relatively few amino acids that are not identical to, or a biologically functional equivalent of, the amino acids of SEQ ID NO:2.

The term "biologically functional equivalent" is well understood in the art and is further defined in detail herein. Accordingly, sequences that have between about 70% and about 80%; or more preferably, between about 81% and about 90%; or even more preferably, between a bout 91% and about 99%; of amino acids that are identical or functionally equivalent to the amino acids of SEQ ID NO:2 will be sequences that are "essentially as set forth in SEQ ID NO:2", provided the biological activity of the protein is maintained.

In certain other embodiments, the invention concerns isolated DNA segments and recombinant vectors that include within their sequence a nucleic acid sequence essentially as set forth in SEQ ID NO:1. The term "essentially as set forth in SEQ ID NO:1" is used in the same sense as described above and means that the nucleic acid sequence substantially corresponds to a portion of SEQ ID NO:1 and has relatively few codons that are not identical, or functionally equivalent, to the codons of SEQ ID NO:1. Again, DNA segments that encode proteins exhibiting p84N5 activity will be most preferred.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have between about 70% and about 79%; or more preferably, between about 80% and about 89%; or even more preferably, between about 90% and about 99%; of nucleotides that are identical to the nucleotides of SEQ ID NO:1 will be sequences that are "essentially as set forth in SEQ ID NO:1".

Sequences that are essentially the same as those set forth in SEQ ID NO:1 may also be functionally defined as sequences that are capable of hybridizing to a nucleic acid segment containing the complement of SEQ ID NO:1 under relatively stringent conditions. Suitable relatively stringent hybridization conditions will be well known to those of skill in the art, as disclosed herein.

Hybridization is understood to mean the forming of a double-stranded molecule or a molecule with partial double-stranded nature. Stringent conditions are those that allow hybridization between two homologous nucleic acid sequences, but precludes hybridization of random sequences. For example, hybridization at low temperature and/or high ionic strength is termed low stringency. Hybridization at high temperature and/or low ionic strength is termed high stringency. Low stringency is generally performed at 0.15 M to 0.9 M NaCl at a temperature range of 20° C. to 50° C. High stringency is generally performed at 0.02 M to 0.15 M NaCl at a temperature range of 50° C. to 70° C. It is understood that the temperature and ionic strength of a desired stringency are determined in part by the length of the particular probe, the length and base content of the target sequences, and to the presence of formamide, tetramethylammonium chloride or other solvents in the hybridization mixture. It is also understood that these ranges are mentioned by way of example only, and that the desired stringency for a particular hybridization reaction is often determined empirically by comparison to positive and negative controls.

Accordingly, the nucleotide sequences of the disclosure may be used for their ability to selectively form duplex molecules with complementary stretches of genes or RNAs or to provide primers for amplification of DNA or RNA from tissues. Depending on the application envisioned, it is preferred to employ varying conditions of hybridization to achieve varying degrees of selectivity of probe towards target sequence.

For applications requiring high selectivity, it is preferred to employ relatively stringent conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe and the template or target strand, and would be particularly suitable for isolating specific genes or detecting specific mRNA transcripts. It is generally appreciated that conditions may be rendered more stringent by the addition of increasing amounts of formamide.

Naturally, the present invention also encompasses DNA segments that are complementary, or essentially complementary, to the sequence set forth in SEQ ID NO:1. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 under relatively stringent conditions such as those described herein.

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

For example, nucleic acid fragments may be prepared that include a contiguous stretch of nucleotides identical to or complementary to SEQ ID NO:1, such as about 8, about 10 to about 14, or about 15 to about 20 nucleotides, and that are up to about 1,000,000, about 750,000, about 500,000, about 250,000, about 100,000, about 50,000, about 20,000, or about 10,000, or about 5,000 base pairs in length, with segments of about 3,000 being preferred in certain cases. In certain cases, nucleotide segments of a million bases or more, including chromosome sized pieces of DNA, are contemplated as being useful. DNA segments with total lengths of about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200–500; 500–1,000; 1,000–2,000; 2,000–3,000; 3,000–5,000; 5,000–10,000 ranges, up to and including sequences of about 12,001, 12,002, 13,001, 13,002, 15,000, 20,000 and the like.

The various probes and primers designed around the disclosed nucleotide sequences of the present invention may be of any length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 10-mer, the probes correspond to bases 1 to 10, 2 to 11, 3 to 12 . . . and so on. For a 15-mer, the probes correspond to bases 1 to 15, 2 to 16, 3 to 17 . . . and so on. For a 20-mer, the probes correspond to bases 1 to 20, 2 to 21, 3 to 22 . . . and so on.

It also will be understood that this invention is not limited to the particular nucleic acid and amino acid sequences of SEQ ID NO:1. Recombinant vectors and isolated DNA segments may therefore variously include these coding regions themselves, coding regions bearing selected alterations or modifications in the basic coding region, or they may encode larger polypeptides that nevertheless include such coding regions or may encode biologically functional equivalent proteins or peptides that have variant amino acids sequences.

The DNA segments of the present invention encompass biologically functional equivalent P84N5 proteins, polypeptides, and peptides. Such sequences may arise as a consequence of codon redundancy and functional equivalency that are known to occur naturally within nucleic acid sequences and the proteins thus encoded. Alternatively, functionally equivalent proteins, polypeptides or peptides may be created via the application of recombinant DNA technology, in which changes in the protein structure may be engineered, based on considerations of the properties of the amino acids being exchanged. Changes designed by man may be introduced, for example, through the application of site-directed mutagenesis techniques as discussed herein below, e.g., to introduce improvements to the antigenicity of the protein or to test mutants in order to examine p84N5 activity at the molecular level.

One also may prepare fusion proteins, polypeptides and peptides, e.g., where the p84N5 protein coding regions are aligned within the same expression unit with other proteins or peptides having desired functions, such as for purification or immunodetection purposes (e.g., proteins that may be purified by affinity chromatography and enzyme label coding regions, respectively).

Encompassed by the invention are DNA segments encoding relatively small peptides, such as, for example, peptides of from about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 35, about 40, about 45, to about 50 amino acids in length, and more preferably, of from about 15 to about 30 amino acids in length; as set forth in SEQ ID NO:2 and also larger polypeptides up to and including proteins corresponding to the full-length sequences set forth in SEQ ID NO:2.

IV Genetic Constructs

Throughout this application, the term "expression construct" is meant to include any type of genetic construct containing a nucleic acid coding for gene products, such as p84N5, in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding genes of interest.

(i) Promoters

The nucleic acid encoding a gene product is under transcriptional control of a promoter. A "promoter" refers to a DNA sequence recognized by the machinery of the cell, or introduced machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of Drosophila, and when ecdysone or an analog such as muristerone A binds to the receptor, the receptor activates a promoter to turn on expression of the downstream transgene high levels of mRNA transcripts are attained. In this system, both monomers of the heterodimeric receptor are constituitively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of E. coli. The tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constituitively on. In the Tet-On™ system, the tetracycline repressor is not wild-type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constituitively on.

In some circumstances, it may be desirable to regulate expression of a transgene in a gene therapy vector. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Similarly, the following promoters may be used to target gene expression in other tissues (Table 1).

TABLE 1

Tissue specific promoters

| Tissue | Promoter |
|---|---|
| Pancreas | insulin |
| | elastin |
| | amylase |
| | pdr-1 pdx-1 |
| | glucokinase |
| Liver | albumin PEPCK |
| | HBV enhancer |
| | alpha fetoprotein |
| | apolipoprotein C |
| | alpha-1 antitrypsin |
| | vitellogenin, NF-AB |
| | Transthyretin |
| Skeletal muscle | myosin H chain |
| | muscle creatine kinase |
| | dystrophin |
| | calpain p94 |
| | skeletal alpha-actin |
| | fast troponin 1 |
| Skin | keratin K6 |
| | keratin K1 |
| Lung | CFTR |
| | human cytokeratin 18 (K18) |
| | pulmonary surfactant proteins A, B and C |
| | CC-10 |
| | P1 |
| Smooth muscle | sm22 alpha |
| | SM-alpha-actin |
| Endothelium | endothelin-1 |
| | E-selectin |
| | von Willebrand factor |
| | TIE (Korhonen et al., 1995) |
| | KDR/flk-1 |
| Melanocytes | tyrosinase |
| Adipose tissue | lipoprotein lipase (Zechner et al., 1988) |
| | adipsin (Spiegelman et al., 1989) |
| | acetyl-CoA carboxylase (Pape and Kim, 1989) |
| | glycerophosphate dehydrogenase (Dani et al., 1989) |
| | adipocyte P2 (Hunt et al., 1986) |
| Blood | β-globin |

In certain indications, it may be desirable to activate transcription at specific times after administration of the gene therapy vector. This may be done with such promoters as those that are hormone or cytokine regulatable. For example in gene therapy applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones are expected to be useful in the present invention. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitypsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin.

It is envisioned that cell cycle regulatable promoters may be useful in the present invention. For example, in a bi-cistronic gene therapy vector, use of a strong CMV promoter to drive expression of a first gene such as p16 that arrests cells in the G1 phase could be followed by expression of a second gene such as p53 under the control of a promoter that is active in the G1 phase of the cell cycle, thus providing a "second hit" that would push the cell into apoptosis. Other promoters such as those of various cyclins, PCNA, galectin-3, E2F1, p53 and BRCA1 could be used.

Tumor specific promoters such as osteocalcin, hypoxia-responsive element (HRE), MAGE-4, CEA, alpha-fetoprotein, GRP78/BiP and tyrosinase also may be used to regulate gene expression in tumor cells. Other promoters that could be used according to the present invention include Lac-regulatable, chemotherapy inducible (e.g. MDR), and heat (hyperthermia) inducible promoters, Radiation-inducible (e.g., EGR (Joki et al., 1995)), Alpha-inhibin, RNA pol III tRNA met and other amino acid promoters, U1 snRNA (Bartlett et al., 1996), MC-1, PGK, -actin and alpha-globin. Many other promoters that may be useful are listed in Walther and Stein (1996).

It is envisioned that any of the above promoters alone or in combination with another may be useful according to the present invention depending on the action desired. In addition, this list of promoters is should not be construed to be exhaustive or limiting, those of skill in the art will know of other promoters that may be used in conjunction with the promoters and methods disclosed herein.

(ii) Enhancers

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters additional to the tissue specific promoters listed above, cellular promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

ENHANCER

Immunoglobulin Heavy Chain
Immunoglobulin Light Chain
T-Cell Receptor
HLA DQ α and DQ β
β-Interferon
Interleukin-2
Interleukin-2 Receptor
MHC Class II 5
MHC Class II HLA-DRα
β-Actin
Muscle Creatine Kinase
Prealbumin (Transthyretin)
Elastase I
Metallothionein
Collagenase
Albumin Gene
α-Fetoprotein
τ-Globin
β-Globin
e-fos
c-HA-ras
Insulin
Neural Cell Adhesion Molecule (NCAM)
α1-Antitrypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon Ape Leukemia Virus

TABLE 3

| Element | Inducer |
|---|---|
| MT II | Phorbol Ester (TPA) |
|  | Heavy metals |
| MMTV (mouse mammary tumor virus) | Glucocorticoids |
| β-Interferon | poly(rI)X |
|  | poly(rc) |
| Adenovirus 5 E2 | Ela |
| c-jun | Phorbol Ester (TPA), H₂O₂ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

(iii) Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human or bovine growth hormone and SV40 polyadenylation signals. Also contemplated as an element of the expression cassette is a terminator. These elements can serve to enhance message levels and to minimize read through from the cassette into other sequences.

V. Antisense Constructs

The term "antisense nucleic acid" is intended to refer to the oligonucleotides complementary to the base sequences of DNA and RNA. Antisense oligonucleotides, when introduced into a target cell, specifically bind to their target nucleic acid and interfere with transcription, RNA processing, transport and/or translation. Targeting double-stranded (ds) DNA with oligonucleotide leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense RNAs, may be employed to inhibit gene transcription or translation or both within a host cell, either in vitro or in vivo, such as within a host animal, including a human subject. Nucleic acid sequences comprising "complementary nucleotides" are those which are capable of base-pairing according to the standard Watson-Crick complementary rules. That is, that the larger purines will base pair with the smaller pyrimidines to form only combinations of guanine paired with cytosine (G:C) and adenine paired with either thymine (A:T), in the case of DNA, or adenine paired with uracil (A:U) in the case of RNA.

As used herein, the terms "complementary" or "antisense sequences" mean nucleic acid sequences that are substantially complementary over their entire length and have very few base mismatches. For example, nucleic acid sequences of fifteen bases in length may be termed complementary when they have a complementary nucleotide at thirteen or fourteen positions with only single or double mismatches. Naturally, nucleic acid sequences which are "completely complementary" will be nucleic acid sequences which are entirely complementary throughout their entire length and have no base mismatches.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

VI. Ribozyme Constructs

As an alternative to targeted antisense delivery, targeted ribozymes may be used. The term "ribozyme" refers to an RNA-based enzyme capable of targeting and cleaving particular base sequences in oncogene DNA and RNA. Ribozymes either can be targeted directly to cells, in the form of RNA oligo-nucleotides incorporating ribozyme sequences, or introduced into the cell as an expression construct encoding the desired ribozymal RNA. Ribozymes may be used and applied in much the same way as described for antisense nucleic acids.

VII. Methods of Gene Transfer

In order to mediate the effect of transgene expression in a cell, it will be necessary to transfer the therapeutic expression constructs of the present invention into a cell. This section provides a discussion of methods and compositions of viral production and viral gene transfer, as well as non-viral gene transfer methods.

(i) Viral Vector-Mediated Transfer

The p84N5 genes are incorporated into a viral infectious particle to mediate gene transfer to a cell. Additional expression constructs encoding other therapeutic agents as described herein may also be transferred via viral transduction using infectious viral particles, for example, by transformation with an adenovirus vector of the present invention as described herein below. Alternatively, retroviral or bovine papilloma virus may be employed, both of which permit permanent transformation of a host cell with a gene(s) of interest. Thus, in one example, viral infection of cells is used in order to deliver therapeutically significant genes to a cell. Typically, the virus simply will be exposed to the appropriate host cell under physiologic conditions, permitting uptake of the virus. Though adenovirus is exemplified, the present methods may be advantageously employed with other viral or non-viral vectors, as discussed below.

Adenovirus

Adenovirus is particularly suitable for use as a gene transfer vector because of its mid-sized DNA genome, ease of manipulation, high titer, wide target-cell range, and high infectivity. The roughly 36 kB viral genome is bounded by 100–200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible achieve both these goals while retaining the ability to manipulate the therapeutic constructs with relative ease.

The large displacement of DNA is possible because the cis elements required for viral DNA replication all are localized in the inverted terminal repeats (ITR) (100–200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194–385 bp (0.5–1.1 map units) at the left end of the viral genome (Hearing et al., 1987). This signal mimics the protein recognition site in bacteriophage λ DNA where a specific sequence close to the left end, but outside the cohesive end sequence, mediates the binding to proteins that are required for insertion of the DNA into the head structure. E1 substitution vectors of Ad have demonstrated that a 450 bp (0–1.25 map units) fragment at the left end of the viral genome could direct packaging in 293 cells (Levrero et al., 1991).

Previously, it has been shown that certain regions of the adenoviral genome can be incorporated into the genome of manunalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194–358 bp) region of the genome grew poorly even in a cell line that complemented the early (E1A) function (Hearing and Shenk, 1983). When a compensating adenoviral DNA (0–353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

Retrovirus

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., 1975).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

Adeno-associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathological state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al. 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, 1996 ; Chatterjee et al., 1995; Ferrari et al., 1996; Fisher et al., 1996; Flotte et al., 1993; Goodman et al., 1994; Kaplitt et al., 1994; 1996, Kessler et al., 1996; Koeberl et al., 1997; Mizukami et al., 1996; Xiao et al., 1996).

AAV-mediated efficient gene transfer and expression in the lung has led to clinical trials for the treatment of cystic fibrosis (Carter and Flotte, 1996; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996).

Other Viral Vectors

Other viral vectors may be employed as expression constructs in the present invention. Vectors derived from viruses such as vaccinia virus (Ridgeway, 1988; Baichwal and Sugden, 1986; Coupar et al., 1988) and hepatitis B viruses have also been developed and are useful in the present invention. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al., recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

(ii) Non-viral Transfer

DNA constructs of the present invention are generally delivered to a cell, in certain situations, the nucleic acid to be transferred is non-infectious, and can be transferred using non-viral methods.

Several non-viral methods for the transfer of expression constructs into cultured mammalian cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene therapy.

Liposome-mediated nucleic acid delivery and expression of foreign DNA in vitro has been very successful. Using the β-lactamase gene, Wong et al. (1980) demonstrated the feasibility of liposome-mediated delivery and expression of foreign DNA in cultured chick embryo, HeLa, and hepatoma cells. Nicolau et al. (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al., 1986) may be used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM may also be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

VII. Pharmaceuticals and Methods of Treating Cancer

In a particular aspect, the present invention provides methods for the treatment of various malignancies. Treatment methods will involve treating an individual with an effective amount of a viral particle, as described above, containing a gene encoding a p84N5 death domain. Alternatively, treatment methods will involve treating an individual with an effective amount of a p84N5 protein composition. An effective amount is described, generally, as that amount sufficient to detectably and repeatedly to induce apoptosis, inhibit cell division, inhibit metastatic potential, reduce tumor burden, increase sensitivity to chemotherapy or radiotherapy, kill a cancer cell, inhibit the growth of a cancer cell, or induce tumor regression.

To kill cells, inhibit cell growth, inhibit metastasis, decrease tumor size and otherwise reverse or reduce the malignant phenotype of tumor cells, using the methods and compositions of the present invention, one would generally contact a "target" cell with the therapeutic viral or protein composition. This may be combined with compositions comprising other agents effective in the treatment of cancer. These compositions would be provided in a combined amount effective to kill or inhibit proliferation of the cell. This process may involve contacting the cells with the viral or protein composition and the agent(s) or factor(s) at the same time. This may be achieved by contacting the cell with a single composition or pharmacological formulation that includes both agents, or by contacting the cell with two distinct compositions or formulations, at the same time, wherein one composition includes the viral or protein composition and the other includes the second agent.

Alternatively, the treatment may precede or follow the other agent treatment by intervals ranging from minutes to weeks. In embodiments where the other agent and viral or protein composition are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 h of each other and, more preferably, within about 6–12 h of each other, with a delay time of only about 12 h being most preferred. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Administration of the therapeutic viral or protein composition of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described treatments.

Where clinical application of a composition is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the compound, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

The compositions of the present invention may include classic pharmaceutical preparations. Dispersions also can be prepared in glycerol, liquid polyethylene glycols, and mixtures thereof and in oils. Under ordinary conditions of storage and use, these preparations contain a preservative to prevent the growth of microorganisms.

Depending on the particular cancer to be, administration of therapeutic compositions according to the present invention will be via any common route so long as the target tissue is available via that route. This includes oral, nasal, buccal, rectal, vaginal or topical. Topical administration would be particularly advantageous for treatment of skin cancers. Alternatively, administration will be by orthotopic, intradermal, subcutaneous, intramuscular, intraperitoneal or intravenous injection. Such compositions would normally be administered as pharmaceutically acceptable compositions that include physiologically acceptable carriers, buffers or other excipients.

In certain embodiments, ex vivo therapies also are contemplated. Ex vivo therapies involve the removal, from a patient, of target cells. The cells are treated outside the patient's body and then returned. One example of ex vivo therapy would involve a variation of autologous bone marrow transplant. Many times, ABMT fails because some cancer cells are present in the withdrawn bone marrow, and return of the bone marrow to the treated patient results in repopulation of the patient with cancer cells. In one embodiment, however, the withdrawn bone marrow cells could be treated while outside the patient with an viral particle that targets and kills the cancer cell. Once the bone marrow cells are "purged," they can be reintroduced into the patient.

The treatments may include various "unit doses." Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

Preferably, patients will have adequate bone marrow function (defined as a peripheral absolute granulocyte count of >2,000/mm$^3$ and a platelet count of 100,000/mm$^3$), adequate liver function (bilirubin <1.5 mg/dl) and adequate renal function (creatinine <1.5 mg/dl).

One of the preferred embodiments of the present invention involves the use of viral vectors to deliver therapeutic genes to cancer cells. Alternatively, another embodiment of the present invention involves the use of therapeutic protein compositions. Target cancer cells include cancers of the lung, brain, prostate, kidney, liver, ovary, breast, skin, stomach, esophagus, head and neck, testicles, colon, cervix, lymphatic system and blood. Of particular interest are non-small cell lung carcinomas including squamous cell carcinomas, adenocarcinomas and large cell undifferentiated carcinomas.

According to the present invention, one may treat the cancer by directly injection a tumor with the viral vector or protein composition. Alternatively, the tumor may be infused or perfused with the vector or protein using any suitable delivery vehicle. Local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe or catherization is preferred. Such continuous perfusion may take place for a period from about 1–2 hours, to about 2–6 hours, to about 6–12 hours, to about 12–24 hours, to about 1–2 days, to about 1–2 wk or longer following the initiation of treatment. Generally, the dose of the therapeutic composition via continuous perfusion will be equivalent to that given by a single or multiple injections, adjusted over a period of time during which the perfusion occurs.

For tumors of >4 cm, the volume to be administered will be about 4–10 ml (preferably 10 ml), while for tumors of <4 cm, a volume of about 1–3 ml will be used (preferably 3 ml). Multiple injections delivered as single dose comprise about 0.1 to about 0.5 ml volumes. The viral particles or protein may advantageously be contacted by administering multiple injections to the tumor, spaced at approximately 1 cm intervals.

In certain embodiments, the tumor being treated may not, at least initially, be resectable. Treatments with therapeutic viral constructs or protein compositions may increase the resectability of the tumor due to shrinkage at the margins or by elimination of certain particularly invasive portions. Following treatments, resection may be possible. Additional viral or protein treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two-week period. The two-week regimen may be repeated one, two, three, four, five, six or more times. During a course of treatment, the need to complete the planned dosings may be re-evaluated.

(i) Combination Therapies

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate or any analog or derivative variant thereof.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Various combinations may be employed, gene therapy is "A" and the radio- or chemotherapeutic agent is "B":

| | | | | | | |
|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | |
| B/A/B/A | B/A/A/B | A/A/A/B | B/A/A/A | A/B/A/A | A/A/B/A | |

The terms "contacted" and "exposed," when applied to a cell, are used herein to describe the process by which a therapeutic construct or protein and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

IX. p84N5 Expression and Purification Systems

Both cDNA and genomic sequences are suitable for eukaryotic expression, as the host cell will generally process the genomic transcripts to yield functional mRNA for translation into protein. For prokaryotic expression, cDNA sequences are preferred. Generally speaking, it may be more convenient to employ as the recombinant gene a cDNA version of the gene, such as that shown in SEQ ID NO:1. It is believed that the use of a cDNA version will provide advantages in that the size of the gene will generally be much smaller and more readily employed to transfect the targeted cell than will a genomic gene, which will typically be up to an order of magnitude or more larger than the cDNA gene. However, it is contemplated that a genomic version of a particular gene may be employed where desired.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

It is proposed that p84N5 proteins, polypeptides or peptides may be co-expressed with other selected proteins, wherein the proteins may be co-expressed in the same cell or p84N5 gene may be provided to a cell that already has another selected protein. Co-expression may be achieved by co-transfecting the cell with two distinct recombinant vectors, each bearing a copy of either of the respective DNA. Alternatively, a single recombinant vector may be constructed to include the coding regions for both of the proteins, which could then be expressed in cells transfected with the single vector. In either event, the term "co-expression" herein refers to the expression of both the p84N5 gene and the other selected protein in the same recombinant cell.

As used herein, the terms "engineered" and "recombinant" cells or host cells are intended to refer to a cell into which an exogenous DNA segment or gene, such as a cDNA or gene encoding an p84N5 protein has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant p84N5 protein, polypeptide or peptide, whether mutant or wild-type, in accordance with the present invention one would prepare an expression vector that comprises a wild-type, or mutant p84N5 protein-encoding nucleic acid under the control of one or more promoters. To bring a coding sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein, polypeptide or peptide expression in a variety of host-expression systems. Cell types available for expression include, but are not limited to, bacteria, such as E. coli and B. subtilis transformed with recombinant bacteriophage DNA, plasmid DNA or cosmid DNA expression vectors.

Certain examples of prokaryotic hosts are E. coli strain RRI, E. coli LE392, E. coli B, E. coli X 1776 (ATCC No. 31537) as well as E. coli W3110 (F-, lambda-, prototrophic, ATCC No. 273325); bacilli such as Bacillus subtilis; and other enterobacteriaceae such as Salmonella typhimurium, Serratia marcescens, and various Pseudomonas species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as E. coli LE392.

Further useful vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

The following details concerning recombinant protein production in bacterial cells, such as E. coli, are provided by way of exemplary information on recombinant protein production in general, the adaptation of which to a particular recombinant expression system will be known to those of skill in the art.

Bacterial cells, for example, E. coli, containing the expression vector are grown in any of a number of suitable media, for example, LB. The expression of the recombinant protein may be induced, e.g., by adding IPTG to the media or by switching incubation to a higher temperature. After culturing the bacteria for a further period, generally of between 2 and 24 hours, the cells are collected by centrifugation and washed to remove residual media.

The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents, such as β-mercaptoethanol or DTT (dithiothreitol).

Under some circumstances, it may be advantageous to incubate the protein for several hours under conditions suitable for the protein to undergo a refolding process into a conformation which more closely resembles that of the native protein. Such conditions generally include low protein concentrations, less than 500 mg/ml, low levels of reducing agent, concentrations of urea less than 2 M and often the presence of reagents such as a mixture of reduced and oxidized glutathione which facilitate the interchange of disulfide bonds within the protein molecule.

The refolding process can be monitored, for example, by SDS-PAGE, or with antibodies specific for the native molecule (which can be obtained from animals vaccinated with the native molecule or smaller quantities of recombinant protein). Following refolding, the protein can then be purified further and separated from the refolding mixture by chromatography on any of several supports including ion exchange resins, gel permeation resins or on a variety of affinity columns.

For expression in Saccharomyces, the plasmid YRp7, for example, is commonly used. This plasmid already contains the trpl gene which provides a selection marker for a mutant strain of yeast lacking the ability to grow in tryptophan, for example ATCC No. 44076 or PEP4-1. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more p84N5 protein, polypeptide or peptide coding sequences.

In a useful insect system, *Autograph californica* nuclear polyhedrosis virus (AcNPV) is used as a vector to express foreign genes. The virus grows in *Spodoptera frugiperda* cells. The p84N5 protein, polypeptide or peptide coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051, Smith, incorporated herein by reference).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein.

Different host cells have characteristic and specific mechanisms for the post-translational processing and modification of proteins. Appropriate cells lines or host systems can be chosen to ensure the correct modification and processing of the foreign protein expressed.

Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the p84N5, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1, E3, or E4) will result in a recombinant virus that is viable and capable of expressing p84N5 proteins, polypeptides or peptides in infected hosts.

Specific initiation signals may also be required for efficient translation of p84N5 protein, polypeptide or peptide coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements and transcription terminators.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of a recombinant p84N5 protein, polypeptide or peptide, stable expression is preferred. For example, cell lines that stably express constructs encoding an p84N5 protein, polypeptide or peptide may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited to, the herpes simplex virus thymidine kinase (tk), hypoxanthine-guanine phosphoribosyltransferase (hgprt) and adenine phosphoribosyltransferase (aprt) genes, in tk$^-$, hgprt$^-$ or aprt$^-$ cells, respectively. Also, antimetabolite resistance can be used as the basis of selection for dihydrofolate reductase (dhfr), that confers resistance to methotrexate; gpt, that confers resistance to mycophenolic acid; neomycin (neo), that confers resistance to the aminoglycoside G-418; and hygromycin (hygro), that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

It is contemplated that the p84N5 proteins, polypeptides or peptides of the invention may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural cells is indicative of overexpression, as is a relative abundance of the specific protein in relation to the other proteins produced by the host cell and, e.g., visible on a gel.

Purification techniques may find use in the current invention, for example, in the purification of the p84N5 protein. Purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; and isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography.

X. Pharmaceutical Formulations

Aqueous compositions of the present invention comprise an effective amount of the p84N5 protein or recombinant viral vector encoding p84N5 dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards. The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes.

The preparation of an aqueous composition that contains an p84N5 polypeptide or p84N5 encoding gene composition as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An p84N5 polypeptide or p84N5 polypeptide encoding gene composition can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In terms of using peptide therapeutics as active ingredients, the technology of U.S. Pat. Nos. 4,608,251; 4,601,903; 4,599,231; 4,599,230; 4,596,792; and 4,578,770, each incorporated herein by reference, may be used.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in I ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

The active p84N5 polypeptides or agents may be formulated within a therapeutic mixture to comprise about 0.0001 to 1.0 milligrams, or about 0.001 to 0.1 milligrams, or about 0.1 to 1.0 or even about 10 milligrams per dose or so. In preferred embodiments, the active p84N5 polypeptides or agents are formulated within a therapeutic mixture to comprise about 0.001 to about 1 milligram. Multiple doses can also be administered In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

One may also use nasal solutions or sprays, aerosols or inhalants in the present invention. Nasal solutions are usually aqueous solutions designed to be administered to the nasal passages in drops or sprays. Nasal solutions are prepared so that they are similar in many respects to nasal secretions, so that normal ciliary action is maintained. Thus, the aqueous nasal solutions usually are isotonic and slightly buffered to maintain a pH of 5.5 to 6.5.

In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Additional formulations which are suitable for other modes of administration include vaginal suppositories and pessaries. A rectal pessary or suppository may also be used.

Suppositories are solid dosage forms of various weights and shapes, usually medicated, for insertion into the rectum, vagina or the urethra. After insertion, suppositories soften, melt or dissolve in the cavity fluids.

In general, for suppositories, traditional binders and carriers may include, for example, polyalkylene glycols or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25–60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

XI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Cell Culture

SAOS-2, 5637, 293 cell lines were obtained from American type culture collection and maintained in Dulbecco's modified Eagle's medium with 10% heat-inactivated fetal bovine serum and antibiotics (100 units/ml penicillin, 100 µg/ml streptomycin), in a 5% $CO_2$ incubator at 37° C.

Plasmids

The cDNAs encoding p84N5 was subcloned into the pCEP4 expression vector (Invitrogen) to create pCMVN5.

The p35 (Clem and Miller, 1994), Bcl-2 (McDonnell et al., 1990), p110Rb, and p110RbΔCdk (Leng et al., 1997) cDNAs were also expressed under control of the cytomegalovirus promoter in pCDNA3.1 (p110RbΔCdk) or pCMV (p35, Bcl-2). PCR-based site-directed mutagenesis was carried out as previously described (Fisher and Pei, 1995). The template for PCR mutagenesis was the complete N5 cDNA inserted into pBSK (Stratagene). The N5-PP mutant was created using the following pair of adjacent phosphorylated primers: N5DD1.2 (5' CT TGA TCT TGC SRG GCA ACC RSG AGC TGC TTA GC 3', SEQ ID NO:3) and N5A4R (5' AG GGA GTT CAT GCA ACA CCT G 3', SEQ ID NO:4). The N5Δα4 deletion mutant was created with the phosphorylated primers: N5A4F (5' TCA TGT CTT CAC TGT CAC ACT 3', SEQ ID NO:5) and N5A4R (SEQ ID NO:4). Mutagenesis creates an in-frame deletion of nucleotides in the 1843 to 1884 of the N5 cDNA. The Sculptor in vitro mutagenesis system (Amersham) was used according to manufacturer's specifications to create the N5-R mutant. The HindIII to BamHI N5 fragment from pCMVN5 was inserted into M13mp19 and served as the single strand DNA template for mutagenesis. The N5DD1.2 oligonucleotide (SEQ ID NO:3) was used as the primer. The mutations were confirmed by sequence analysis using the Thermo Sequenase radiolabeled terminator cycle sequencing kit according to manufacturer's recommendations (Amersham).

Transfection Assays

5637, SAOS-2 or, 293 cells were seeded in 100-mm dishes the day prior to transfection. Cells were transfected by the calcium phosphate precipitation method (Wigler et al., 1979) using 6–30 µg of total DNA. For cotransfections, 6 µg of pCMVN5 and 24 µg of Bcl-2, p35, pCrmA, or pRb were used. Subsequent to transfection, attached and detached cells were collected separately at the indicated times. Cell viability was assessed by Trypan blue staining in each cell population. Cell populations were then pooled and analyzed further.

β-Gal activity in transfected cells was visualized subsequent to fixation with 5% glutaraldehyde in PBS for 15 min followed by extensive washing in PBS containing 5 mM $MgCl_2$. Cells were stained in PBS containing 20 mM $K_3Fe(Cn)_6$, 20 mM $K_4Fe(Cn)_6$ $3H_2O$, 1 mM $MgCl_2$, and 1 mg/ml X-gal (5-bromo-4-chloro-3-indoyl-β-D-galactopyranoside) until a suitable color developed, usually after about 6–12 hr.

Fragmented DNA was extracted from approximately $10^7$ cells transfected with either pCMVN5 or pCMV in 10 mM Tris-HCl (pH 8.0), 10 mM EDTA, 0.5% Triton X-100. The lysate was clarified by centrifugation and the cleared lysate treated with RNase A (50 µg/ml) for one hour at 37° C. This was followed by proteinase K treatment (100 µg/ml) in 0.5% SDS for two hours at 50° C. The DNA solution was extracted with phenol/chloroform and DNA precipitated in EtOH. DNA was dissolved in TE in preparation for electrophoresis on a 1.8% agarose gel. DNA fragmentation was also assayed following transfection with the indicated expression vectors by labeling free DNA ends with terminal deoxytransferase (TUNEL). Cells were collected by trypsin-EDTA treatment, washed two times with PBS, and stained by TUNEL using the APO-DIRECT kit (Phenix Flow Systems, Inc) according to manufacture's directions. FACS analysis was performed on FACSCalibur instrument (Becton Dickinson).

Clonogenicity assays were performed by transfection of 10 µg of the indicated plasmid along with 3 µg of pEGFP-C1 (Clontech). One day following transfection, cells were examined by fluorescence microscopy for GFP positive cells to make sure that transfection has been successful. Transfection of pCMVN5 typically gave 30–50% of the GFP positive cells that were observed with pCMV. Cultures were then incubated an additional 2 weeks in the presence of 500 µg/ml G418 (Sigma). Following G418 selection, the number of GFP positive colonies with greater than 20 cells were determined per 100× microscope field under fluorescence microscopy.

To assess the effects of N5 death domain mutants on sensitivity to ionizing radiation, SAOS-2 (SD8) cells, a sub-line of SAOS-2 cells, were transfected as above with the death domain mutant expression vectors and pEGFP-C1. One day following transfection, viable successfully transfected cells were collected by FACS (Becton Dickenson FACS Vantage) based on GFP fluroescence and 7000 cells plated per well of a 96 well plate. The following day, cells were treated with 0 or 20 Gy radiation from a Nasatron $^{137}Cs$ irradiator. Two days following irradiation, the relative number of remaining viable cells was determined by XTT assay according to manufacturers instructions (Boehringer Mannheim). The data are presented as the ratio of the $OD_{490}$ of treated versus untreated cells.

Microinjection

The N5 GST fusion protein was produced as described by Durfee et al. (1994). The fusion protein was eluted in PBS plus 5 mM glutathione and then dialyzed against 25 mM Tris pH 7.2, 25 mM KCl, 2% glycerol in preparation for injection. The p110Rb and p56Rb were produced and purified as described by Connell-Crowley et al. (1997). The protein concentration of the injected samples is indicated by FIG. 5C. Injection was performed directly on cells growing on 35 mm culture dishes using an Eppendorf micromanipulator with femtotip capillary micropipettes. The injection pressure used was between 50–100 hPa with an injection time of 0.3–0.5 s. Apoptotic cells were detected 90 minutes after injection by observation of characteristic morphological changes under phase contrast microscopy and by staining with the DNA binding fluorochrome bis-(benzimide)-trihydrochloride (Hoechst 33342; Sigma) and fluorescent microscopy as described previously (Ormerod et al., 1993).

Western Blotting

Transfected or treated cells were extracted in a buffer containing 50 mM Tris, pH 7.4, 250 mM NaCl, 5 mM EDTA, 0.1% NP-40, 50 mM NaF, 1 mM PMSF, 1 µg/ml leupeptin on ice for 10 min. Cell debris was pelleted by microcentrifugation and the total protein concentration of the soluble extract determined by Bradford assay according to manufacturers instructions (BioRad). 70 µg of total soluble protein for each sample was loaded on 10% SDS-polyacrylamide gel. After electrophoresis, the proteins were transferred to nitrocellulose and the blot blocked with a solution of 10% dried milk powder in TTBS (100 mM Tris pH 7.5, 150 mM NaCl, 0.1% Tween 20) for 1 hour at room temperature. The blot was incubated with primary antibody diluted in fresh TTBS for 1 hour at room temperature or 4° C. overnight. Primary antibody was detected using a peroxidase-conjugated secondary antibody and Enhanced Chemiluminescence (ECL) as described by the manufacturer (Amersham Life Science).

Immunofluorescent Staining

SAOS-2 cells were seeded onto chamber slides 2 days before irradiation. Cells were irradiated with the indicated dose of γ-irradiation and incubation continued three days before fixation in 100% ice-cold MeOH. Fixed cells were washed in PBS and blocked with TTBS+5% dry milk. Fixed cells were incubated with primary antibody diluted in TTBS for 1 hour at room temperature. After washing, cells were incubated with FITC conjugated secondary antibody (Vector Labs) diluted in TTBS+1 µg/ml Hoechst 33342. After washing, slides were mounted with Vectashield (Vector Labs) before photography under fluorescence microscopy.

Example 2

Overexpression of p84N5 Induces Cell Death by Apoptosis

Figure 1B:
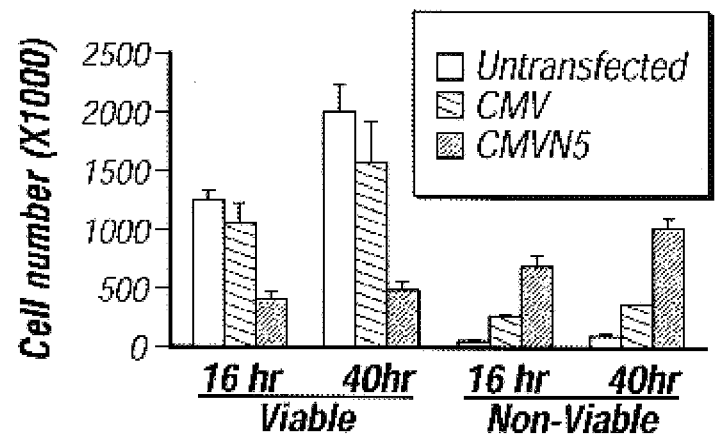
Figure 1C:
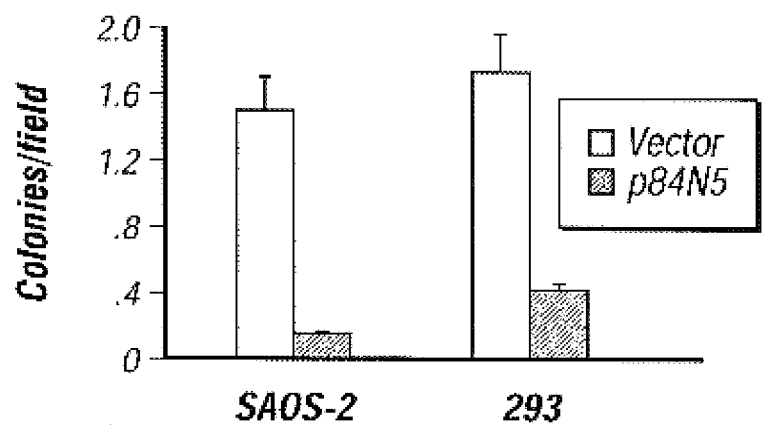

To ascertain whether forced, ectopic or overexpression of p84N5 affected cell viability, full length N5 cDNA was placed under the control of the human cytomegalovirus immediate-early gene promoter (pCMVN5) and transfected into SAOS-2 osteosarcoma cells. Transfection of pCMVN5 reproducibly resulted in fewer surviving cells at 16 and 40 hours following transfection (FIG. 1A) compared to transfection with empty vector (pCMV). Cells were collected at 0 and 24 hours following transfection and cell viability was determined by trypan blue staining. Relative to SAOS-2 cells transfected with pCMV, cells transfected with pCMVN5 had increased numbers of non-viable cells and decreased numbers of viable cells (FIG. 1B). The growth potential of SAOS-2 cells successfully transfected with pCMVN5, as measured by clonogenicity, was also severely compromised. The clonogenicity of cells cotransfected with pCMVN5 and the G418-selectable vector pEGFP-C1 was nearly 10-fold lower than cells cotransfected with pCMV and pEGFP-C1 (FIG. 1C). Transfection into 293 embryonal kidney cells gave similar results. Cells co-transfected with pCMVN5 and pEGFP-C1 had approximately 5-fold fewer colonies after G418 selection than cells transfected with pCMV and pEGFP-C1. Loss of viability was also observed upon pCMVN5 transfection in 5637 bladder carcinoma cells. Loss of viability upon p84N5 expression was not, therefore, cell line specific.

Figure 1D:
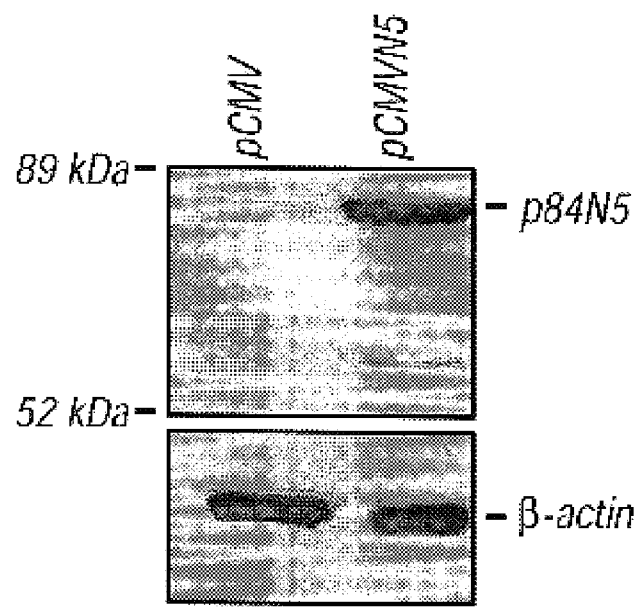

To confirm that loss of cell viability was due to p84N5 over-expression, lysates prepared from transfected 293 cells were analyzed for p84N5 by western blotting using the mouse anti-N5 monoclonal antibody SE10 (Durfee et al., 1994). The antibody recognized two proteins of 84 kDa and 58 kDa apparent molecular mass in several cell lines. Increased expression of both proteins was observed in cells transfected with pCMVN5 relative to transfection with pCMV alone (FIG. 1D). Further, p84N5 was confined primarily to the nucleus as determined by immunofluorescent staining of transfected cells with the anti-N5 monoclonal antibody and expression of a near full-length GFPN5. fusion protein. Since an increase in both proteins was observed upon transfection of pCMVN5, both the 84 kDa and the 58 kDa anti-N5 immuno-reactive proteins were likely derived from expression of the N5 gene. Further, pCMVN5 utilized an intron-less cDNA, indicating that the 58 kDa form of the protein was not generated as a result of alternative splicing.

Figure 2A:
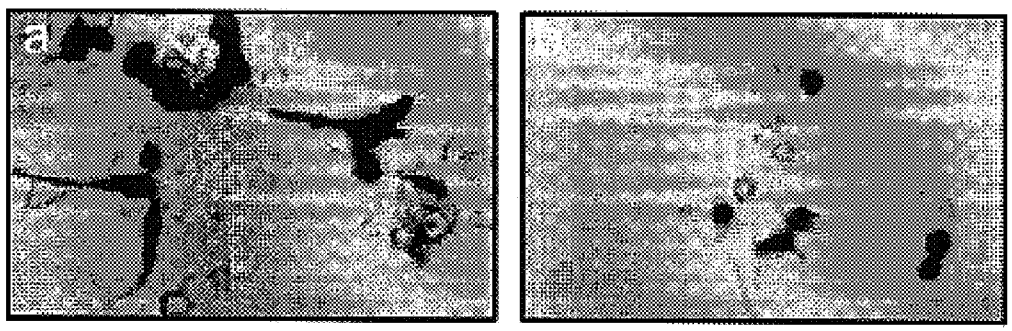
FIG. 2A, FIG. 2B and FIG. 2C. Overexpression of p84N5 induces apoptosis.

To examine the morphology of transfected cells, 293 cells were co-transfected with a β-galactosidase expression vector and pCMVN5 or pCMV. Twenty-four hours after transfection, adherent cells were stained for the presence of β-galactosidase with X-Gal. As expected, the number of surviving β-galactosidase positive cells was significantly lower in pCMVN5 transfected cells than in cells transfected with pCMV. Of the few surviving pCMVN5-transfected, β-galactosidase positive cells, a large proportion exhibited the condensed morphology typical of apoptotic cells (FIG. 2A). In contrast, transfection with pCMV did not alter the morphology of β-galactosidase positive cells.

Figure 2B:
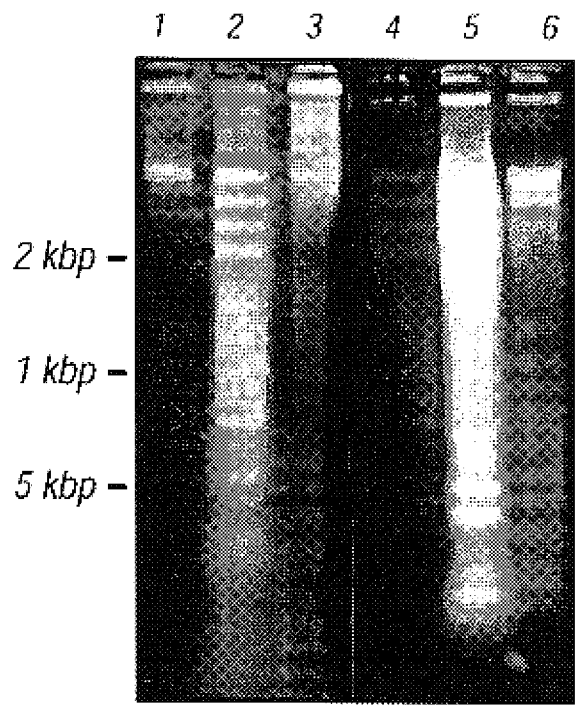
Figure 2C:
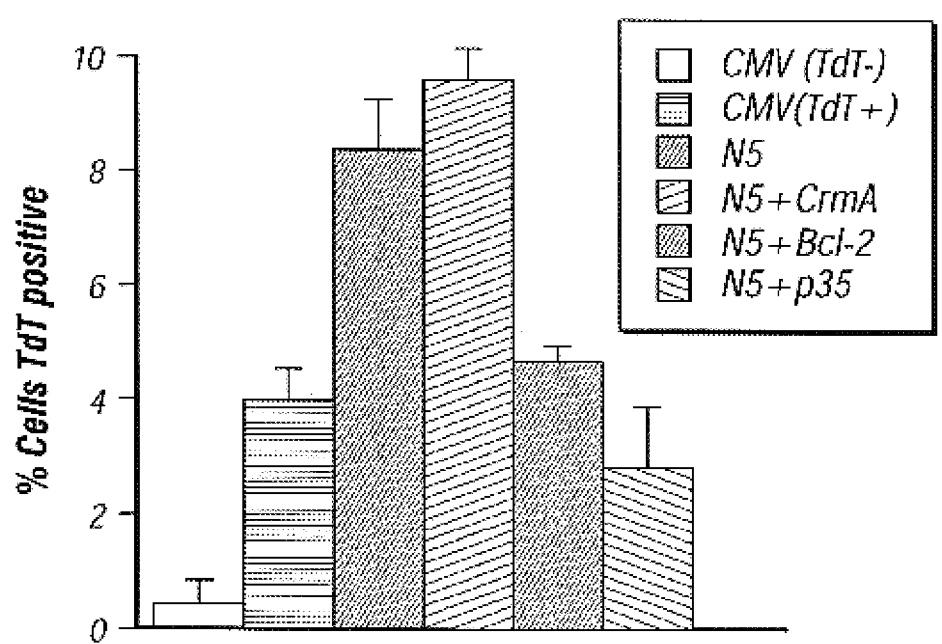

Since the morphology of pCMVN5 transfected cells was consistent with that of cells undergoing apoptosis, the inventors assayed transfected cells for internucleosomal fragmentation of nuclear DNA. SAOS-2 and 5637 cells transfected with pCMVN5 or pCMV were analyzed for internucleosomal DNA fragmentation by gel electrophoresis. DNA laddering similar to that observed in cells treated with staurosporine, a well-characterized apoptotic trigger, was detected in both SAOS-2 and 5637 cells transfected with pCMVN5 (FIG. 2B). Typically about 10% of viable SAOS-2 or 5637 cells remaining at the time of harvest were successfully transfected so the amount of fragmented DNA was lower in transfected cells than in the cells uniformly undergoing apoptosis upon staurosporine treatment. DNA laddering was not detected in cells transfected with pCMV. DNA fragmentation was also analyzed in transfected SAOS-2 cells by terminal deoxynucleotidyl transferase-mediated end labeling (TUNEL). As expected, a significant increase in the percentage of cells with labeled DNA was observed upon transfection with pCMVN5 while transfection of pCMV did not increase the percentage of labeled cells above untransfected controls (FIG. 2C). Again, non-viable cells, as determined by propidium iodide permeability, were excluded from the analysis. Typically 10% of the remaining cells treated with pCMVN5 were successfully transfected indicating that most of the transfected cells contained fragmented DNA.

Apoptosis is subject to both positive and negative regulation. Negative regulators include members of the Bcl-2 gene family (for review see Kroemer, 1997) and caspase inhibitors (for review see Kidd, 1998). The inventors cotransfected pCMVN5 with a Bcl-2 expression plasmid to determine if p84N5-induced cell death was sensitive to a negative apoptotic regulator. Coexpression of Bcl-2 with p84N5 significantly decreased the percentage of cells exhibiting fragmented DNA as measured by TUNEL relative to cells cotransfected with pCMVN5 and empty vector (FIG. 2C). The percentage of cells containing fragmented DNA upon co-transfection of pCMVN5 and the Bcl-2 plasmid was similar to that of the negative control, pCMV. To test the requirement for caspase activation in p84N5-induced cell death, the inventors co-expressed p35, the broad-spectrum baculovirus caspase inhibitor. Cotransfection of pCMVN5 with a p35 expression plasmid also decreased the percentage of cells exhibiting fragmented DNA relative cells expressing p84N5 alone (FIG. 2C). Interestingly, DNA fragmentation induced by p84N5 was insensitive to co-expression of CrmA, a pox virus caspase inhibitor with narrower specificity. Co-transfection of pCMVN5 with the CrmA expression plasmid gave a similar percentage of cells containing fragmented DNA as transfection of pCMVN5 alone.

Example 3 p84N5 is a Death Domain-containing Protein

Figure 3A:
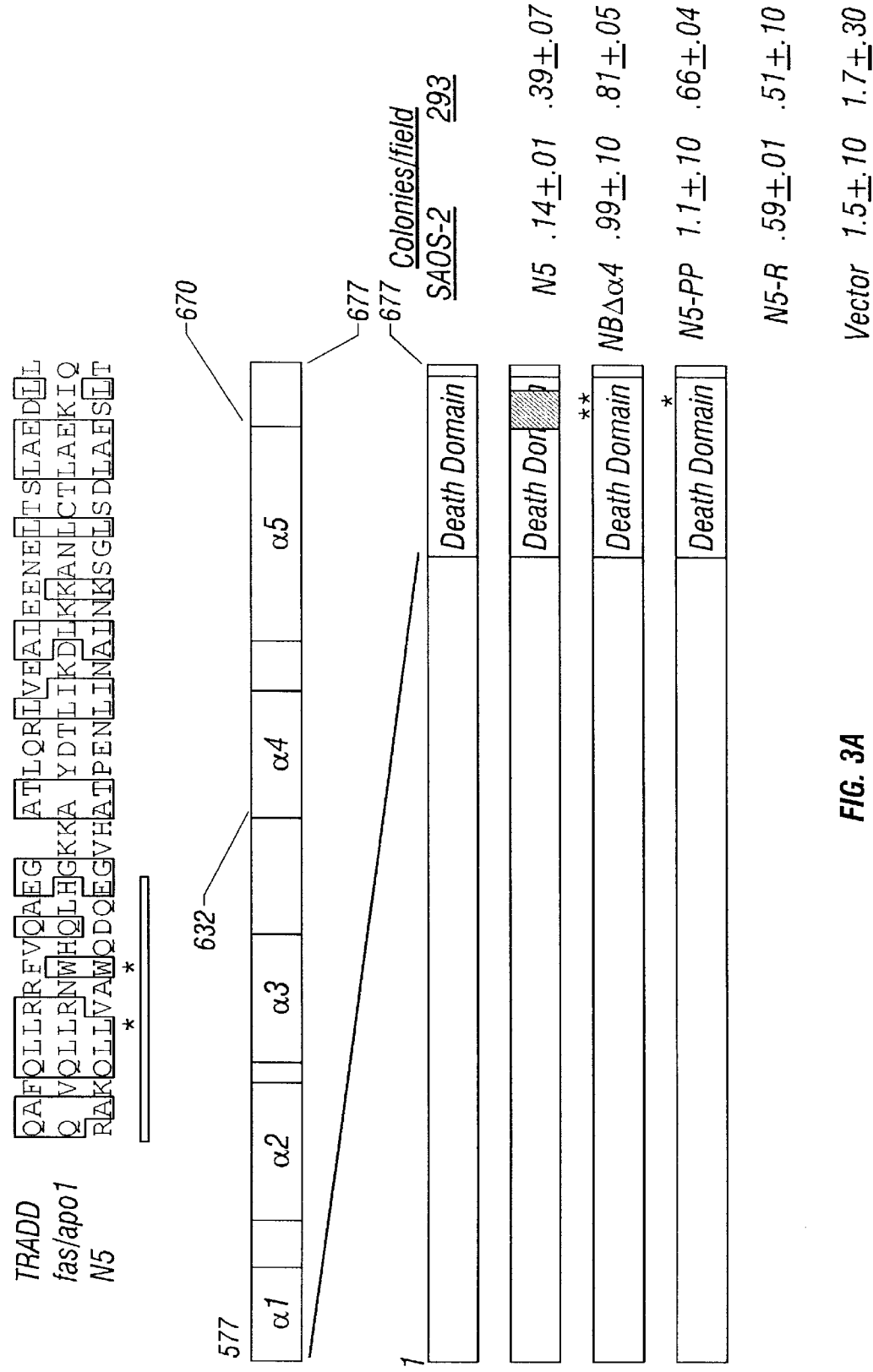
FIG. 3A and FIG. 3B. p84N5 contains a death domain.

N5 protein has a region of statistically significant sequence similarity to the death domain of several proteins involved in apoptosis, including TNFR-1 and fas/apo1 (see FIG. 3A and Feinstein et al., 1995). For example, the p84N5 death domain has 26% amino acid identity in an optimal global alignment with the death domain of RIP, a kinase that interacts with fas/apo1 receptor. The p84N5 death domain has 24% amino acid identity to the TRADD death domain, a protein associated with the TNFR-1. The TRADD and RIP death domains have 24% identity with each other. The death domain is a protein-protein interaction motif required for apoptotic signaling by these proteins. It is composed of 5 sequential alpha helical regions. To the inventors knowledge, none of the currently identified death domain containing proteins involved in apoptosis is localized exclusively to the nucleus. Since p84N5 resides exclusively within the nucleus during interphase (Durfee et al., 1994), the inventors determined that the putative p84N5 death domain is required for function.

Figure 3B:
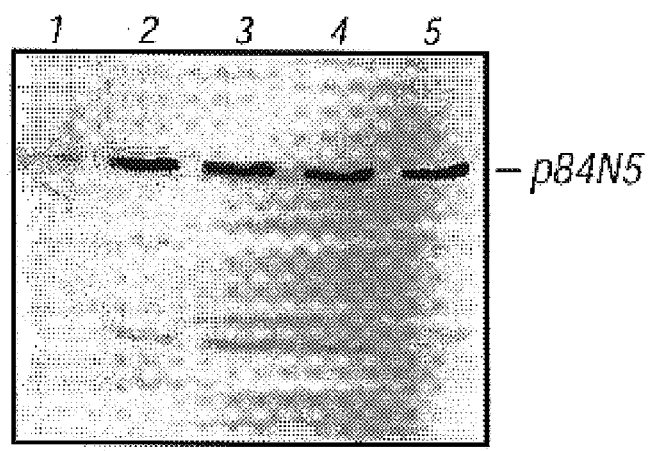

The inventors mutagenized the N5 cDNA to remove the fourth alpha helix or to change certain conserved amino acids within it. Analogous mutations in the TNFR-1 protein compromised its ability to signal cytotoxicity. The pCMVN5-PP mutant substituted prolines for leucine at residue 637 and for tryptophan at residue 640. Another mutant, pCMVN5-R contained an arginine for tryptophan substitution at residue 640. An analogous mutation in TNFR-1 (W378A) compromised its ability to signal cytoxicity (Tartaglia et al., 1993). The pCMVN5Δα4 mutant lacked the 13 amino acids that make up helix 4 in N5. A similar deletion of helix 4 in TNFR-1 inhibited its ability to induce apoptosis. The function of these mutants was tested by analysis of the clonogenicity of transfected cells. Relative to wild-type pCMVN5, pCMVN5Δα4 and pCMVN5-PP had little effect on the clonogenicity of transfected cells (FIG. 3A). Cells transfected with these mutants gave 7 to 8-fold more GFP-positive colonies than were observed with pCMVN5. The clonogenicity of these mutants was close to that of the empty vector pCMV. The pCMVN5-R mutant was also less effective in reducing clonogenicity, generating about 4-fold more GFP-positive colonies than pCMVN5. The inventors analyzed the expression of the mutant proteins to ensure that the decrease in activity was not due to loss of protein expression. Extracts prepared from 293 cells transfected with each of the mutants, as well as pCMVN5, revealed similar levels of protein over-expression (FIG. 3B). All of the mutations created in the death domain, therefore, significantly decreased the specific activity of p84N5.

Example 4

Native p84N5 is Modified During Apoptosis

Figure 4:
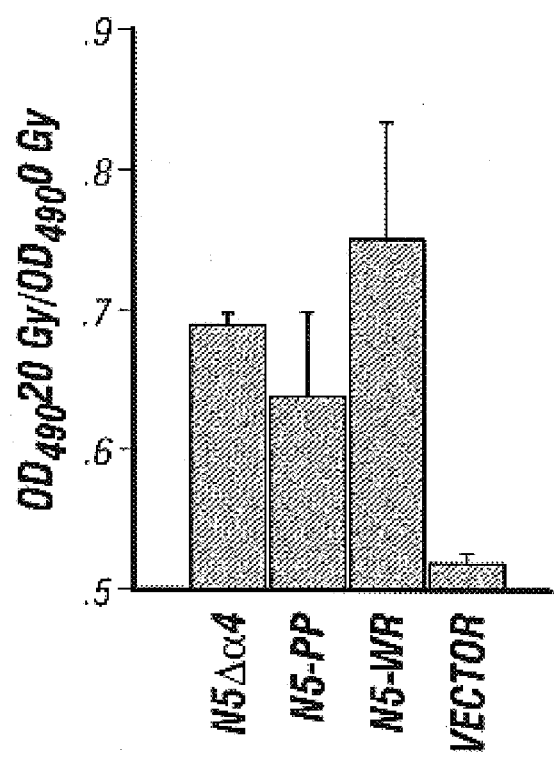
FIG. 4. Expression of N5 death domain mutants interfere with the response of SAOS-2 cells to ionizing radiation. The indicated N5 death domain mutants were transfected into SAOS-2 cells and successfully transfected cells treated with 0 or 20 Gy of γ-radiation. The relative number of viable cells remaining two days later was determined by XTT assay. The results are expressed as the ratio of the $OD_{490}$ of irradiated cells divided by the $OD_{490}$ of untreated cells. The results for each sample are the mean±standard deviation of two independent transfections done in triplicate.

Since p84N5 is constitutively expressed in many cell lines without loss of cell viability, the inventors analyzed whether p84N5 is altered during apoptosis to account for its apparent activation. The inventors examined endogenous p84N5 during apoptosis induced by ionizing radiation or treatment with staurosporine. Expression of endogenous p84N5 was monitored subsequent to treatment by western blotting an equal quantity of total protein extracted from viable, adherent cells or from non-adherent cells. As in Example 1, the anti-p84N5 monoclonal antiserum specifically recognized 84 kDa and 58 kDa immuno-reactive proteins in lysates prepared from untreated cells (0 gray) (FIG. 4A.). In adherent cells treated with 20 Gy the relative level of the full-length 84 kDa protein declined significantly. This was accompanied by the appearance of novel immuno-reactive protein migrating with an apparent molecular mass of approximately 62 kDa. In adherent cells treated with 10 Gy an increase in the 62 kDa protein is detected without a major change in the p84N5 level. Adherent cells treated with 5 Gy showed little change in N5 protein compared to untreated cells. In non-adherent cells the 62 kDa form made up the majority of N5 protein with nearly complete loss of the 84 kDa form at each dose of radiation. However, the 58 kDa form of the protein was still present in these cells. Appearance of the 62 kDa immuno-reactive protein was also detected in cells treated with staurosporine or in cells undergoing spontaneous apoptosis (FIG. 4A, lane S and detached, untreated cells). To ensure equal loading of total cell protein, blots were re-probed for β-actin. The β-actin protein was intact and present in approximately equal concentration in each of the samples. These results indicated that expression of endogenous p84N5 was altered specifically during apoptosis and was accompanied by the appearance of novel forms of N5-related protein with smaller apparent molecular mass. The continued presence of the intact 58 kDa anti-N5 immuno-reactive protein, as well as β-actin, within treated cells demonstrated that loss of p84N5 and was not due to non-specific proteolysis that typically occurs during necrosis or the later stages of apoptosis.

The N5 protein normally has a specific sub-nuclear localization that gives a characteristic punctate nuclear staining pattern (Durfee et al., 1994). The inventors have examined the localization of p84N5 three days following irradiation in an attempt to determine if this localization changes during apoptosis. Irradiated cells are fixed and stained for N5 protein and counter-stained for DNA with Hoechst 33342. In some apoptotic cells with pyknotic nuclear morphology, N5 protein staining is no longer confined exclusively to the nucleus and can be detected throughout the cell. In most cells without overt apoptotic morphology N5 staining is still confined to the nucleus, but is more homogeneous than in the unirradiated controls (FIG. 4B). In none of the unirradiated cells examined can N5 protein staining be detected outside the nucleus. These results suggest that the alteration in p84N5 observed by western blotting is accompanied by a change in sub-nuclear localization. As apoptosis proceeds with attendant changes in gross nuclear morphology, N5 protein can be detected outside of the nucleus.

Example 5

Dominant Interfering Death Domain Mutants Compromise Cellular Responses to Ionizing Radiation Dominant interfering mutants of proteins like Fas or TRADD were created by subtle mutations within their death domains (Vaishnaw, et al. 1999; Park & Baichwal 1996). Presumably these mutations blocked transmission of the death signal but permitted other normal protein-protein interactions. The inventors tested the ability of the N5 death domain mutants to interfere with cellular responses to ionizing radiation. Treatment of SAOS-2 cells with γ radiation caused a transient G2/M cell cycle arrest and subsequent apoptosis (Haas-Kogan et al., 1995). Since expression of Rb inhibited this process, it was possible that dominant interfering N5 mutants would have similar effect. Equal numbers of cells successfully transfected with each of the mutants and a GFP expression plasmid were collected by FACS and either irradiated or left untreated. Two days later the number of remaining viable cells in treated versus untreated cells was compared by XTT assay. In vector control transfected cells, the number of viable cells in the irradiated sample was about half of the untreated sample which was consistent with the normal response of SAOS-2 cells to γ-radiation (Haas-Kogan et al., 1995). Cells transfected with the N5 mutants, however, had a greater number of surviving cells in the irradiated sample relative to the untreated sample, ranging from 64% to 75%. Like Rb, therefore, expression of N5 death domain mutant proteins inhibited the normal response of SAOS-2 cells to radiation.

Example 6

Association with Rb Protein Inhibits p84N5-induced Apoptosis

Figure 5A:
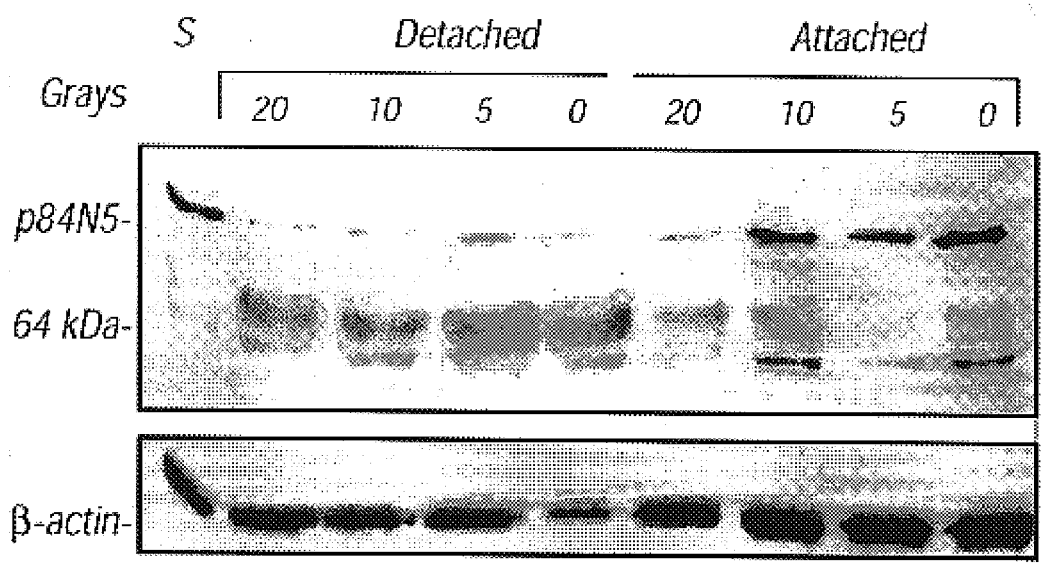
FIG. 5A and FIG. 5B. The structure and sub-cellular localization of endogenous p84N5 is altered during apoptosis.
Figure 5B:
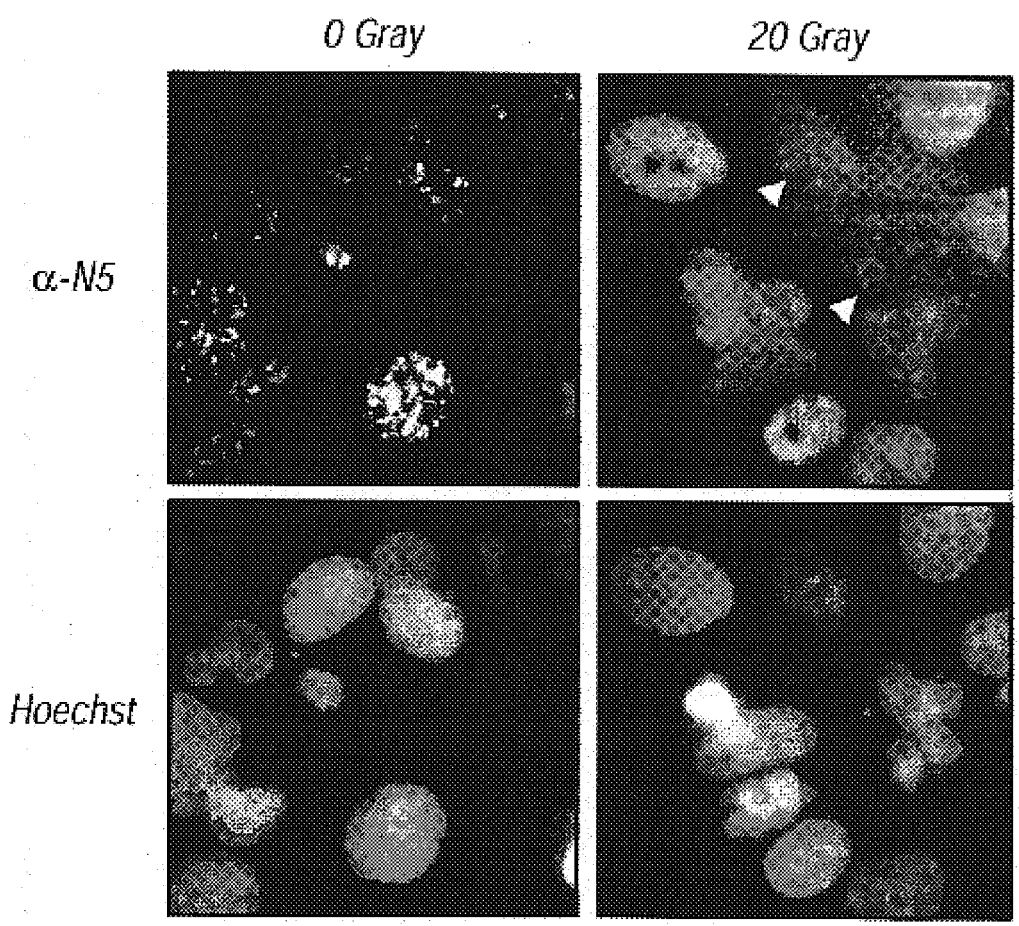
Figure 6A:
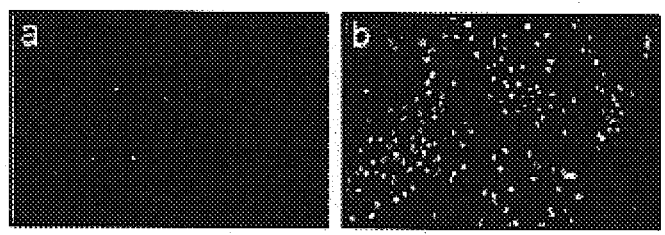
FIG. 6A, FIG. 6B, FIG. 6C and FIG. 6D. Association with Rb inhibits p84N5-induced apoptosis.
Figure 6B:
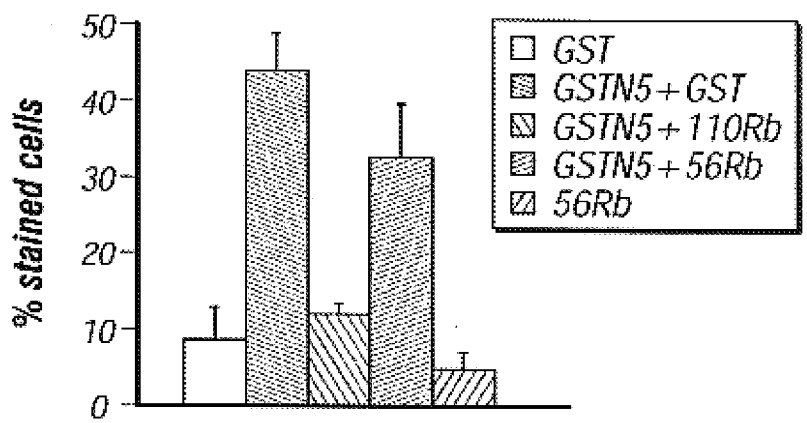
Figure 6C:
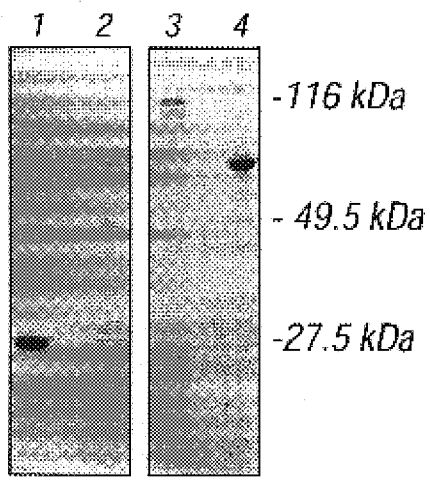
Figure 6D:
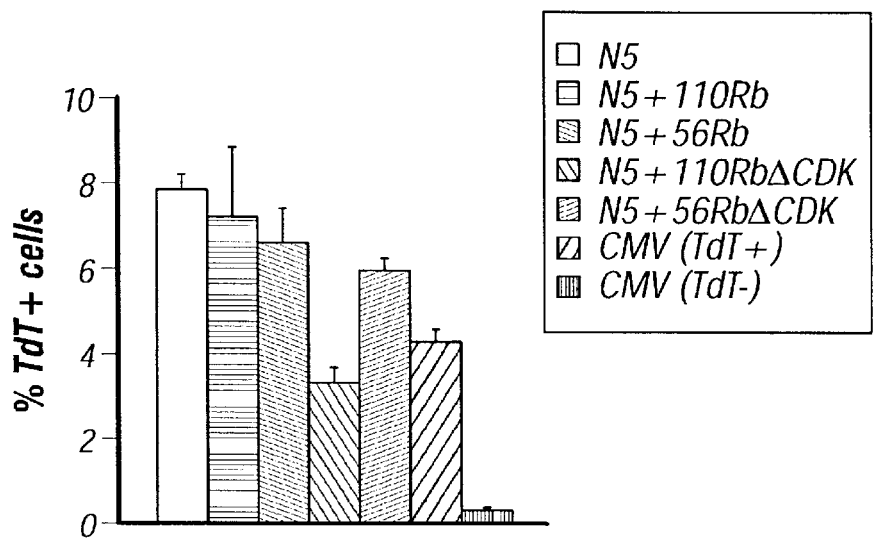

Previous studies demonstrated that p84N5 binds to hypo-phosphorylated forms of p110Rb both in vivo and in vitro (Durfee et al., 1994). A domain within the N-terminal half of p110Rb was necessary and sufficient for efficient binding. To test whether p110Rb influences p84N5-induced apoptosis, an N5 GST (GSTN5) fusion protein was mixed with purified p110Rb and microinjected into SAOS-2 cells (FIG. 5C). The GSTN5 protein contained the C-terminal half of p84N5, including residues that are both necessary and sufficient for binding p110Rb in vitro (Durfee et al., 1994). Apoptosis was measured 90 minutes post-injection by observation of apoptotic morphology and an increase in permeability to low concentrations of the DNA-binding fluorochrome, Hoechst 33342 (Ormerod et al., 1993). Injection of GSTN5 results in a large increase in cells with condensed, brightly stained nuclei relative to cells injected with GST (FIG. 5A). Increased permeability to Hoechst 33342 and altered morphology are characteristic of the early stages of apoptosis. Coinjection of p110Rb with GSTN5 reduced the percentage of cells with bright nuclear staining to that of the negative control, GST (FIG. 5B). Mixing GSTN5 with GST had no effect on the percentage of apoptotic cells typically seen upon microinjection of GSTN5 alone.

Rb protein may inhibit GSTN5 directly or it may influence GSTN5 indirectly through Rb-mediated changes in the cell cycle or transcription. To distinguish between these two possibilities, GSTN5 was coinjected with an N-terminal truncated form of Rb protein (p56Rb). The p56Rb lacks residues required for p84N5 binding (Durfee et al., 1994), yet is capable of regulating cell cycle progression (Goodrich et al., 1991) and binding most of the other cellular proteins with which p110Rb normally interacts. Mixing p56Rb with GSTN5 had no effect on the percentage of brightly stained cells typically observed upon injection GSTN5 alone or with GST (FIG. 5B).

To ensure that the effects of Rb protein observed were not specific for the truncated N5 fusion protein used or for the microinjection assay, the inventors tested the effects of cotransfection of Rb expression plasmids on pCMVN5-induced apoptosis. Coexpression of wild-type p110Rb with p84N5 had a small effect on the proportion of cells undergoing DNA fragmentation that is observed upon expression of p84N5 alone (FIG. 5D). However, a form of p110Rb containing alanine substitutions at 14 consensus CDK phosphorylation sites significantly reduced the percentage of cells containing fragmented DNA. This mutant p110Rb is constitutively active since it is resistant to negative regulation by phosphorylation. Consistent with the microinjection experiments, expression of a phosphorylation-resistant form of p56Rb did not affect the percentage of cells exhibiting p84N5-induced DNA fragmentation.

Discussion

This application demonstrates that overexpression of p84N5 induces apoptotic cell death. This conclusion is based on the observation that loss of cell viability upon expression of p84N5 is accompanied by changes in cellular morphology and internucleosomal DNA fragmentation that are characteristic of apoptotic cells. Further, the inventors demonstrate that some, but not all, naturally occurring inhibitors of apoptosis suppress p84N5-induced apoptosis. Apoptosis induced by p84N5 does not require p53 as indicated by the fact that p53-negative SAOS-2 cells (Chandar et al., 1992) are susceptible to p84N5-induced death.

Although the physiological role of p84N5 is unknown, several observations suggest that it may normally function in the regulation of apoptosis. For example, the N5 cDNA contains a region with statistically significant sequence similarity to the death domain of several proteins involved in apoptotic signaling (Feinstein et al., 1995). Since several proteins with no known role in cell death also contain death domains, this fact alone is not sufficient to suggest apoptotic function. However, the inventors demonstrate that expression of p84N5 can induce apoptosis and that this function is dependent on an intact death domain. Analogous mutations in helix 4 of the p84N5 and the TNFR-1 death domains (W640P or R for N5; W378A for TNFR-1) compromise the ability of these proteins to induce apoptotic cell death. N5 protein, therefore, likely has a death domain that may function like those in other well-characterized death domain proteins.

In addition, the inventors demonstrate that expression of endogenous p84N5 is altered during apoptosis triggered by ionizing radiation. Loss of p84N5 is accompanied by accumulation of N5 protein with an increased electrophoretic mobility. This alteration is coincident with a change in the sub-nuclear localization of N5 protein. Although further work is required to determine the mechanism of p84N5 alteration, the inventors observation is reminiscent of caspase-mediated proteolysis of proteins, such as PARP (Lazebnik et al., 1994) or DFF (Liu et al., 1997), that occur specifically during apoptosis.

Based on caspase substrate specificity as determined by Talanian et al. (1997), several potential caspase cleavage sites exist within p84N5. For example, $DVLD^{102}$ of p84N5 is a near optimum caspase 2, 3, or 7 substrate. The inventors also demonstrate that some apoptotic inhibitors (Bcl-2 and p35) inhibit p84N5-induced apoptosis, but not others (CrmA). This observation demonstrates that p84N5 expression does not result in non-specific cell toxicity, but rather activates a specific apoptotic pathway. Other physiological triggers of apoptosis activate similar pathways since they show a similar sensitivity profile to inhibitors. For example, apoptosis triggered by ionizing radiation is sensitive to Bcl-2 and p35, but not to CrmA (Datta et al., 1997).

Finally, the inventors show that expression of death domain mutants of N5 interfere with the normal response of SAOS-2 cells to ionizing radiation. This suggests that subtle alteration of the N5 death domain creates dominant interfering mutants. Similar effects have been observed in other death domain proteins like Fas or TRADD (Vaishnaw, et al. 1999; Park & Baichwal 1996). All of these findings suggest that p84N5 normally plays a role in the regulation of apoptosis.

The mechanisms cells utilize to generate and transduce apoptotic within the nucleus are not well characterized. Other nuclear proteins such as PML and the CAG repeat proteins (Huntingtin, Ataxin-1, etc.) initiate apoptotic cell death by novel mechanisms (Saudou et al., 1998: Quignon et al., 1998; Klement et al., 1998). How the apoptotic signals initiated by these proteins are transduced to the apoptotic machinery is unknown. N5 protein is unique among proteins that trigger apoptosis from within the nucleus in containing a death domain. Hence, N5 could provide a physical link between apoptotic signals generated within the nucleus and the apoptotic machinery if its death domain functions like other death domain proteins involved in apoptosis. By analogy to TNF or Fas ligand signaling, N5 could potentially recruit death domain adaptor molecules to a complex that ultimately leads to caspase activation.

The N5 protein is expressed constitutively in several cell lines that have been analyzed. Constitutive expression of p84N5 is, at first glance, paradoxical given our finding that forced p84N5 expression induces apoptotic cell death. Several proteins important for the signaling and execution of apoptosis, however, are also constitutively expressed in cells. These proteins typically are activated by post-translational modification during apoptosis. For example, caspases are constitutively expressed as relatively inactive proenzymes that are activated by proteolysis (for review see Kidd, 1998). Numerous other important mediators of apoptosis also are activated by proteolysis including DFF (Liu et al., 1997), Bid (Luo et al., 1998), and sterol regulatory element binding proteins (Wang et al., 1996) among others.

The inventors propose that p84N5 also is activated by post-translational modification. Like ectopic expression of caspases, ectopic p84N5 expression would increase the amount of activated protein above a threshold necessary for triggering apoptosis. The inventors suspect that the N5-related proteins with altered electrophoretic mobility generated during transfection or irradiation may represent activated forms of N5 protein.

Rb protein associates with over sixty different cellular proteins and association with various subsets of these proteins mediates its functions. Most of these proteins utilize domains within the C-terminal half of p110Rb, collectively termed the "large pocket," for binding. The large pocket is sufficient to mediate many of the well-studied functions of p110Rb including regulation of the cell cycle or transcription. The Rb domains required for inhibition of apoptosis have not been defined. N-terminal domains of p110Rb are required to rescue the excessive apoptosis observed upon genetic loss of Rb in the mouse (Riley et al., 1997), suggesting that this domain may be required for inhibition of apoptosis in the affected tissues. A related question is whether the effect of Rb on apoptosis is an indirect consequence of its other established effects on the cell cycle. Data in this application demonstrates that one mechanism utilized by Rb to influence apoptosis is through functional association with p84N5. Coexpression of p110Rb inhibits p84N5-induced apoptosis. In addition, inhibition of p84N5-induced apoptosis correlates with the ability of p110Rb to bind p84N5. N-terminally truncated forms of Rb lacking sequences required for p84N5 binding, yet containing an intact large pocket, do not effectively inhibit p84N5-induced apoptosis. Further, phosphorylation resistant forms of p110Rb are more effective in inhibiting p84N5 than phosphorylation sensitive forms. Phosphorylation also inhibits p84N5/p110Rb complex formation (Durfee et al., 1994). These findings are consistent with the hypothesis that Rb has a direct effect on apoptosis that is independent of its ability to regulate the cell cycle. In addition, these observations identify a novel function for the N-terminal half of p110Rb since it is required for physical association with p84N5. This conclusion may explain, at least in part, the requirement for N-terminal p110Rb domains for rescuing apoptotic defects in mouse embryos lacking wild-type Rb. None of the other proteins that require the N-terminal half of p110Rb for binding has an established role in regulating apoptosis.

Example 7

Construct Recombinant Adenovirus Designed to Express Various Forms of p84N5

Materials and Methods

Cell Culture

All cell lines were obtained from the American Type Culture Collection. Cells were maintained in Dulbecco's modified Eagle's medium with 10% heat-inactivated fetal bovine serum and antibiotics (100 units/ml penicillin, 100 μg/ml streptomycin), in a 5% $CO_2$ incubator at 37° C.

Adenovirus Construction

The full-length N5 cDNA was subcloned into the pAdCMV(AS)-BGHpa vector. This plasmid was co-electroporated with pJM17, the adenovirus backbone plasmid, into 293 cells and recombinant N5 adenovirus (AdN5) identified by PCR using primers specific for N5 essentially as described (Zhang et al., 1993). The resulting AdN5 was a modified serotype 5, E1 deleted adenovirus with p84N5 expression under control of the cytomegalovirus early promoter and bovine growth hormone polyadenylation signal. Recombinant adenovirus stocks were purified by CsCl equilibrium density gradient centrifugation as described (Huyghe et al., 1995). Viral particle numbers were estimated by absorbance at 260 nm in the presence of SDS and infectious titer was determined by an end point assay using the Adenovirus Direct Immunofluorescence kit according to manufacturer recommendations (Chemicon International, Inc.). A GFP expressing adenovirus (AdGFP) is used as a control for virus infection in the studies. Infections were carried out by addition of virus to cultures in DMEM. The cells were incubated at 37° C. for 1 hr with constant agitation at which time complete media was added and cells incubated at 37° C. for the desired length of time.

Results

Recombinant adenovirus have proved to be one viable delivery vehicle for gene therapy (Roth, 1998; Descamps et al., 1996). The inventors have generated recombinant adenovirus designed to express wild-type p84N5. In collaboration with an ongoing structure-function study of N5, the inventors propose to construct three additional recombinant adenovirus designed to express mutant forms of p84N5. The N5 sequences required for binding pRb have not been defined. Once these sequences are defined, recombinant adenovirus designed to express a pRb binding defective N5 protein will be constructed. Since pRb inhibits p84N5-induced apoptosis, this virus may be more efficient in killing cells that express functional pRb. The microinjection data suggest that the C-terminal half of p84N5 is sufficient for triggering apoptosis. The inventors also have preliminary evidence that p84N5 is modified by proteolysis to a smaller protein during apoptosis (FIG. 4B). It is possible that the smaller modified form of p84N5 is the active form for inducing apoptosis. If so, then the truncated p84N5 may be more efficient at inducing apoptosis than wild-type p84N5. The inventors will also construct a recombinant adenovirus designed to express an N-terminally truncated p84N5. The nuclear localization signal for p84N5 is contained within a 400 bp SalI-EcoRI fragment of the N5 cDNA. Once the nuclear localization signal within this fragment is defined, a recombinant adenovirus will be made to express a mutant p84N5 that does not localize to the nucleus. Although it is unclear whether nuclear localization is required for p84N5-induced apoptosis, based on preliminary data altered localization may facilitate induction of apoptosis by p84N5 (FIG. 4A). The current targeting vector places the N5 cDNA under control of the strong cytomegalovirus early promoter. It may be advantageous under certain circumstances to reduce the level of transgene expression. For example, high p84N5 expression may reduce the potential selectivity of cell death to pRb negative cells. The inventors will also construct virus from targeting vectors using the weaker SV40 early promoter.

Example 8

Test the Ability of p84N5 Gene Therapy to Inhibit Breast Cancer Cell Growth in vitro Materials and Methods Western Blot Analysis Infected cells were lysed in a buffer containing 50 mM Tris, pH7.4, 250 mM NaCl, 5 mM EDTA, 0.1% NP40, 50 mM NaF, 1 mM PMSF, and 1 ug/ml leupeptin. Samples were kept on ice for 10 minutes followed by centrifugation to pellet insoluble debris. Total protein concentration of the soluble extract was determined by Bradford assay according to manufacturer instructions (Biorad). Seventeen μg of total protein for each sample was resolved by 10% SDS-PAGE and the protein transferred to nitrocellulose membranes. The membranes were blocked with 5% dry milk in PBS and probed with a mouse monoclonal anti-p84N5 antibody or a mouse anti-β-actin monoclonal antibody. The blots were developed by ECL according to manufacturer recommendations (Amersham).

Cell Growth Assay

Cells were plated at a density of $2\times10^4$ cells/ml in 12-well plates in triplicate. Cells were treated with AdN5, AdGFP, or PBS as above. Cells were harvested at the indicated time intervals and viable cells counted using trypan blue and a hemacytometer.

DNA Fragmentation Analysis

Following infection with AdN5 or AdGFP for 5 days, cells were collected and resuspended in 0.1 ml PBS to which 1 ml extraction buffer (10 mM Tris, pH8.0, 100 mM EDTA, 20 µg/ml RNAse, 0.5% SDS) was added before incubation at 37° C. for 1–2 hours. Proteinase K was then added to a final concentration of 100 µg/ml and incubation continued at 50° C. for at least 3 hours. NaCl was added to a final concentration of 1 M and the samples incubated at 4° C. overnight. High molecular weight DNA was pelleted by ultracentrifugation for 1 hour at 57,000 g. The supernatant was extracted once with an equal volume of 0.5M Tris(pH 8.0)-saturated phenol and then again with phenol/chloroform. The DNA was EtOH precipitated and analyzed in a 1% agarose gel.

Results

Adenoviral Infection of Tumor Cell Lines

Figure 7:
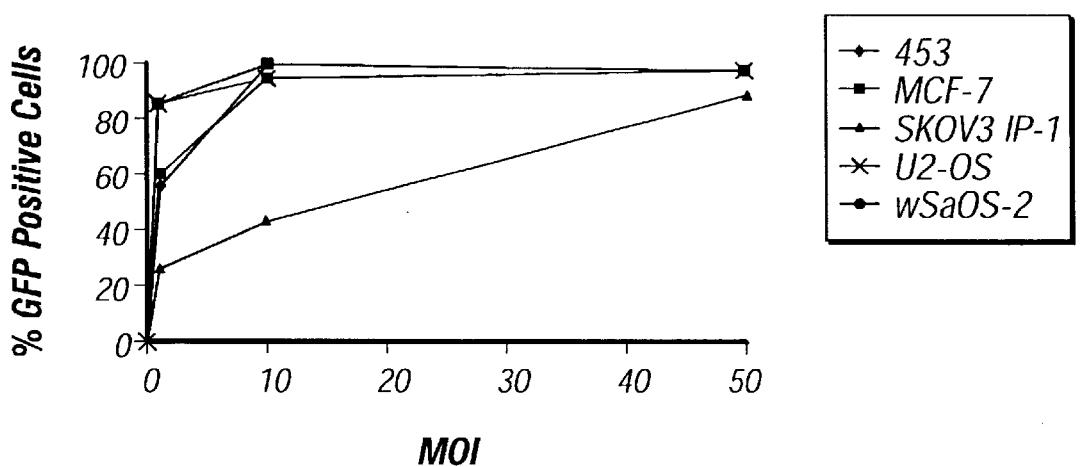
FIG. 7. Efficiency of adenoviral-mediated gene transduction in various cancer cell lines. MDA-MB-453, MCF-7, SKOV3 IP-1, U2OS and SAOS2 cells were treated with AdGFP at MOIs ranging from 1 to 100. The percentage of GFP-positive cells was scored for each sample by fluorescence microscopy. The results presented are the mean of three infections.

Five tumor cell lines were used to study the effects of AdN5 infection, two breast carcinoma lines (MCF-7 and MDA-MB-453), an ovarian carcinoma line (SKOV3 IP-1), and two osteosarcoma cell lines (SAOS-2, U2OS). Each cell line was treated with varying numbers of infectious AdGFP to determine the efficiency of adenoviral gene transduction. The percentage of infected cells was determined the following day by fluorescence microscopy. The efficiency of adenoviral infection was similar in each cell line except for SKOV3 IP-1 (FIG. 7). At a multiplicity of infection (MOI) of 10, greater than 90% of MDA-MB-453, MCF-7, U2OS, or SAOS-2 cells expressed detectable GFP. An MOI of 50 was required to observe similar levels of infection in SKOV3 IP-1 cells. For all subsequent experiments, an MOI of 50 was used to treat SKOV3 IP-1 cells while an MOI of 10 was used to treat the remaining cell lines.

AdN5 Inhibits Tumor Cell Growth by Inducing Apoptosis

Figure 8A:
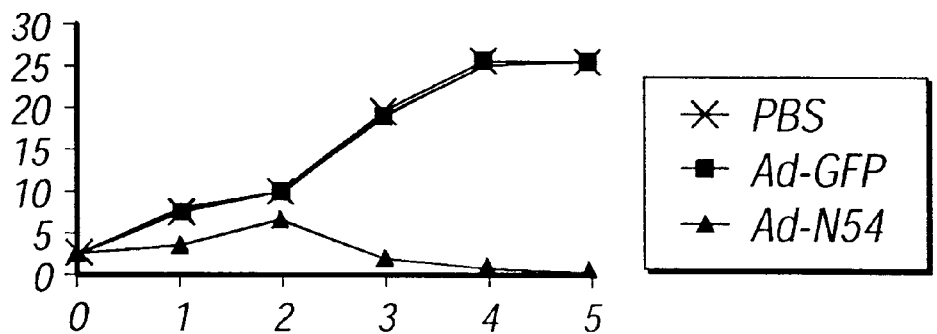
FIG. 8A, FIG. 8B, FIG. 8C, FIG. 8D, FIG. 8E, and FIG. 8F. Expression of p84N5 upon AdN5 infection inhibits tumor cell proliferation in vitro. Equal numbers of MCF-7 (FIG. 8A), MDA-MB-453 (FIG. 8B), U2OS (FIG. 8D), and SAOS2 (FIG. 8E) cells were treated as indicated at an MOI of 10. SKOV3 IP-1 (FIG. 8C) cells were treated at an MOI of 50. Aliquots of the infected cells were harvested at the indicated times and the number of viable cells counted. The data presented are the mean of three infections.
Figure 8B:
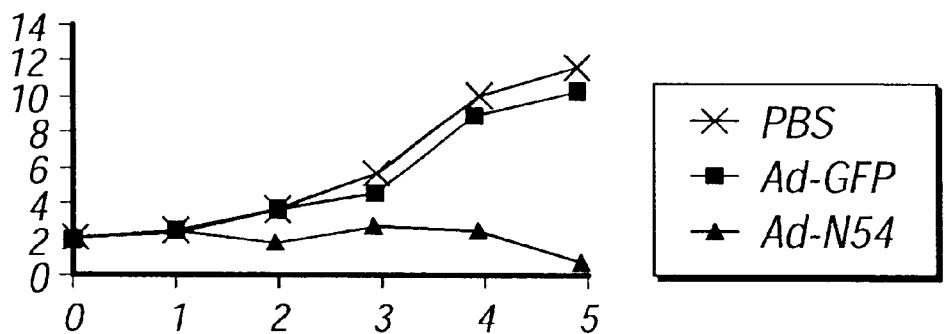
Figure 8C:
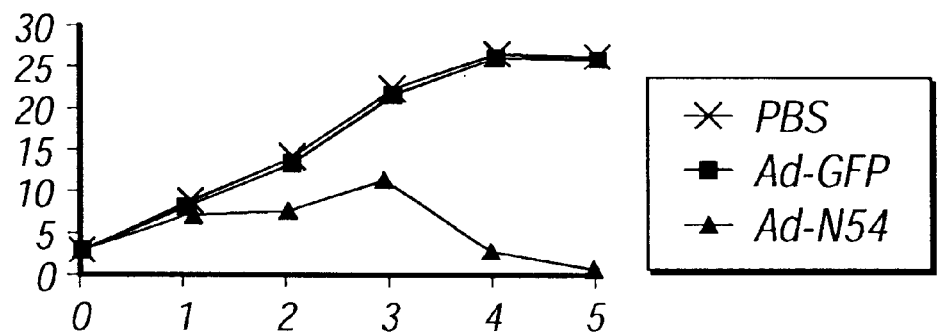
Figure 8D:
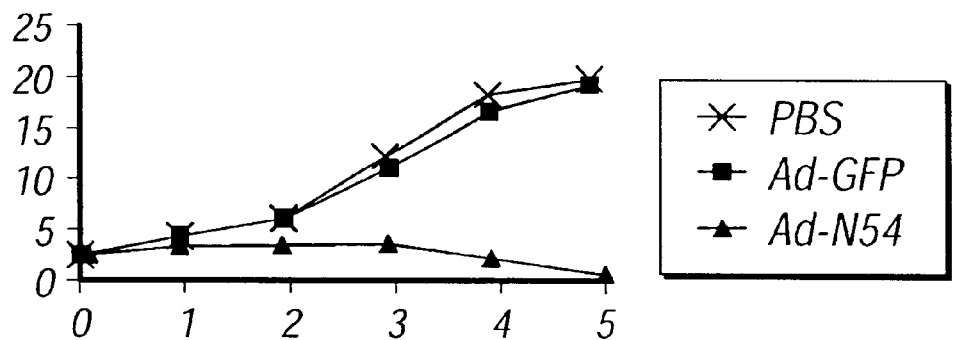
Figure 8E:
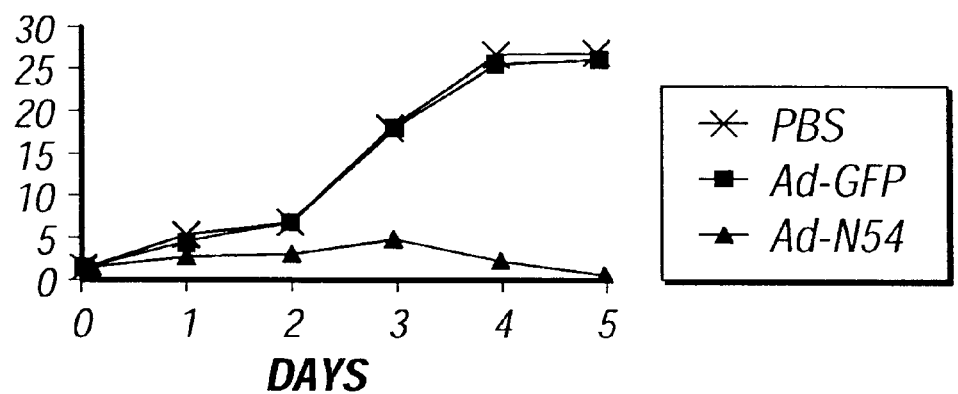
Figure 8F:
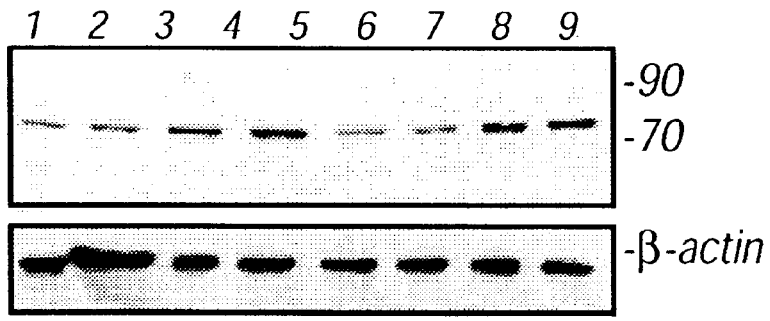

The effect of AdN5 infection on the growth of each cell line in vitro was determined by measuring the proliferation of viable cells after treatment with AdN5, AdGFP, or PBS mock infection. Treatment with AdN5 severely inhibited cell proliferation of each cell line (FIG. 8A–FIG. 8E). Cell numbers remained relatively constant for 3 days and subsequently declined. Treatment of cells with AdGFP had no detectable affect on cell proliferation relative to mock infected cells. To ensure that the effects of AdN5 infection on cell proliferation coincided with increased expression of p84N5, protein extracts of treated SKOV3 IP-1 and U2OS cells were prepared. An equal amount of total cell protein from each sample was resolved by SDS-PAGE, blotted, and the western blots stained with a monoclonal antibody specific for p84N5. Endogenous p84N5 was readily detectable in each cell line treated with PBS or AdGFP (FIG. 8F). The level of p84N5 increased significantly by 24 hours post-infection with AdN5 reaching a maximum by 48 hours post-infection. By 72 hours post-infection, the relative level of p84N5 in AdN5 infected U2OS cells decreased to a level similar to AdGFP treated cells. The morphology of cells infected with AdN5 and the decrease in cell number suggested that AdN5 may inhibit tumor cell growth by induction of apoptosis.

Figure 9:
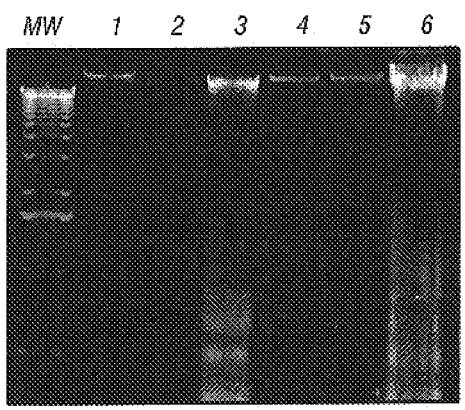
FIG. 9. AdN5 infected cells contain fragmented DNA. SKOV3 IP-1 cells (lanes 1–3) or U2OS cells (lanes 4–6) were treated with PBS (lanes 1 and 4), AdGFP (lanes 2 and 5), or AdN5 (lanes 3 and 6) at MOIs of 50 or 10, respectively. Five days later, cells were collected and analyzed for the presence of fragmented DNA by agarose gel electrophoresis and EtBr staining. A 1 Kbp DNA ladder served as molecular weight marker (MW).

To examine this possibility, DNA was extracted from treated cells and examined for fragmentation by agarose gel electrophoresis. DNA laddering characteristic of cells undergoing apoptosis was observed in AdN5 infected cells but not in cells treated with AdGFP or PBS (FIG. 9). The morphology of AdN5 infected cells was also consistent with induction of apoptosis. Relative to AdGFP infected cells, AdN5 infected cells exhibit a condensed and rounded morphology prior to detaching from the culture dish.

Example 9

Test the Ability of p84N5 Gene Therapy to Inhibit Breast Cancer Cell Growth in vivo Materials and Methods Inhibition of Tumor Growth in Vivo SKOV3 IP-1 cells and U2OS cells were treated with AdN5 or AdGFP at 50 or 20 MOI respectively. An equal number of cells were treated with PBS. Twenty-four hours after infection, the treated cells were harvested and rinsed twice with PBS. For each sample, one million cells in a volume of 0.2 ml PBS were injected subcutaneously into the flanks of nude mice. Tumor formation was evaluated weekly for 5 weeks. At least six mice were injected for each sample. Tumor volumes were estimated by measuring the diameter of the resulting tumors in three dimensions.

Results

AdN5 Inhibits Tumorigenicity of Tumor Cells in Nude Mice

Figure 10A:
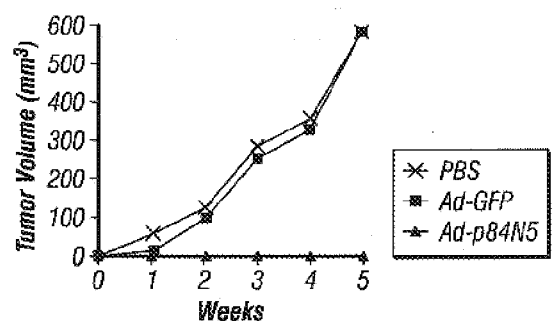
FIG. 10A and FIG. 10B. AdN5 inhibits tumor cell proliferation in vivo.
Figure 10B:

The effect of AdN5 infection on the tumorigenicity of SKOV3 IP-1 and U2OS in nude mice was also examined. Cells were infected with AdN5 or AdGFP prior to subcutaneous injection into nude mice. Both AdGFP and PBS treated SKOV3 IP-1 cells formed large tumors that were readily detectable by two weeks post-injection (FIG. 10A and FIG. 10B). Tumor volume increased exponentially over time. No tumor growth could be detected in cells treated with AdN5 even after 5 weeks. At this time the tumor volume of AdGFP infected cells reached 600 mm$^3$. Similar results were observed in U2OS cells. Tumor volume of AdGFP and PBS treated U2OS cells reached a maximum of 43 mm$^3$ while no tumor growth could be detected in AdN5 infected cells.

Discussion

The present invention demonstrates that adenovirus mediated N5 gene transfer can dramatically inhibit the proliferation and tumorigenicity of several different types of tumor cells. Representative breast and ovarian carcinoma cell lines as well as osteosarcoma cell lines were all sensitive to the effects of AdN5, as shown in Example 8. The inhibition of tumor cell proliferation is mediated by induction of apoptosis as indicated by the presence of fragmented DNA and altered morphology of AdN5 infected cells.

The mechanism of N5-induced cell death is uncharacterized. However, several observations indicate that AdN5 activates an apoptotic pathway that is distinct from those activated by other recombinant adenovirus with similar effect on tumor cells such as Adp53, AdE2F-1, AdPML, or AdFas ligand (Liu et al., 1994; Hunt et al., 1997; Le et al., 1998; Hedlund et al., 1999). For example, the effects of AdN5 are independent of p53 status since MCF-7 and MDA-MB-453 cells differ in p53 status yet are equally susceptible to AdN5. Therefore, AdN5 does not require p53 for its effects, nor is AdN5 inhibited by the presence of wild-type p53. In contrast, cells containing wild-type p53 are less sensitive to Adp53 than cells lacking wild-type p53 (Harris et al., 1996). Further, Adp53 and AdPML infection induces a G1 cell cycle arrest and subsequent apoptosis (Le et al., 1998; Meng et al., 1998) while AdE2F-1 infection induces premature entry into S phase (Agah et al., 1997). Similar changes in cell cycle distribution are not observed in AdN5 infected cells.

Many tumors fail to respond to conventional chemotherapy because tumor cells become resistant to apoptosis that is normally triggered by these agents. Gene therapies designed to efficiently induce apoptosis in such tumor cells may help overcome this problem. N5 based gene therapy for the treatment of tumors may provide several advantages, as demonstrated in the present invention. First, N5 gene transfer efficiently induces apoptosis in a wide variety of cancer cells. The range of tumor cells sensitive to N5 may be greater than other currently characterized genes. MCF-7 breast carcinoma cells are relatively resistant to Adp53 and AdE2F-1 (Harris et al., 1996; Agah et al., 1997) but are sensitive to AdN5. Second, AdN5 likely induces apoptosis by a distinct mechanism. As discussed above, AdN5-induced apoptosis is not influenced by p53 status or cell type. Finally, N5-induced apoptosis is inhibited by co-expression of wild-type Rb. This demonstrates that tumor cells with genetically or functionally inactive Rb may be more susceptible to AdN5 than normal cells that contain active Rb. AdN5 is therefore an important novel gene therapy for patients with a wide variety of cancers.

Example 10
Characterization of p84N5, p16, and pRb Expression in Breast Cancer Cells Tumor cells ultimately bypass normal control of apoptosis and the cell cycle. Inactivation of normal pRb function relieves cells of one major form of cell cycle regulation and such inactivation is frequently observed in breast cancer. However, cells lacking normal pRb function may be more susceptible to p84N5-induced apoptosis. Since this would limit proliferation, tumor cells may evolve means to reduce or eliminate p84N5 expression. If so, p84N5 expression may serve as an informative diagnostic or prognostic indicator. To examine this possibility, the expression and localization of p84N5 during various stages of breast carcinogenesis was examined. Readily available samples of breast carcinoma tissue and grossly normal breast tissue have been collected from approximately 50 mastectomy specimens at M. D. Anderson Cancer Center through the Breast Cancer Program tumor bank. Specimens have been sectioned and stained with H&E for classification as normal, low-grade (well differentiated grades 1 and 2 combined), or high grade (poorly differentiated, grade 3) DCIS and low or high grade invasive cancer by the Department of Pathology (M. D. Anderson Cancer Center). N5 protein expression will be analyzed in these samples by western blotting of extracted protein. One hundred micrograms of total cellular protein from each sample will be resolved by SDS-PAGE, blotted, and stained with the antibodies directed against p84N5, pRb, and p16. Blots will also be stained for β-actin as an internal reference control. Blots will be developed using ECL (Amersham) and the p84N5, pRb, or p16 signal will be scored by densitometry relative to the internal β-actin signal. The data will be statistically analyzed for association between relative expression of p84N5 and histological grade. Statistical analysis of a possible correlation between p16 or pRb expression and p84N5 expression will also be analyzed.

Since flash frozen specimens suitable for protein extraction are limited in number, the inventors will also analyze archival paraffin embedded sections for p84N5 expression. Sections will be selected for immunohistochemical analysis that have tumor and adjacent normal epithelium or DCIS present. These specimens will be analyzed for p84N5, pRb, and p16 expression by immunohistochemistry using a modification of the ABC technique (Xu et al., 1997). Well-characterized antibodies for staining pRb and p16 in paraffin embedded sections are commercially available. The suitability of the N5 monoclonal antibody for use in paraffin embedded sections has not been tested. If this antibody does not perform satisfactorily, the inventors will produce purified rabbit polyclonal anti-N5 antibody for use in these experiments. The inventors have produced a purified GSTN5 fusion protein that will be used to immunize rabbits. Antibody specifically reactive against N5 will be purified from rabbit sera by GSTN5 affinity chromatography. Antibody reactive against the GST moiety of the fusion protein will be removed by GST affinity chromatography. The antibodies will be tested for use by immunohistochemical staining of paraffin embedded sections of MCF7 cell pellets that are known to express p84N5. The results of immunohistochemical staining will be reviewed by two core pathologists. N5 staining in tumor cells will be compared to staining in the adjacent normal tissue to determine if expression is higher, lower, or the same in the tumor cells. Staining of p16 and pRb will be similarly scored. The data will be analyzed as above for possible correlation between p84N5 expression and histological grade, p16 expression, or pRb expression.

Example 11
The Nuclear Death Domain Protein p84N5 Activates a G2/M Cell Cycle Checkpoint Prior to the Onset of Apoptosis The invention also describes mechanisms utilized to transduce nuclear apoptotic signals. Characterizing these mechanisms is important for cancer prognosis and the development of new anticancer treatment regimens as one can then predict tumor response to genotoxic radiation or chemotherapy. The Rb tumor suppressor protein can regulate apoptosis triggered by DNA damage through an unknown mechanism. The nuclear death domain-containing protein p84N5 can induce apoptosis that is inhibited by association with Rb. The pattern of caspase and NF-kB activation during p84N5-induced apoptosis is similar to p53-independent cellular responses to DNA damage. One hallmark of this response is the activation of a G2/M cell cycle checkpoint. Described herein are the effects of p84N5 on the cell cycle. Expression of p84N5 induces changes in cell cycle distribution and kinetics that are consistent with the activation of a G2/M cell cycle checkpoint. This checkpoint is sensitive to caffeine, but is functional in cells from ataxia-telangiectasia patients. Hence, the invention provides that p84N5 induces an ATM-independent, caffeine-sensitive G2/M cell cycle arrest prior to the onset of apoptosis. The current example also describes how p84N5-induced apoptosis is preceded by activation of a p53-independent G2/M checkpoint.

Methods
Cell Culture

SAOS-2, 293, and C-33A cell lines were obtained from American type culture collection and maintained in Dulbecco's modified Eagle's medium with 10% heat-inactivated fetal bovine serum and antibiotics (100 units/ml penicillin, 100 mg/ml streptomycin), in a 5% $CO_2$ incubator at 37° C. The AT22IJE-T cell line and the ATM-expressing derivative were cultured under the same conditions except for the addition of hygromycin as described (Ziv et al., 1997). Viable cells were counted after trypan blue staining using a hemacytometer. Caffeine was added to the culture media to a final concentration of 2 mM.

Plasmids and Adenovirus

The full-length p84N5 cDNA was subcloned into the pCEP4 (Invitrogen, Carlsbad, Calif.) expression vector as previously described (Doostzadeh-Cizeron et al., 1999) to create the expression vector pCMVN5. This plasmid was used to express p84N5 upon calcium-phosphate mediated transfection. The recombinant p84N5 expressing adenovirus (AdN5) was made as previously described (Doostzadeh-Cizeron and Goodrich, 2000; Yin et al., 2000) by cloning the p84N5 cDNA into the pAdCMV (AS)-BGHpa vector. The green fluorescent protein expressing adenovirus (AdGFP) was made similarly and provided by Dr. T. J. Liu (M. D. Anderson Cancer Center). Recombinant adenovirus was purified by CsCl equilibrium density gradient centrifugation and viral particle numbers estimated by OD260 in the presence of SDS as described (Huyghe et al., 1995). Infectious titer was determined by an end point dilution of the viral stock on 293 cells. Viral infections were typically performed by adding an appropriate number of infectious units to cells and incubating under normal growth conditions overnight.

Transfections and Western Blotting

For transfections, 293 cells were seeded on 100-mm dishes and transfected the following day by calcium phosphate precipitation (Wigler et al., 1979) using 10 mg of total DNA. Transfections typically included 1 mg of the pEGFP-C1 plasmid to measure the transfection efficiency the following day under fluorescence microscopy. Transfected cells were extracted in a buffer containing 50 mM Tris, pH 7.4, 250 mM NaCl, 5 mM EDTA, 0.1% NP-40, 50 mM NaF, 1 mM PMSF, 1 mg/ml leupeptin on ice for 10 min. The total protein concentration of the soluble extract was determined by Bradford assay according to manufacturer's instructions (BioRad, Hercules, Calif.). 25 mg of total protein for each sample, normalized for transfection efficiency, was resolved by 10% SDS-PAGE, blotted, and stained as previously described (Doostzadeh-Cizeron and Goodrich, 2000). Antibody directed against p84N5 (Durfee et al., 1994) was described previously. All other antibodies were used as directed by the manufacturer (Santa Cruz Biotechnology, Santa Cruz, Calif.). Primary antibodies were detected using a peroxidase-conjugated secondary antibody and Enhanced Chemiluminescence according to manufacturer's recommendations (Amersham Pharmacia Biotech, Uppsala, Sweden).

Cell Cycle Analysis

Routine analysis of cell cycle distribution was determined by propidium iodide (PI) staining and flow cytometry. Infected cells were harvested by trypsinization, resuspended in growth media, washed once in phosphate-buffered saline (PBS), resuspended in 0.5 ml PBS, and fixed by addition of ice-cold 95% ethanol to 60% while vortexing. Cells were stored in ethanol overnight at −20° C. prior to staining. Cells were then washed in PBS and resuspended in PBS containing 10 mg/ml propidium iodide and 250 mg/ml RNase A. Cells were incubated at 37° C. for 15 minutes prior to flow cytometric analysis using a Coulter EPICS Profile instrument (Beckman Coulter Inc., Fullerton, Calif.). Cell cycle distributions were determined from histograms using Multicycle (Phenix Flow Systems, San Diego, Calif.). For kinetic analysis of the cell cycle, bromodeoxyuridine (BrdU) was added to the culture media at the indicated times after infection. After 20 minutes BrdU media was removed, the cells washed three times with pre-warmed and gassed media, and then either fixed with ethanol as above (time 0) are incubation continued for 6 hours before fixation. After fixation, the cells were prepared for kinetic flow cytometric analysis. Fixed cells were digested in 0.04% pepsin (EM Science, Cherry Hill, N.J.) in 0.1N HCl for 20 min while rocking at room temperature. After incubation with 2N HCl for 20 min at 37° C., 0.1 M sodium borate (twice the HCl volume) was added. The nuclei were then centrifuged and washed with PBS containing 0.5% Tween 20 and 0.5% bovine serum albumin (PBTB). After centrifugation the nuclei were resuspended in anti-BrdU monoclonal antibody IU-4 (1:100 vol/vol, Caltag, South San Francisco, Calif.) in PBS plus 0.5% Tween 20 (PBT) and then incubated at room temperature for 1 h in the dark. Another washing with PBTB followed, and then the nuclei were incubated for 1 h in the dark at room temperature with fluorescein isothiocyanate (FITC)-conjugated goat-antimouse immunoglobulin G (IgG; 1:100 vol/vol; Sigma) in PBT and 1% normal goat serum. After a final wash in PBTB, the nuclei were resuspended in 10 mg/ml PI (Sigma, St. Louis, Mo.) at a concentration of $10_6$ nuclei/ml in PBTB. Bivariate distributions of BrdU content (FITC) versus DNA content (PI) were measured using an Epics 752 flow cytometer (Coulter Corp., Hialeah, Fla.) equipped with narrow-beam (5-mm) excitation optics, a low-velocity quartz flow cell and Cicero data acquisition and display electronics (Cytomation, Fort Collins, Colo.) Excitation was at 488 nm using a 5-W argon-ion laser operating at 200 mW. After blocking incident laser light, BrdU was measured using a logarithmic amplifier with a 530-nm short-pass filter and DNA content collected after a 610-nm long-pass filter. There was no spectral overlap of the emitted fluorescence using this optical configuration. Doublets and clumps were excluded from the analysis by gating on a bivariate distribution of the red peak-vs.-integral signal. Data from 30,000 events.8 were collected in the final gated histograms. Bivariate DNA versus BrdU histograms were analyzed using the "Summit" software (Cytomation) and one-dimensional DNA histograms were fitted using Modfit LT (Verity Software House, Topsham, Me.). The analytical methodology for calculation of kinetic parameters has been described in detail (Terry et al., 1991; White et al., 1990a; White et al., 1990b; Terry and White, 1996, incorporated herein by reference). The analysis is based an established approach to compute cell kinetic parameters using the extra information inherent in a bivariate DNA-vs.-incorporated BrdU flow cytometry histogram together with our more recent method for the simultaneous estimation of the durations of G2 and Mitosis ($_{TG2+}M$), and S-phase ($_TS$), and the potential doubling time ($_{Tpot}$) using single-sample dynamic data from bivariate DNA-thymidine analogue cytometry (White et al., 2000). Labeling index (LI) was measured directly using data taken immediately (20 minutes) after pulse labeling and computed for the 6 hour time points from $LI=e^{c(TG2+M)}(e^v-1)$ where c is the growth rate of the population and v is a dimensionless quantity based on the division status of labeled cells, which may be measured from these labeled populations (White et al., 1990a; White et al., 1990b; White et al., 2000).

Results

Adenoviral-mediated Expression of p84N5 Induces a G2/M Phase Cell Cycle Arrest

Figure 11:
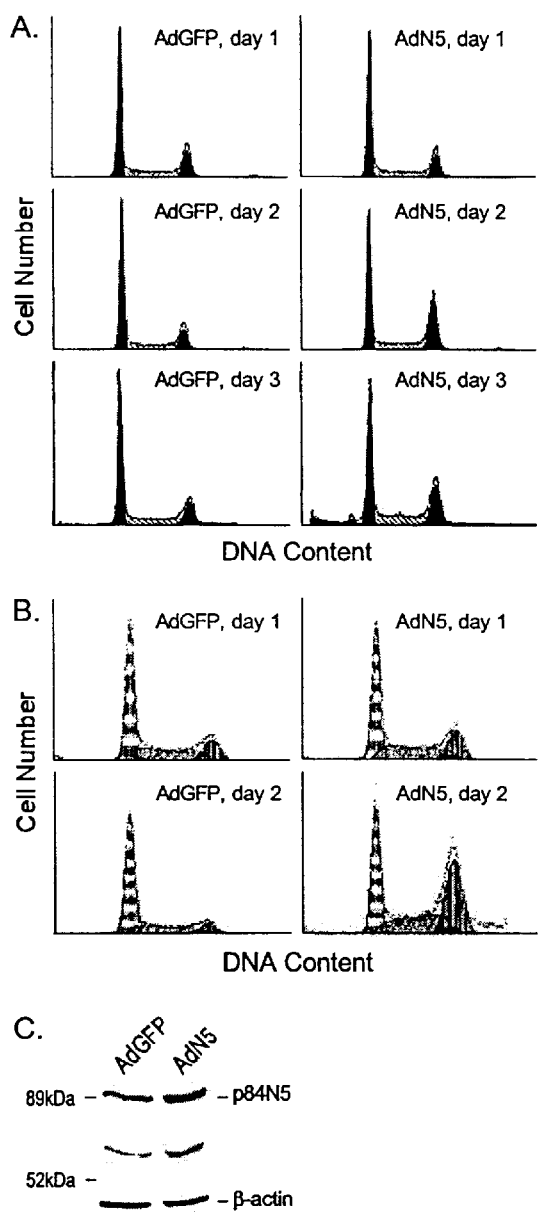
FIG. 11A, FIG. 11B, & FIG. 11C. Adenoviral-mediated p84N5 expression causes cells to accumulate in the G2/M phases of the cell cycle.

The full-length, wild type N5 cDNA was used to generate a recombinant, E1-deleted, replication-defective adenovirus (AdN5) that expressed wild-type p84N5 under control of the cytomegalovirus early promoter and the bovine growth hormone polyadenylation signal (Doostzadeh-Cizeron and Goodrich, 2000; Yin et al., 2000). This adenovirus was used to drive expression of p84N5 in infected cells. The cell cycle distribution of cells at different times after infection was determined by propidium iodide staining and flow cytometry. Two days post-infection, the percentage of cells containing 2N DNA content indicative of G2/M phase increased substantially in AdN5 infected SAOS-2 and C33-A cells relative to cells infected with an adenovirus designed to express the green fluorescent protein (AdGFP) (FIGS. 11A and 11B). AdGFP infected SAOS-2 cells had a mean of 15.8% of cells in the G2/M phase of the cell cycle two days after infection while AdN5 infected cells had a mean of 29.0% of cells in the G2/M phase of the cell cycle at the same time point. The mean percentage of AdGFP infected C33-A cells with G2/M DNA content two days after infection was 13.6% compared to 32.8% for AdN5 infected cells.

To ensure that the changes in cell cycle distribution observed were caused by expression of p84N5, similarly treated SAOS-2 cells were extracted and the protein extracts analyzed for p84N5 by western blotting. AdN5 infected cells show a 3–5 fold increase in the accumulation of p84N5 compared to AdGFP infected cells (FIG. 11C).

These results are consistent with induction of a G2/M cell cycle arrest by p84N5. However, cell death or an alteration in the duration of other cell cycle phases may cause similar changes in cell cycle distribution. To confirm that p84N5 expression increases the duration of G2/M phase, the kinetic parameters of the cell cycle in AdN5 and AdGFP infected cells were compared. S phase cells were pulse-labeled with BrdU at various times after infection. Cell populations at zero and six hours after labeling were analyzed by bivariate flow cytometry. The histograms were used to calculate the potential doubling time, the duration of S phase, and the duration of G2/M phase (Terry et al., 1991; White et al., 1990a; White et al., 1990;b; Terry and White, 1996; White et al., 2000). Consistent with the hypothesis that AdN5 infection triggers a G2/M cell cycle arrest, the duration of G2/M phase for both SAOS2 and C33-A AdN5 infected cells increased compared to AdGFP infected cells (Table 4). For both cell lines, the duration of G2/M phase increased approximately two-fold. There was no consistent difference observed in the duration of S phase or the potential doubling time between AdN5 and AdGFP infected cells.

Figure 12:
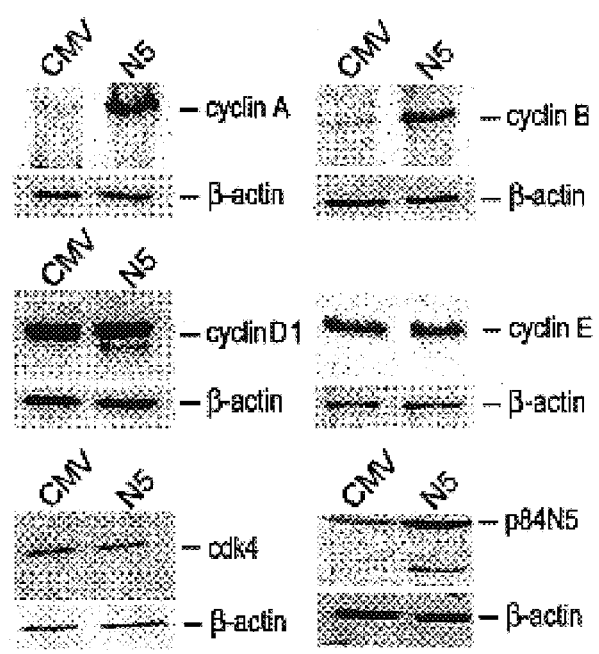
FIG. 12. Changes in the expression level of cell cycle regulatory proteins upon p84N5 expression. Protein from 293 cells transfected with the indicated expression plasmids was extracted two days post-transfection. Equal mass of total cell protein was analyzed by western blotting for the indicated proteins. Blots were re-probed for β-actin to serve as a protein loading control.

Also compared the expression levels of various regulatory proteins that serve as markers of the cell cycle in pCMVN5 versus pCMV transfected cells. Consistent with G2/M cell cycle arrest, the level of both cyclin A and cyclin B protein increase in pCMVN5 transfected cells relative to pCMV transfected cells (FIG. 12). Cyclin A and B are normally expressed beginning in S phase and protein levels peak during G2 phase. The levels of cyclin D1, cyclin E, cdk4, p16 and p27 are not significantly different in pCMVN5 or pCMV transfected cells. As expected, the amount of p84N5 increases 3–5 fold upon pCMVN5 transfection relative to pCMV transfection.

TABLE 4

The Duration of G2/M phases of the cell cycle lengthens upon expression of p84N5
The indicated cell lines were infected with the relevant adenovirus and infected cells pulse labeled with BrdU either 2 (C33-A) or 4 (SAOS-2) days later. Cells were fixed immediately after pulse labeling or six hours later and processed for bivariate flow cytometric analysis of BrdU and PI staining. Kinetic parameters were calculated as described in experimental procedures.

| Kinetic Parameters | SAOS-2 | | C33-A | |
| --- | --- | --- | --- | --- |
| | AdGFP | AdN5 | AdGFP | AdN5 |
| LI (%)[5] | 25.07 | 22.03 | 53.60 | 53.36 |
| TG2 + M[6](h) | 2.50 | 5.10 | 2.62 | 4.39 |
| TS[7](h) | 21.39 | 17.17 | 10.45 | 11.97 |
| TPOT[8](h) | 56.51 | 51.98 | 13.29 | 21.09 |

Figure 13:
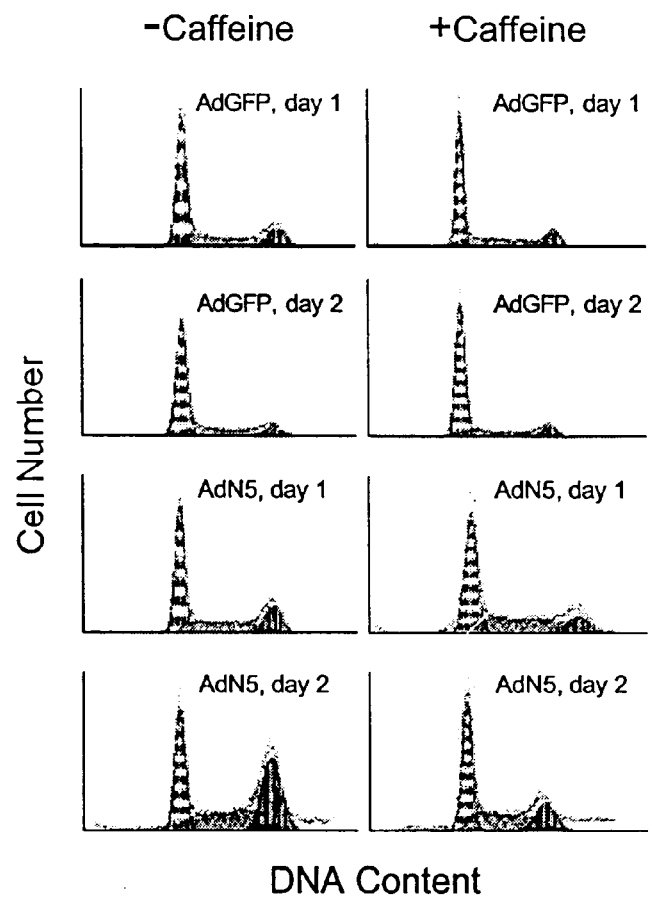
FIG. 13. Caffeine abrogates the p84N5-induced G2/M cell cycle arrest. Cell cycle profiles were calculated for AdN5 or AdGFP infected cells at the indicated time either in the absence of presence of caffeine. The cell cycle profiles were calculated based on plots of cell number versus PI staining intensity (DNA content) obtained from flow cytometric analysis of at least 10,000 cells. The data shown are representative of at least three independent experiments.

[5]Labeling index is the percentage of BrdU labeled cells at the zero time point
[6]The duration, in hours, of the G2 + M phases of the cell cycle
[7]The duration, in hours, of the S phase of the cell cycle
[8]The potential doubling time, in hours, of the cell population The G2/M Checkpoint Activated by p84N5 Expression is Sensitive to Caffeine but does not Require Functional ATM Protein Caffeine has been demonstrated to abrogate cell cycle checkpoint controls that are normally activated in response to DNA damage (Murnane, 1995; Harris, 1985). However, the type of DNA damage and the cell cycle phase in which it occurs influence whether caffeine will affect the subsequent cell cycle checkpoint (Darbon et al., 2000). Abrogation of these checkpoints facilitates subsequent cell death by apoptosis. In particular, caffeine blocks G2/M cell cycle arrest and increases the rate of apoptosis that is normally observed after ionizing irradiation or other genotoxic treatments. The mechanisms utilized by caffeine to block activation of the G2/M cell cycle checkpoint are not completely defined. However, caffeine has been demonstrated to inhibit the ataxia-telangiectasia-mutated (ATM) kinase (Zhou et al., 2000; Blasina et al., 1999). ATM kinase can phosphorylate and activate the cell cycle regulator Chk2/Cds1. Activation of Chk2/Cds1, in turn, enforces a G2/M checkpoint by phosphorylating and inactivating Cdc25C. Cdc25C is normally required to remove an inhibitory phosphate on the mitotic cyclin-dependent kinase Cdk1. Loss of ATM function, therefore, compromises cell cycle checkpoints that are triggered in response to genotoxic stress (Rotman and Shiloh, 1997). The inventors analyzed the effects of caffeine treatment on the p84N5-induced G2/M cell cycle arrest. C33-A cells were infected with AdN5 or AdGFP in the presence or absence of caffeine. The cell cycle distribution of cells was analyzed by propidium iodide staining and flow cytometry at varying times after infection. As in FIG. 11, AdN5 infection induced a significant accumulation of cells in the G2/M phase of the cell cycle by two days post-infection. AdGFP infection had little effect on the cell cycle distribution of cells compared to uninfected controls. Treatment with caffeine, however, prevented the accumulation of G2/M phase cells normally observed upon AdN5 infection (FIG. 13). In the experiment shown, the fraction of G2/M phase cells two days after infection with AdN5 was 36.3% in the absence of caffeine and 18.5% in the presence of caffeine. Similar results were obtained with SAOS-2 cells. Since caffeine abrogated the p84N5-induced G2/M cell cycle arrest and caffeine can inhibit the ATM kinase, the inventors tested the hypothesis that ATM may be required for activation of this checkpoint.

Figure 14:
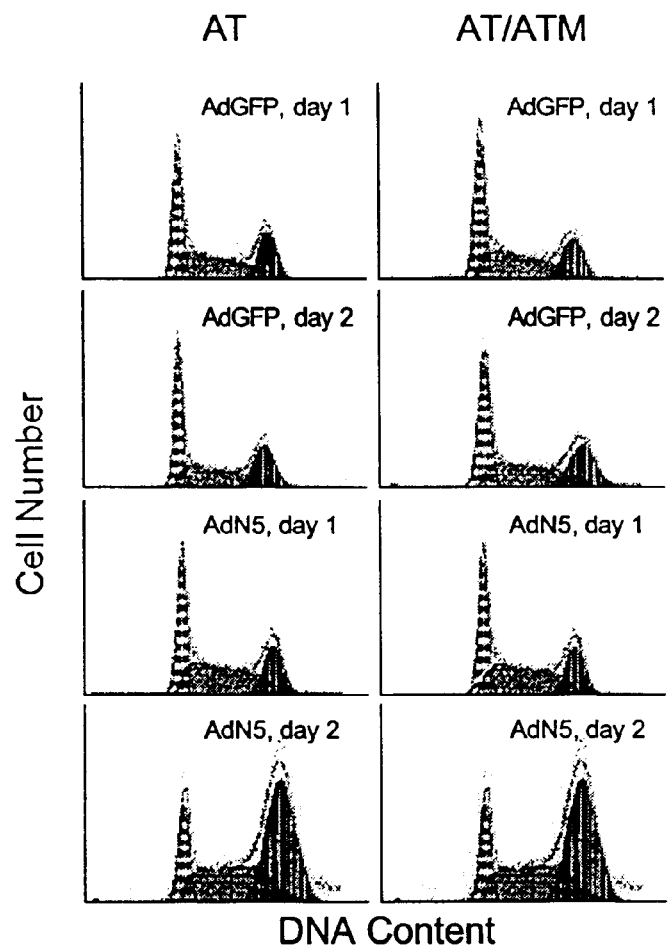
FIG. 14. The p84N5-induced G2/M cell cycle arrest is independent of ATM. AT or AT/ATM fibroblasts were infected with AdN5 or AdGFP and harvested for PI staining and flow cytometry at the indicated times. The cell cycle profiles were calculated based on plots of cell number versus PI staining intensity (DNA content) obtained from flow cytometric analysis of at least 10,000 cells. The data shown are representative of two independent experiments.

Immortalized ataxia-telangiectasia (AT) fibroblasts that lack wild-type ATM and the same cells reconstituted for ATM function by expression of recombinant ATM (AT/ATM) were infected with AdN5 or AdGFP and the cell cycle distribution of infected cells determined. AdGFP infection had little effect on the cell cycle distribution of these cells although a consistent small increase in the fraction of G2/M cells two days following infection was observed (FIG. 14). As in C33-A and SAOS-2 tumor cell lines, AdN5 caused a large increase in the percentage of cells in the G2/M phase of the cell cycle two days after infection. On average, the percentage of G2/M phase AdN5 infected cells was about two-fold greater than AdGFP infected cells for both the AT and AT/ATM cell lines. The presence of reconstituted ATM function did not appear to influence the extent or the rate of the accumulation of G2/M phase cells since the cell cycle distributions for AT and AT/ATM cells were very similar.

Discussion

The results presented here confirm that p84N5 expression activates an authentic G2/M cell cycle checkpoint prior to the onset of apoptosis. This conclusion is supported, first, by the fact that AdN5 causes an accumulation of cells with G2/M phase DNA content two days after infection but prior to the onset of significant apoptosis three days after infection. In contrast, the control adenovirus, AdGFP, does not significantly alter the cell cycle distribution of infected cells relative to uninfected cells. Since similar results have been obtained in two different tumor cell lines and an immortalized human AT fibroblast cell line, the effects observed are unlikely to be cell line or tumor cell specific. Neither p53 nor Rb is required for this G2/M arrest since SAOS-2 cells are null for both. Further, functional ATM is not required for activation of the G2/M checkpoint by p84N5 since AT cells lacking ATM still accumulate in the G2/M phase of the cell cycle after infection with AdN5. Second, the accumulation of cells in G2/M phase is due to an increase in the duration of this phase of the cell cycle. Based on analysis kinetic data obtained from bivariate flow cytometry of BrdU pulse labeled cells, the calculated duration of G2/M nearly doubles upon AdN5 infection relative to AdGFP infection. In contrast, the duration of S phase and the potential doubling time are not consistently dissimilar in AdN5 and AdGFP infected cells. Third, the relative increase in cyclin A and cyclin B expression observed in pCMVN5 versus pCMV transfected cells is consistent with an accumulation of cells in the G2/M phase of the cell cycle since the expression of these proteins peak during this phase. The accumulation of G2/M phase cells upon pCMVN5 transfection also indicates that the effects observed are not dependent on adenoviral mediated gene transfer. Finally, treatment of AdN5 infected cells with caffeine, a known inhibitor of the G2/M cell cycle checkpoint, prevents accumulation of G2/M phase cells.

Like the G2/M checkpoint triggered by DNA damage, the p84N5-activated G2/M checkpoint is sensitive to caffeine. Caffeine can inhibit ATM protein kinase activity and subsequent activation of Chk2/Cds1 (Zhou et al., 2000; Blasina et al., 1999). However, AdN5- and radiation-induced G2/M cell cycle arrest still occurs in the absence of ATM, indicating that ATM-independent mechanisms must exist to enforce a G2/M checkpoint. This finding is consistent with the observations that Chk2 is dispensable for initiation of the G2/M phase checkpoint (Hirao et al., 2000) and that ATM-independent mechanisms may exist to regulate Chk2 (Darbon et al., 2000). The inventors also observed changes in the expression of Cdc25 proteins that could account for alterations in the cell cycle upon pCMVN5 transfection.

DNA damage is one apoptotic signal that unambiguously originates from within the nucleus. The nuclear localized Rb protein negatively regulates DNA damage-induced apoptosis (Haas-Kogan et al., 1995; Park et al., 20004). How Rb influences DNA damage-induced apoptosis is not completely understood. The observation that an amino-terminal domain of Rb not required for cell cycle regulation may be required to inhibit some forms of apoptosis (Riley et al., 199735), suggests that Rb's ability to regulate certain forms of apoptosis is a novel function. Few of the known Rb-associated proteins are known to play a direct role in the initiation of apoptosis. As described here and previously (Doostzadeh-Cizeron et al., 1999; Doostzadeh-Cizeron and Goodrich, 2000), the Rb-associated, nuclear p84N5 protein can trigger a G2/M cell cycle arrest and subsequent apoptosis. Both an intact death domain (Doostzadeh-Cizeron et al., 1999) and nuclear localization are required for p84N5-induced apoptosis. Few proteins are known to require nuclear localization in order to initiate apoptosis and none of those, excepting p84N5, has a functional death domain. Since the death domain encodes a protein-protein interaction motif essential for death receptor apoptotic signaling, the inventors hypothesize that p84N5 is involved in apoptotic signaling from within the nucleus potentially in response to DNA damage. Thus, p84N5 mediates Rb's inhibitory effects on some forms of DNA damage-induced apoptosis and hence the inventors envision its use in anticancer therapy.

Example 12
Nuclear Localization is Required for Induction of Cell Death by the Rb-associated Death Domain-containing N5 Protein In this example the inventors identify the N5 nuclear localization signal and show that nuclear localization is required to inhibit the clonogenicity of N5 expressing cells. Signal transduction pathways culminating in apoptosis in response to extracellular stimuli, like tumor necrosis factor, or in response to mitochondrial signals, such as cytochrome c release, are well characterized (Yuan, 1997; Wolf and Green, 1999). Initiator caspases are typically recruited to protein complexes composed of death receptors and/or adapter molecules. These proteins contain signature protein interaction motifs like the death domain, the death effector domain, or the CARD domain. The locally high concentration of caspase proenzyme recruited to these complexes leads to their activation by proteolytic processing. Caspases so activated trigger a proteolytic cascade that is required for execution of the apoptotic program. Apoptotic signals can also originate from within the nucleus. For example, DNA damage caused by radiation triggers a stress response from within the nucleus that results in apoptotic cell death (Haimovitz-Friedman, 1998). The mechanisms utilized by nuclear signals to initiate apoptosis are not well understood. Few proteins are known to require nuclear localization in order to trigger or regulate apoptosis. Some transcription factors can induce apoptosis, including p53 (Sheikh and Fornace, 2000; Sionov and Haupt, 1999). Although p53 is presumed to trigger apoptosis from within the nucleus by altering the expression of genes involved in the execution of apoptosis (Yin et al., 1997), non-nuclear mechanisms unrelated to transcriptional regulation have also been proposed (Bennett et al., 1998).

Expanded polyglutamine repeat proteins require nuclear localization for their ability to induce the apoptosis that causes Huntington's disease or spinocerebellar ataxia (Klement et al., 1998; Saudou et al., 1998). Activation of caspase-8 is a required step in this process (Sanchez et al., 1999) and is accomplished by recruitment of the proenzyme to characteristic nuclear protein aggregates that are associated with these diseases. The nuclear retinoblastoma tumor suppressor protein (Rb) can inhibit apoptosis initiated by a number of agents (Wang, 1997), including DNA damage (Haas-Kogan et al., 1995). How Rb regulates apoptosis and whether this function is independent of its well-documented ability to regulate the cell cycle is unknown. However, amino-terminal deleted Rb mutants, which retain sequences that are sufficient to regulate the cell cycle in vitro, are unable to restore normal apoptosis in Rb−/− mice (Riley et al., 1997). The observations that some mutations causing low penetrance retinoblastoma specifically alter the N-terminal domain of Rb (Dryja et al., 1993; Hogg et al., 1993; Lohmann et al., 1994) and that the amino-terminal domain is conserved throughout vertebrate evolution also suggest that this domain is important for normal Rb function. The N5 cDNA was originally isolated based on the ability of its encoded protein (p84N5) to bind an amino-terminal domain of Rb (Durfee et al., 1994). The predicted primary sequence of p84N5 has significant homology to the death domain found in proteins important for death receptor apoptotic signaling (Feinstein et al., 1995). For example, the p84N5 death domain has 26% amino acid identity with the death domain of RIP, a kinase that interacts with fas/apo1 receptor. This level of sequence similarity is on par with that observed between other death domain proteins; the TRADD and RIP death domains have 24% identity. Expression of p84N5 can trigger a G2/M cell cycle arrest and subsequent p53-independent apoptosis that is regulated by wild-type Rb, but not an amino-terminal mutant (Doostzadeh-Cizeron et al., 1999). Characteristic point mutations that disrupt other death domain proteins also disrupt the ability of p84N5 to induce apoptosis, suggesting that p84N5 contains a death domain analogous to those identified in other apoptotic signaling proteins. The inventors demonstrate by means of this example that p84N5 contains a bi-partite nuclear localization signal sequence and that nuclear localization is required for p84N5-induced loss of clonogenic potential.

Methods

Cell Culture

All cell lines were obtained from American type culture collection and maintained in Dulbecco's modified Eagle's medium with 10% heat-inactivated fetal bovine serum and antibiotics (100 units/ml penicillin, 100 mg/ml streptomycin), in a 5% $CO_2$ incubator at 37° C.

Plasmids

An 1800 bp fragment encoding amino acids 54 to 656 of the p84N5 cDNA was subcloned in frame into the EGFP-C1 mammalian expression vector to create GFPN5. Subsequent deletion mutants were derived from this construct as follows: GFPN5S-B was created by deleting the SalI-BamHI fragment of GFPN5; GFPN5E-B was created by deleting the EcoRI-BamHI fragment of GFPN5; GFPNSH-S is an in-frame N-terminal deletion created by removing of HindIII-SalI fragment and inserting a HinDIII linker, GFPN5S-E is an in-frame internal deletion created by removing the SalI-EcoRI fragment and inserting a SpeI linker. PCR-mutagenesis was carried out as previously described (Fisher and Pei, 1997). The template for mutagenesis was GFPN5. GFPN5δDNLS was created using the following pair of adjacent phosphorylated primers, 5' AAT-TATTCTCGTAGGTTTGGTATCTGATG 3' (SEQ ID NO: 12) and 5'.6 ATTCTGACGGGAAATGAGGAGTTAA-CAAGG 3' (SEQ ID NO:13). GFPN5δNLS was created using the following pair of adjacent phosphorylated primers, 5' CATCTCCTGGGCATAACGAATTAT-TCTCGTAGGTTTGGTATC 3' (SEQ ID NO:14) and 5' GAAGGCGAAGAAGAAGCCATTCTGACGG-GAAATGAGGAGTTA 3' (SEQ ID NO:15). GFPN5δNES was created using the following pair of adjacent phosphorylated primers, 5' GAACTTCTTCGTCATAATTAT-TCTCGTAGGTTTGGTATC 3' (SEQ ID NO:16) and 5' GGCACGCTCACGATCATTCTGACGG-GAAATGAGGAG 3' (SEQ ID NO: 17).

Transfection and Clonogenicity Assays

Plasmid DNA used for transfection was purified using Qiagen plasmid DNA purification kits as directed by manufacturer (Qiagen, Valencia, Calif.). For clonogenicity assays, SAOS-2 cells were seeded in 100-mm dishes at 25% confluency and transfected the following day using the calcium phosphate precipitation method (Wigler et al., 1979) using 12 mg of total DNA, including 2 mg of EGFP-C1 plasmid (Clontech, Palo Alto, Calif.). The day after transfection, cells were examined for green fluorescent protein (GFP) by fluorescence microscopy to ensure that the transfection efficiency of each sample did not vary significantly. Transfection efficiencies for clonogenicity assays ranged between 10–15%, but transfection efficiencies among different plasmids between experiments were not consistently different. Two days following transfection, cells were grown in the presence of 50 mg/ml G418 to select for successfully transfected cells. Approximately two weeks later, the number of surviving GFP-positive colonies containing greater than 20 cells was counted in at least 50 randomly chosen 100x fields of view using a fluorescence microscope. Cells analyzed by fluorescence microscopy for nuclear localization were plated on etched coverslips the day prior to transfection at 25% confluency. Two days following transfection, coverslips were washed 2× in phosphate-buffered saline (PBS) and fixed in a solution containing.71% paraformaldehyde in PBS. Fixed cells were washed 2× with PBS and 1× with distilled water before mounting on slides. Image stacks spanning the entire thickness of the cell were digitally collected with a Hamamatsu 16-bit camera mounted on a Zeiss Axioplan microscope using a 63× objective using a fluorescein isothiocyanate filter. The image stacks were deconvolved using Zeiss KS400 software and an image slice from the middle of the deconvolved stack exported as a TIF file for presentation. The subcellular distribution of fluorescence in unfixed live cells was similar to fixed cells processed as above.

Western Blotting

For protein expression analysis, 293 cells were transfected as above and two days later resuspended in an ice-cold buffer containing 50 mM Tris, pH 7.4, 250 mM NaCl, 5 mM EDTA, 0.1% NP-40, 50 mM NaF, 1 mM PMSF, 1 mg/ml leupeptin. Protein was extracted by three rounds of freeze/thaw and cell debris was pelleted by microcentrifugation. Total protein concentration of the soluble extract was determined by Bradford assay according to manufacturer's instructions (BioRad, Hercules, Calif.). Twenty-five mg of total soluble protein for each sample was resolved by SDS-PAGE on a 10% gel. The proteins were transferred to nitrocellulose and stained for GFPN5 protein as previously described (Doostzadeh-Cizeron and Goodrich, 2000) using an anti-GFP antibody (Clontech, Palo Alto, Calif.). Primary antibody was detected using a peroxidase-conjugated secondary antibody and Enhanced Chemiluminescence as described by the manufacturer (Amersham Pharmacia Biotech, Uppsala, Sweden).

Results

To facilitate identifying the p84N5 nuclear localization signal (NLS) the inventors sub-cloned the near full-length N5 cDNA into EGFP-C1 to create GFPN5. The plasmid is designed to express.8 an amino-terminal GFPN5 fusion protein containing amino acids 52–657 of the p84N5 protein (FIG. 15A). Following transfection of GFPN5 into SAOS-2 cells, 10–15% of the cells expressed GFP localized within the nucleus as compared to cells transfected with EGFP-C1 that exhibit GFP throughout the cell (FIG. 15B). Hence the GFPN5 fusion protein is correctly localized to the nucleus. However, the GFPN5 fusion protein does not exhibit the punctate staining pattern typically observed upon immunofluorescent staining of endogenous p84N5 (Durfee et al., 1994). This is likely due to the fact that the GFPN5 protein accumulates to a level 3–5 fold greater than the endogenous protein (Doostzadeh-Cizeron and Goodrich, 2000) (FIG. 15C). A small fraction of GFPN5 positive cells, less than 5%, show green fluorescence outside the nucleus. These cells may be undergoing apoptosis since localization of endogenous p84N5 also changes during radiation-induced apoptosis (Doostzadeh-Cizeron et al., 1999).

Figure 15:
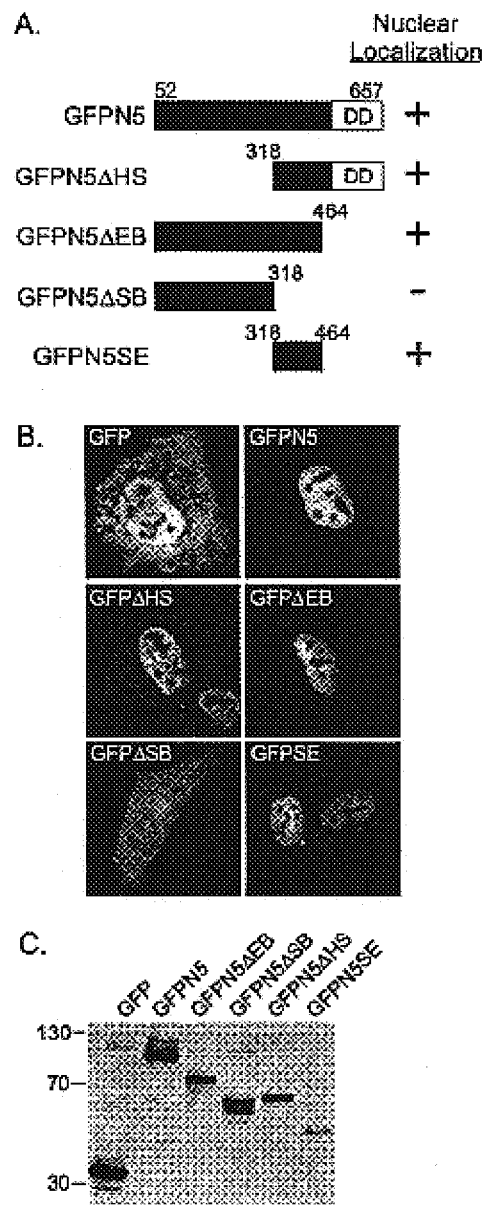
FIG. 15A, FIG. 15B & FIG. 15C. Mapping of amino acids required for exclusive nuclear localization of p84N5.
Figure 16:
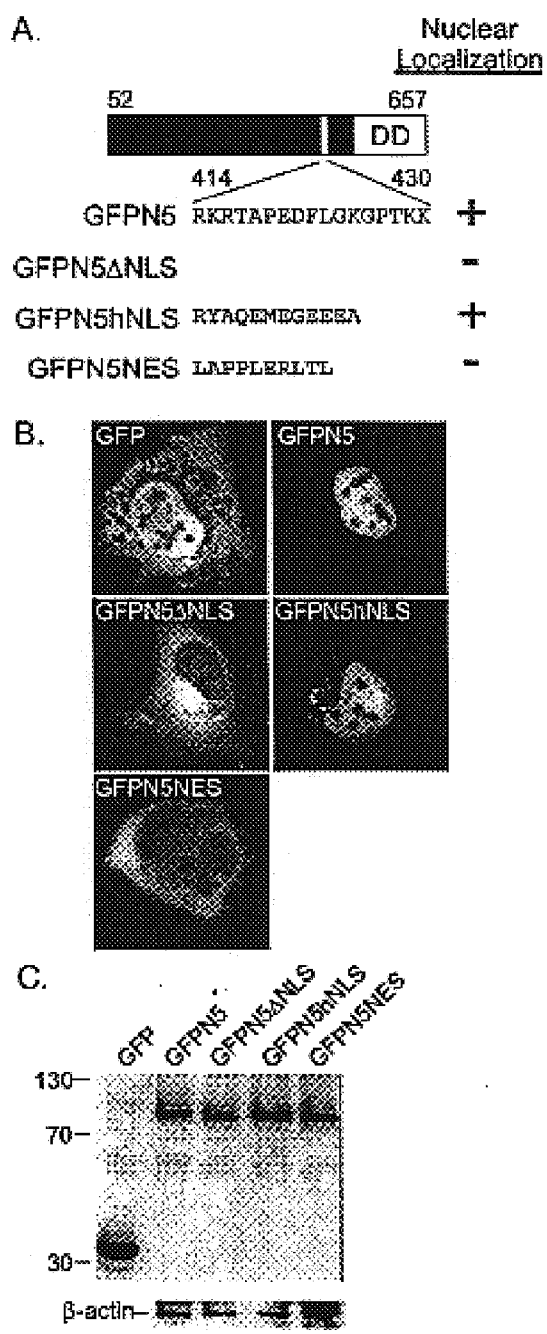
FIG. 16A, FIG. 16B & FIG. 16C. Identification of the p84N5 nuclear localization signal.

To localize the p84N5 NLS, the inventors created a series of deletions within the N5 coding region of GFPN5, expressed them in cells, and analyzed there localization by microscopy. A deletion mutant lacking p84N5 amino acids 318–464 (GFPN5δDSB) expressed GFP fluorescence throughout the cell while a mutant containing only amino acids 318–464 (GFPN5SE) expressed GFP fluorescence only within the nucleus (FIG. 15). Hence p84N5 amino acids 318–464 were both necessary and sufficient to localize the fusion protein exclusively within the nucleus. To ensure that each plasmid construct directed the expression of the correct GFPN5 fusion protein, total protein extracts from transfected cells were analyzed by western blotting using an anti-GFP antibody. All of the plasmids directed expression of a GFPN5 fusion protein of predicted molecular mass (FIG. 15C). Amino acids 318–464 of p84N5 contain a potential bipartite NLS with the sequence RKRTAPED-FLGKGPTKK (SEQ ID NO:9) that spans amino acids 414–430 (FIG. 16A). To test whether this sequence is responsible for localizing GFPN5 to the nucleus, the inventors constructed an in-frame deletion of the sequences encoding these amino acids (GFPN5δDNLS). The inventors replaced these sequences with amino acids that were similar to the nuclear export signal (NES) of HIV-1 Rev (Fischer et al., 1995) in the GFPN5NES mutant which comprises the sequence of SEQ ID NO: 11. Both of these mutants expressed GFP fluorescence that failed to localize exclusively within the nucleus (FIG. 16B). However, replacing p84N5 amino acids 414–430 with a heterologous simple NLS (GFPN5hNLS, which comprises the sequence of SEQ ID NO: 10) restored exclusive nuclear localization of the fusion protein. The fusion proteins expressed by all of the mutant plasmids were analyzed by western blotting of total protein extracted from transfected cells. All of the plasmids expressed a fusion protein of predicted molecular mass confirming that the correct protein was made in each case (FIG. 16C).

Figure 17:
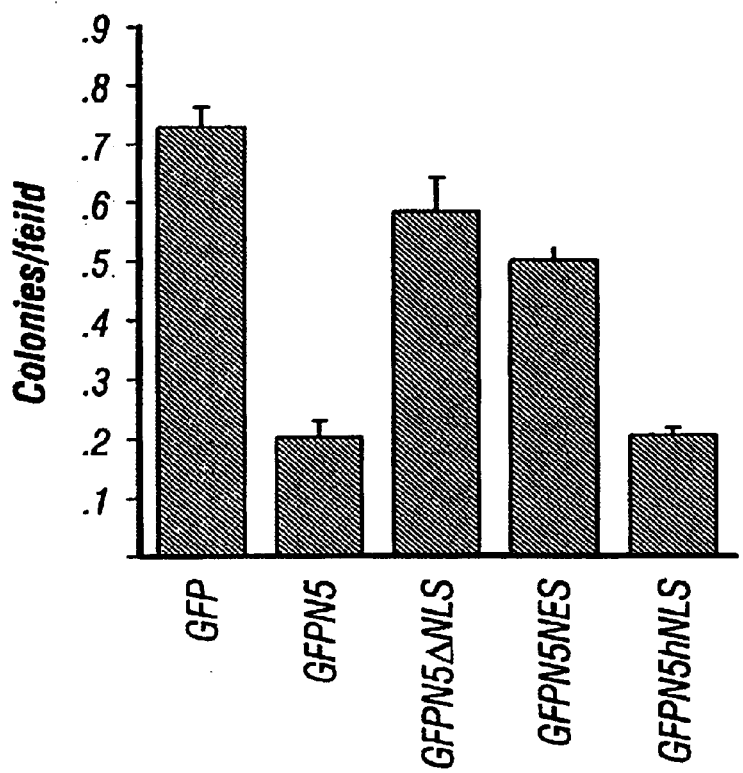
FIG. 17. Nuclear localization is required for p84N5-induced loss of clonogenic potential. SAOS-2 cells were transfected with the indicated GFPN5 fusion protein expression plasmid as well as EGFP-C1 to consistently mark successfully transfected cells and grown in the presence of G418 for two weeks. The number of GFP expressing colonies containing greater than 20 cells was then counted under phase and fluorescent microscopy for at least 50 randomly selected 100× fields of view. The data is expressed as the colonies per field of view. The data shown are the mean and standard deviation of at least three independent transfections for each plasmid.

Expression of p84N5 induces a transient G2/M cell cycle arrest followed by apoptotic cell death (Doostzadeb-Cizeron, 1999). Both of these effects are reflected in reduced clonogenicity of cells overexpressing p84N5 (Doostzadeh-Cizeron, 1999). To test the function of GFPN5 and mutant derivatives, analysis of the ability of transfected cells to form proliferating cell colonies was performed. As expected, cells expressing GFPN5 have a significantly reduced potential to form proliferating colonies, approximately 5-fold, compared to cells expressing GFP (FIG. 17). Cells expressing either the GFPN5δDNLS or GFPN5NES fusion proteins that failed to localize within the nucleus are able to form proliferating cell colonies with approximately 3–4 fold greater efficiency than GFPN5. When exclusive nuclear localization of the GFPN5hNLS fusion protein lacking the p84N5 NLS is restored by addition of a heterologous NLS, the ability to reduce the clonogenic potential of cells expressing this protein is also restored to wild-type GFPN5 levels. Since each of the GFPN5 fusion proteins accumulates to approximately the same level (FIG. 16B), the differences observed in the clonogenicity of cells transfected with these mutants is not due to differences in the efficiency of protein expression.

Discussion

By engineering expression of a GFPN5 fusion protein, the inventors followed p84N5 localization in live cells. Like native p84N5 (Durfee et al., 1994), the GFPN5 fusion protein is localized exclusively within the nucleus in interphase cells. Deletion mapping of GFPN5 identified p84N5 amino acids 318–464 as being required for this nuclear localization. These sequences alone are sufficient to target GFP exclusively to the nucleus as indicated by the GFPN5SE fusion protein. Hence sequence within this region specify the p84N5 NLS. Within this region p84N5 amino acids 414–430 have sequence similarity to other bipartite nuclear localization signals. Upon deletion of these amino acids, the resulting GFPN58DNLS fusion protein loses exclusive nuclear localization defining amino acids 414–430 as the p84N5 NLS. Expression of the correct fusion protein from each of these mutants was confirmed by detection of a GFP fusion protein of predicted molecular mass by western analysis. To test the requirement for nuclear localization in p84N5 function, the inventors assayed the clonogenic potential of cells expressing GFPN5 and mutant derivatives. The ability of GFPN5 to inhibit the clonogenic potential of cells correlated with nuclear localization. Cells expressing mutant proteins that did not localize exclusively in the nucleus, GFPN5δDNLS and GFPN5NES, had greater clonogenic potential than cells expressing nuclear localized GFPN5. Although cells expressing GFPN5δDNLS or GFPN5NES had increased clonogenic potential, they did not form colonies as efficiently as cells expressing GFP. This may be due to accumulation of nuclear protein sufficient to induce cell cycle arrest and apoptosis in a fraction of these cells even in the absence of the defined NLS.

The relative level of nuclear fluorescence observed in cells expressing GFPN5δDNLS or GFPN5NES proteins varied from cell to cell. The range observed was similar in appearance to the GFP expressing cell pictured (FIG. 16B) on the high end to the cell pictured for GFPN5δDNLS on the low end. There was no consistent difference in the relative amount of nuclear fluorescence observed between any of the mutant proteins or GFP even though GFPN5NES contains an NES. Cells expressing a nuclear localized mutant GFPN5 with the p84N5 NLS replaced by a heterologous simple NLS had reduced clonogenic potential similar to cells expressing wild-type GFPN5. This observation indicated that amino acids 414–430 were not required for p84N5-induced loss of clonogenicity and, therefore, that loss of function in the GFPN5δDNLS protein was due to failure to localize to the nucleus rather than disruption of a required functional domain.

Thus, nuclear localization is required for p84N5-induced loss of clonogenic potential. N5 protein can mediate apoptotic cell death and this ability requires an intact death domain located in the C-terminus of the protein (Doostzadeh-Cizeron, 1999). The death domain specifies protein interactions that are required in other apoptotic signaling pathways (Yuan, 1997; Wolf and Green, 1999). Interestingly, p84N5 associates with the nuclear Rb tumor suppressor protein and this association inhibits p84N5-induced apoptosis (Doostzadeh-Cizeron, 1999). The p84N5 sequences required for Rb association overlap with its death domain (Durfee et al., 1994). Rb, therefore, may inhibit p84N5-induced apoptosis by precluding required death domain-mediated interactions. Rb is known to inhibit apoptosis triggered by ionizing radiation (Haas-Kogan et al., 1995). The mechanisms used by Rb to inhibit apoptosis are not completely understood. One potential mediator of this effect is E2F-1. E2F1 can stabilize p53 and promote apoptosis by increasing p14ARF expression (Pomerantz et al., 1998). Association of Rb with E2F1 represses p14ARF expression and inhibits apoptosis. E2F1 can also inhibit activation of anti-apoptotic proteins like NF-kB.12 (Phillips et al., 1999). However, other proteins are likely to mediate some regulation of apoptosis by Rb since inactivation of E2F1 does not reverse all of the deregulated apoptosis observed in the absence of Rb (Macleod et al., 1996; Tsai et al., 1998). Further, amino-terminal Rb mutants that can still associate with E2F1 are insufficient to inhibit some forms of apoptosis in vivo (Riley et al., 1997) and in vitro.

As seen from the art, so far all of the known death domain-containing proteins involved in apoptosis are located outside the nucleus and function in apoptotic signaling pathways triggered by death receptors or mitochondrial signals. Thus, this is a first report that identifies p84N5 as a death domain-containing protein that triggers apoptotic cell death from within the nucleus. This conclusion is consistent with the involvement of p84N5 in a Rb-regulated apoptotic pathway that is normally triggered from within the nucleus, such as in response to DNA damage.

Example 13

Apoptosis Induced by the Nuclear Death Domain Protein p84N5 is Associated with Caspase-6 and NF-kB Activation Although the mechanisms involved in responses to extracellular or mitochondrial apoptotic signals have received considerable attention, the mechanisms utilized within the nucleus to transduce apoptotic signals are not well understood. Here the inventors characterize the underlying mechanisms of apoptosis induced by the nuclear death domain-containing protein p84N5. They also characterize caspase activation, Bcl-2 family member expression, the effects of p53, and NF-kB activation during p84N5-induced apoptosis.

Adenovirus-mediated N5 gene transfer or transfection of p84N5 expression vectors induces apoptosis in tumor cell lines with nearly 100% efficiency as indicated by cellular morphology, DNA fragmentation, and annexin V staining. Using peptide substrates and Western blotting, the inventors determined that N5-induced apoptosis is initially accompanied by activation of caspase-6. Activation of caspases-3 and -9 does not peak until 3 days after the peak of caspase-6 activity. Expression of p84N5 also leads to activation of NF-kB as indicated by nuclear translocation of p65RelA and transcriptional activation of a NF-kB-dependent reporter promoter. Changes in the relative expression level of Bcl-2 family proteins, including Bak and Bcl-Xs, are also observed during p84N5-induced apoptosis. Finally, the inventors also demonstrate that p84N5-induced apoptosis does not require p53 and is not inhibited by p53 coexpression.

Methods

Cell Culture

SAOS-2, 293, MCF-7, and C-33A cell lines were obtained from the American Type Culture Collection and maintained in Dulbecco's modified Eagle's medium with 10% heat-inactivated fetal bovine serum and antibiotics (100 units/ml penicillin, 100 mg/ml streptomycin), in a 5% CO2 incubator at 37° C. Growth curves with these cell lines were assayed by plating 500,000 cells per well of a 60-mm tissue culture dish, treating with indicated virus at an multiplicity of infection (m.o.i.) of 10, harvesting cells by trypsinization at the indicated time after infection, and counting the number of cells that exclude trypan blue with a hemacytometer. The Colo357 X cell line was obtained from Dr. Keping Xie (M. D. Anderson Cancer Center) and was grown as above. Growth assays of virally infected Colo357 X cells were performed by plating at a density of 20,000 cells/well in 24-well plates in triplicate. One day later, the cells were infected with the indicated adenoviruses at a total m.o.i. for all viruses of 50. An equal number of cells were treated with PBS as a control. Cells were harvested at different time intervals and viable cells, as indicated by trypan blue exclusion, were counted using a hemacytometer.

Plasmids and Adenovirus

The full-length p84N5 cDNA was sub-cloned into pCEP4 (Invitrogen, Carlsbad, Calif.) expression vector to create the expression vector pCMVN5. The Bcl-2 (Herrmann et al., 1997), p53 (Chen et al., 1991), and pRb (Leng et al., 1997) expression vectors were previously described. The NF-kB luciferase reporter plasmids (Uhlik et al., 1998) and RelA expression plasmid (Chiao et al., 1994). To generate the recombinant p84N5 expressing adenovirus, the p84N5 cDNA was subcloned into the pAdCMV (AS)-BGHpa vector (Dr. T. J. Liu, M. D. Anderson Cancer Center). The resulting plasmid, was coelectroporated with pJM17, the adenovirus backbone plasmid, into 293 cells and recombinant N5 adenovirus (AdN5) identified by polymerase chain reaction using primers specific for N5 essentially as described (Zhang et al., 1993). Recombinant adenovirus was purified by CsCl equilibrium density gradient centrifugation, and viral particle numbers were estimated by A260 in the presence of SDS as described (Huyghe et al., 1995). Infectious titer was determined by an end point assay using an adenovirus direct immunofluorescence kit (Chemicon International, Inc.). The GFP and p53-expressing adenoviruses were gifts of Dr. T. J. Liu and were prepared as above.

Transfection and Apoptosis Assays

For transfections, cells were seeded on 100 mm dishes and transfected the following day by calcium phosphate precipitation (Wigler et al., 1979) using 6–30 mg of total DNA. To analyze transfected or infected cells for DNA fragmentation, cells were collected 24 h after treatment and free DNA ends were stained with terminal deoxytransferase (TUNEL) using the APO-DIRECT kit (Phenix Flow Systems, San Diego, Calif.) according to manufacture's instructions. Annexin V staining was assayed 2 days following infection by harvesting cells by trypsinization, washing with PBS, and staining with annexin V Alexa 568 following the manufacturer's instructions (Roche Molecular Biochemicals). FACS analysis was performed on a FACS-Calibur instrument (Becton Dickinson, San Jose, Calif.). Hoechst 33342 (Roche Molec-ular Biochemicals) staining was performed by adding the dye at a final concentration of 1 mg/ml to the culture media. Cells were incubated with the dye for 10 min and immediately photographed at 1003 magnification under a fluorescence microscope with a UV filter. To assay activation of caspase activity, cells were infected by addition of AdGFP or AdN5 to the culture media. Cells were incubated at 37° C. for the desired length of time and then collected, washed twice with PBS, and extracted, and the extracts were analyzed for caspase activity using colorimetric peptide substrates as directed by the manufacturer (Bio-Vision, Palo Alto, Calif.). For analysis of luciferase reporter gene activity, transfected cells were washed twice with PBS and lysed, and aliquots of the lysate corresponding to $5 \times 10^4$ successfully transfected cells were assayed for luciferase activity using reagents from the Analytical Luminescence Laboratory (Ann Arbor, Mich.). The pEGFPC1 vector was included in the transfections to determine the transfection efficiency. Cells were examined for GFP by fluorescence microscopy prior to extraction.

Western Blotting

For Western analysis, transfected cells were ex-tracted in a buffer containing 50 mM Tris, pH 7.4, 250 mM NaCl, 5 mM EDTA, 0.1% Nonidet P-40, 50 mM NaF, 1 mM phenylmethylsulfonyl fluoride, 1 mg/ml leupeptin on ice for 10 min. The total protein concentration of the soluble extract was determined by Bradford assay according to the manufacturer's instructions (Bio-Rad, Hercules, Calif.). 70 mg of total protein for each sample was resolved by 10% SDS-polyacrylamide gel electrophoresis, blotted, and stained as described previously (Doostzadeh-Cizeron et al., 1999). Antibodies directed against p84N5 (Durfee et al., 1994) and pRb (Connell-Crowley et al., 1997) were described previously. All other primary antibodies were used as directed by the manufacturer. Antibodies directed against caspases were obtained from Oncogene Research Products (Cambridge, Mass.), all other antibodies were obtained from Santa Cruz Biotechnology (Santa Cruz, Calif.). Primary antibodies were detected using a peroxidase conjugated secondary antibody and enhanced chemiluminescence according to the manufacturer's recommendations (Amersham Pharmacia Biotech).

Results

Expression of p84N5 Induces Apoptosis through Activation of Caspase-6

The full-length, wild type N5 cDNA was used to generate a recombinant, E1-deleted, replication-defective adenovirus (AdN5) that expressed wild-type p84N5 under control of the cytomegalovirus early promoter and the bovine growth hormone polyadenylation signal. This adenovirus was used to drive expression of p84N5 in infected cells. The proliferation of cells infected with AdN5 at a multiplicity of infection (m.o.i.) of 10 slowed significantly by the third day after infection (FIG. 18). Nearly all AdN5-infected cells died by 6 days after infection. The proliferation of cells infected with a similarly con-structed GFP-expressing recombinant adenovirus (AdGFP) was similar to uninfected cells. Both AdGFP-infected and untreated cells reached confluency by day 4, explaining the decrease in proliferation rate observed at the later stages.

Characterization of p84N5-induced Apoptosis

Figure 18A:
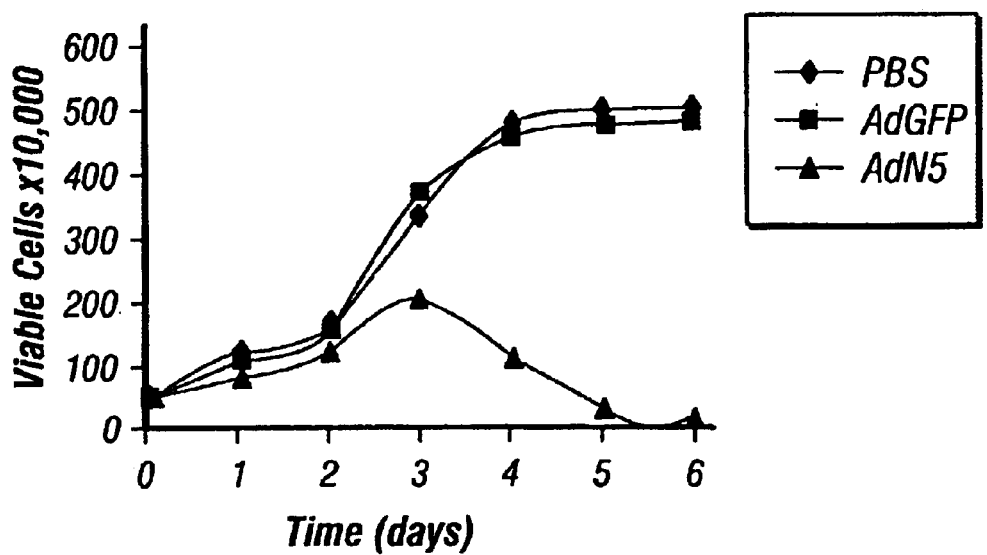
FIG. 18A, FIG. 18B, FIG. 18C, FIG. 18D & FIG. 18E. AdN5-mediated p84N5 expression induces apoptosis FIG. 18A. equal numbers of SAOS-2 cells were infected with the indicated virus at m.o.i. of 10 or left untreated. On subsequent days, the number of viable cells in each aliquot was counted. The data are from a single representative experiment that has been repeated five times.
Figure 18B:
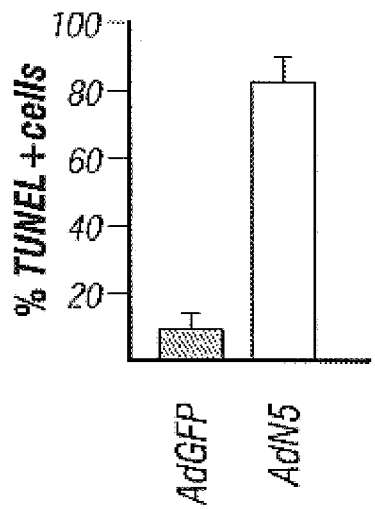
Figure 18C:
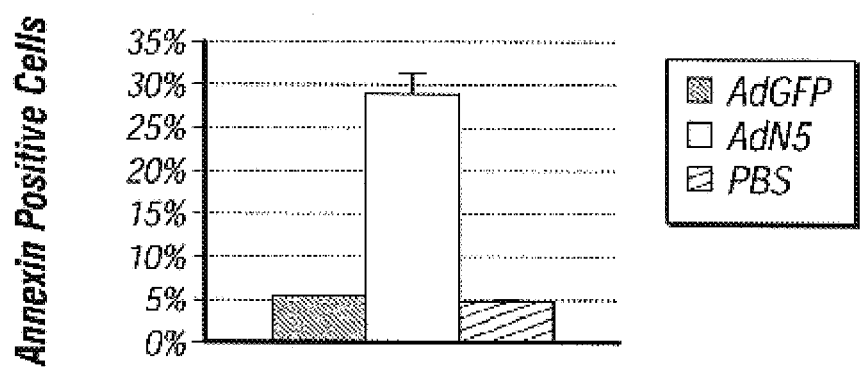
Figure 18D:
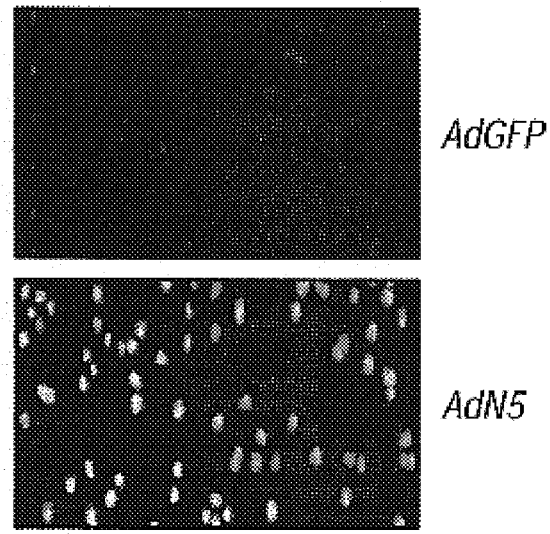
Figure 18E:
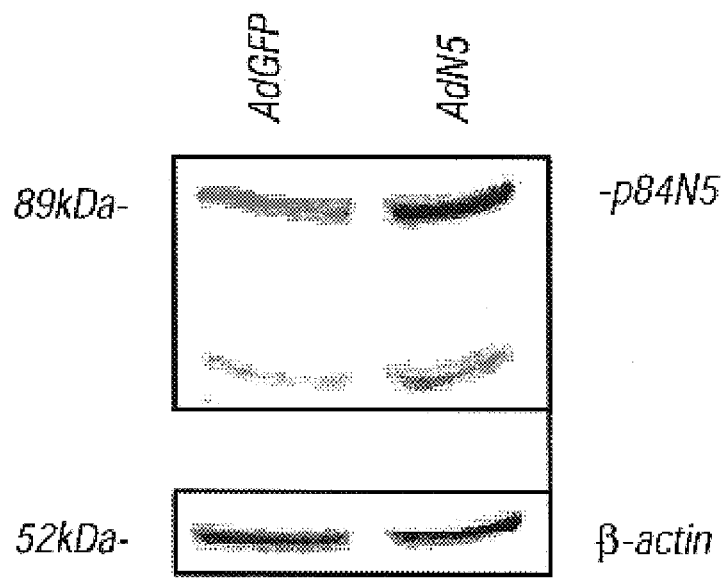

To test whether the observed decrease in cell viability of AdN5-infected cells was due to apoptosis, cells were assayed for the presence of fragmented DNA by TUNEL 3 days after infection. Nearly 80% of cells infected with AdN5 con-tained fragmented DNA (FIG. 18B). Infection with AdGFP did not alter the percentage of TUNEL-positive cells relative to uninfected cells. Consistent with this observation, AdN5-infected cells also demonstrated an increase in phosphatidylserine exposure on the outer leaflet of the plasma membrane as determined by annexin V staining (FIG. 18C). Finally, AdN5 infected cells exhibited an increased permeability to Hoechst 33342 and condensed chromatin (FIG. 18D). AdGFP infected cells did not show increases in annexin V or Hoechst 33342 staining. To ensure that apoptosis induced by AdN5 coincided with increased expression of p84N5, protein extracts prepared from infected cells were analyzed by Western blotting using a mouse antiN5 monoclonal antibody. 24 h after infection, the level of p84N5 expression had increased in AdN5-treated cells at least 5-fold relative to AdGFP treated cells (FIG. 18E). The efficiency of adenoviral-mediated gene transduction under the conditions used in these experiments was 98% as determined by fluorescent microscopy of AdGFP infected cells.

Figure 19A:
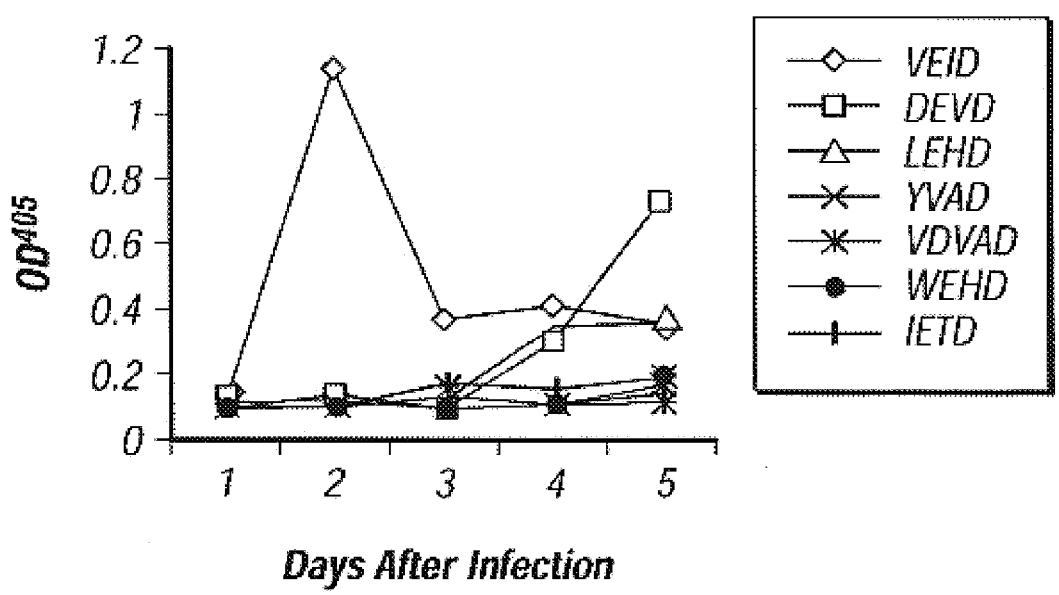
FIG. 19A & FIG. 19B. AdN5-induced apoptosis involves activation of caspase-6.
Figure 19B:
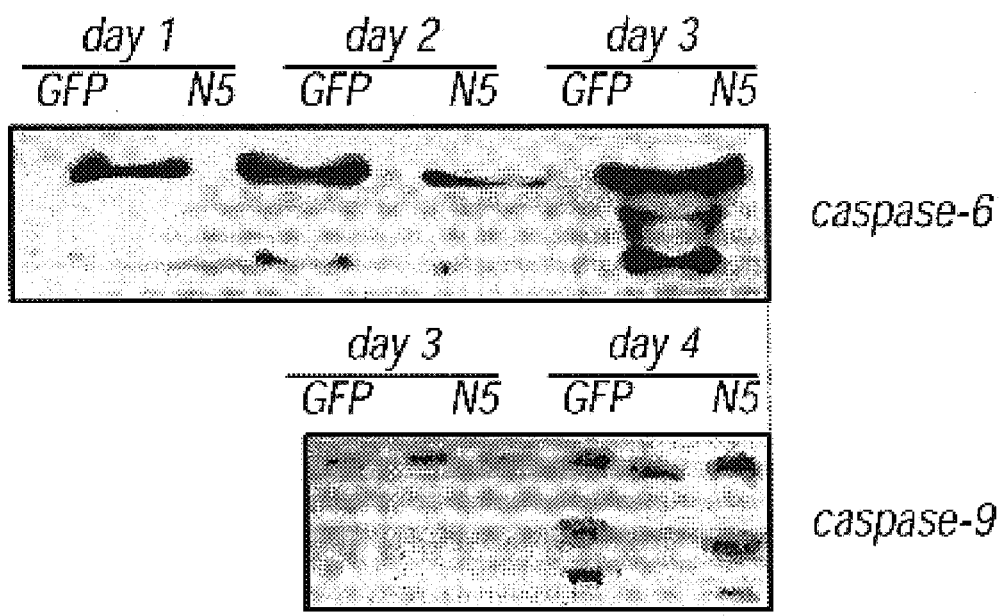

To identify the caspases activated during N5-induced apoptosis, extracts prepared from infected cells have been assayed for caspase activity using seven different colorimetric peptide substrates. Extracts prepared 48 h after infection contain significant VEID peptide cleavage activity (FIG. 19A). VEID is an efficient substrate for caspase-6 (Thornberry et al., 1997). Interestingly, the level AdN5-induced DEVD cleavage activity does not increase above background until 4 days after infection, and the relative extent of activation is lower than VEID cleavage activity. DEVD is an efficient substrate for caspases-3 and -7. A small increase in LEHD cleavage activity is also observed 4–5 days after infection. LEHD is an efficient substrate for caspase-9. Increases in cleavage activity of the other peptides tested, which include efficient substrates for capases-1, -2, -4, -5, and -8, were not detected upon AdN5 infection. AdGFP infected cell extracts did not contain cleavage activity above background for any of the peptides tested.2 To confirm that caspase-6 was involved in the increase in VEID cleavage activity upon AdN5 infection, extracts were analyzed for proteolytic processing of caspases-6 and -9 by Western blotting. Proteolytically processed caspase-6 was de-tected in extracts prepared 2 or 3 days after infection with AdN5, but not in extracts prepared from AdGFP-infected cells (FIG. 19B). Processing of caspase-9 was also detected in extracts prepared 4 days after infection. These observations indicated that the activation of VEID cleavage activity detected was likely due, at least in part, to activation of caspase-6.

Activation of NF-kB During p84N5-induced Apoptosis

Figure 20A:
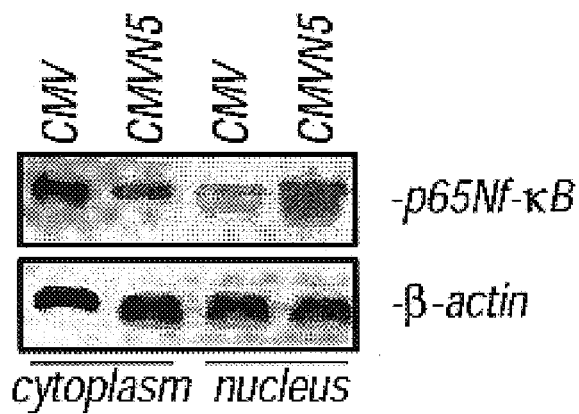
FIG. 20A & FIG. 20B. Activation of NF-KB during p84N5-induced apoptosis.
Figure 20B:
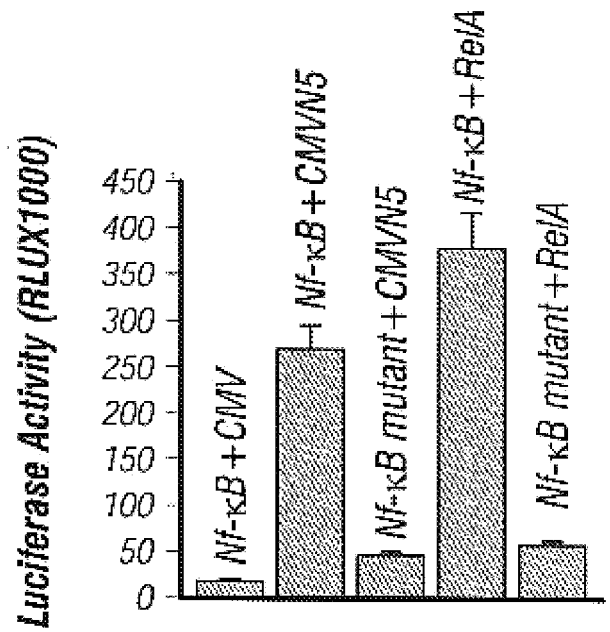

Activation of NF-kB serves as a survival signal in response to varied apoptotic stimuli, including genotoxic agents like ionizing radiation (Wang et al., 1996). Activation of NF-kB involves translocation of the protein from the cytoplasm to the nucleus where it functions as a transcription factor to regulate the expression of target genes. To examine possible activation of NF-kB by p84N5, nuclear or cytoplasmic extracts prepared from 293 cells transfected with pCMVN5 or empty vector have been analyzed by Western blotting using an anti-p65RelA monoclonal antibody. In comparison to cells transfected with empty vector, the level of p65RelA in the cytoplasm of pCMVN5-transfected cells decreases while the relative level of p65RelA in the nucleus increases (FIG. 20A). To test whether the nuclear translocation of p65RelA coincides with increased transcriptional activity, a luciferase reporter gene driven by an artificial NF-kB-responsive promoter was cotransfected with pCMVN5 or empty vector, and the levels of luciferase activity in the extracts of transfected cells were assayed. Expression of p84N5 potently increases luciferase activity generated from the NF-kB-responsive promoter construct but not from a reporter construct containing a mutant promoter that is insensitive to NF-kB (FIG. 20B). The level of reporter gene induction by p84N5 expression was similar to that achieved by expression of exogenous p65RelA.

Changes in Bcl-2 Family Member Gene Expression During p84N5-induced Apoptosis

Figure 21A:
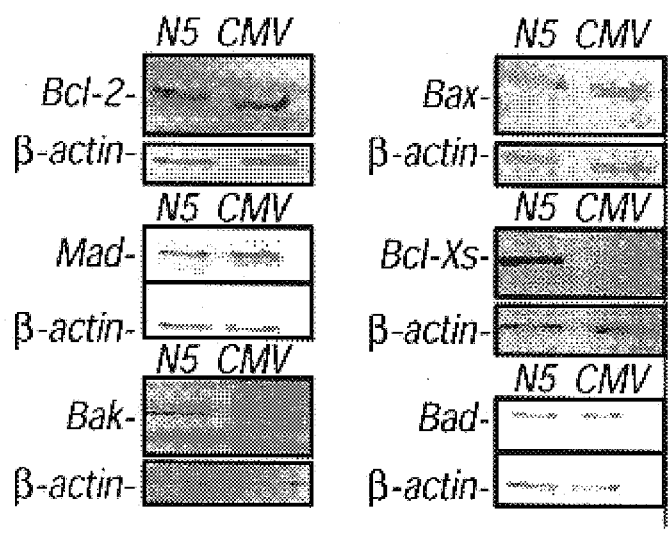
FIG. 21A & FIG. 21B. Changes in Bcl-2 family protein expression during p84N5-induced apoptosis.

Bcl-2 and its homologues are critical regulators of cell death. Changes in the expression of either proapoptotic or antiapoptotic family members can facilitate apoptosis. The inventors examined the expression of Bak, Bax, Bad, Bcl-Xs, and Bcl-2 during p84N5-induced apoptosis by Western blot analysis. Transfection of pCMVN5 into 293 cells or SAOS-2 cells causes detectable apoptosis within 48 h (Doostzadeh-Cizeron et al., 199913). An increase in relative protein expression of Bak and Bcl-Xs was detected in similarly transfected 293 cells relative to cells transfected with empty vector (FIG. 21A). No change in the relative level of expression of Bad, Bax, or Bcl-2 was detected in N5-transfected cells. Nor were there changes in MAD protein expression. Bak and Bcl-Xs are apoptotic agonists that heterodimerize with Bcl-2 and inhibit its ability to protect cells from cell death (Boise et al., 1993; Chittenden et al., 1995; Kiefer et al., 1995). The increase in expression of these genes can facilitate p84N5-induced apoptosis. If true, a compensating increase in Bcl-2 expression would be predicted to inhibit p84N5-induced apoptosis. To test this possibility, the inventors coexpressed Bcl-2 with p84N5 and measured the effect on apoptosis using the TUNEL assay. More than 90% of transfected cells express Bcl-2.

Figure 21B:
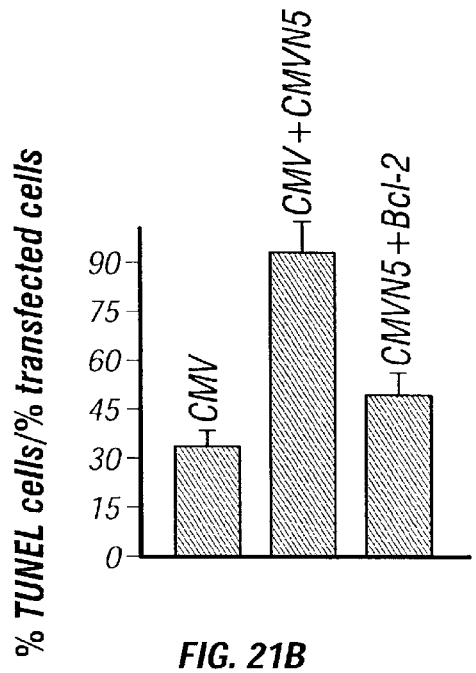

Characterization of p84N5-induced Apoptosis p84N5 alone contain fragmented DNA. Coexpression of Bcl-2 with p84N5 decreases the percentage of cells containing fragmented DNA to near background levels (FIG. 21B).

N5-induced Apoptosis Does Not Require and Is Not Inhibited by p53

Figure 22A:
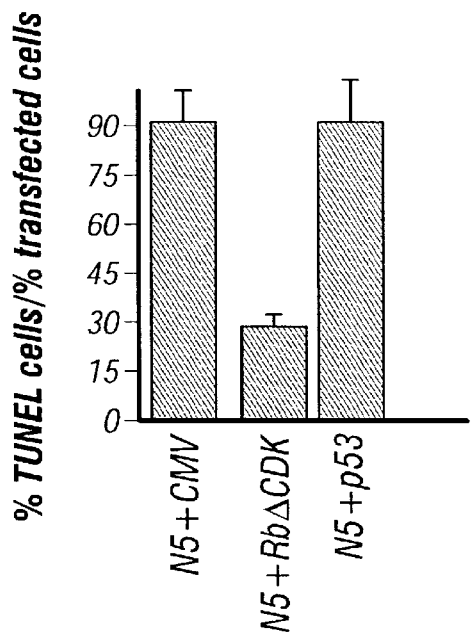
FIG. 22A, FIG. 22B & FIG. 22C. N5-induced apoptosis is independent of p53 status.

The inventors also demonstrate that the expression of p84N5 in p53 null SAOS-2 cells (Chandar et al., 1992) induces apoptosis (FIG. 18A), indicating that p53 was not required for p84N5-induced apoptosis. The inventors contemplated the possibility that p53 may inhibit p84N5-induced apoptosis. Thus, p84N5 and wild-type p53 were expressed in SAOS-2 cells and the cells assayed for apoptosis by TUNEL. Coexpression of wild-type p53 did not affect the percentage of cells containing fragmented DNA (FIG. 22A). Consistent with 13, expression of a constitutively active pRb mutant (RbDCDK) decreased the percentage of cells containing fragmented DNA. Expression of p53 and RbDCDK upon transfection of the appropriate expression vectors was confirmed by Western blotting.

Figure 22B:
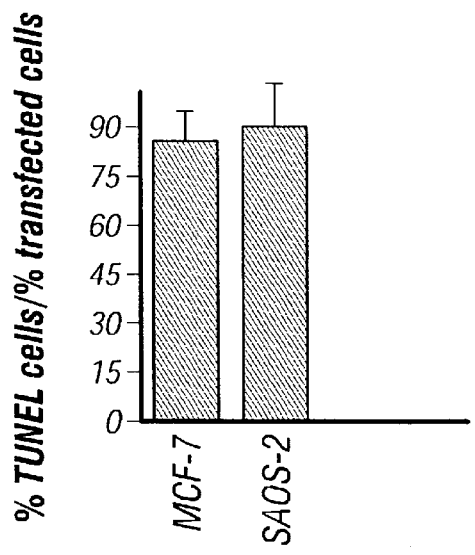
Figure 22C:
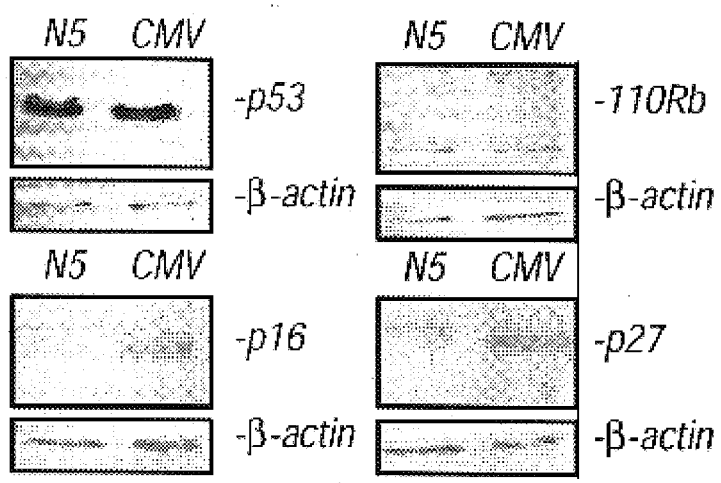
Figure 23:
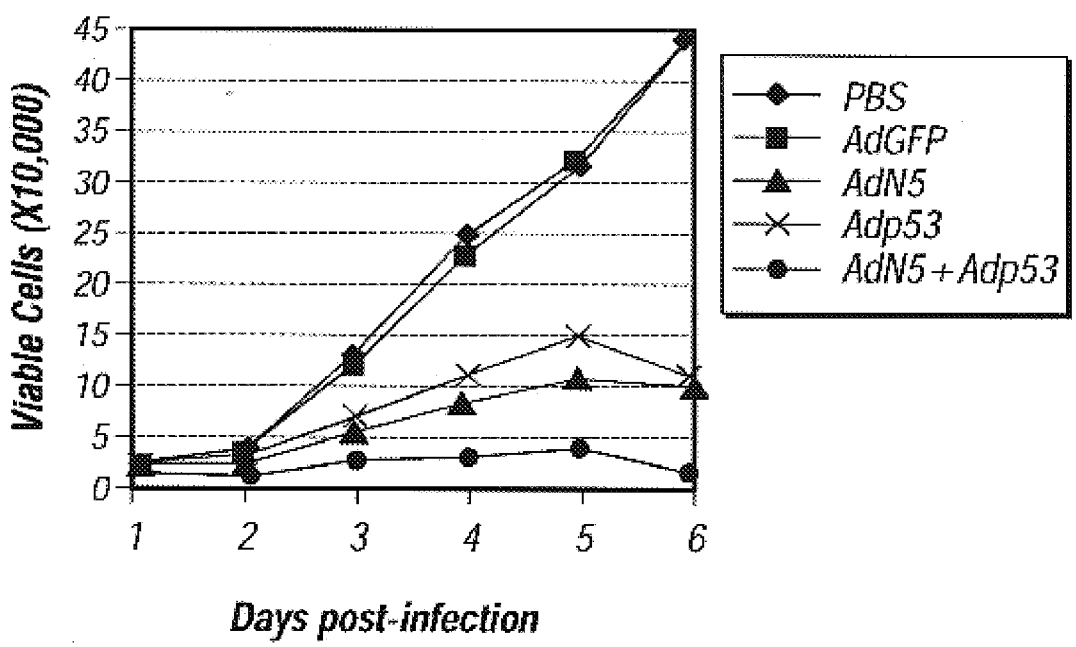
FIG. 23. Infection with both AdN5 and Adp53 reduces cell growth to a greater extent than treatment with either virus alone. Aliquots of 20,000 Colo357 X cells were infected with the indi-cated viruses, or PBS, and the number of viable cells remaining at the indicated times after infection determined. Each data point is the mean of three infections. The standard deviation for each data point is smaller than the size of the symbol representing that point. The total m.o.i. of all viruses combined in each sample is 50. At this m.o.i., more than 90% of AdGFP-infected cells fluoresce green.

The inventors also compared the effects of pCMVN5 transfection in wild-type p53 expressing MCF-7 cells or SAOS-2 cells. MCF-7 and SAOS-2 cells were equally sensitive to p84N5-induced apoptosis as indicated by the similar percentage of transfected cells containing fragmented DNA (FIG. 22B). MCF-7 and SAOS-2 cells were also equally sensitive to apoptosis induced by AdN5 (Yin et al., 2000). Finally, the inventors also analyzed the effect of p84N5 expression on the relative level of endogenous p53, p110Rb, p16, or p27 expression by Western blotting. The expression level of each of these proteins was similar in CMVN5-transfected cells and cells transfected with empty vector (FIG. 22C). These observations suggested that N5 and p53 function in different apoptotic pathways. If true, the effects of each gene on the inhibition of cell growth would be expected to be at least additive. To test this prediction, the effect of AdN5 infection, Adp53 infection, or a combination of both on the growth of Colo357 X cells was determined. These cells are relatively resistant to the effects of AdN5, 3 allowing any increase in the effect of infection on cell growth to be determined. Both AdN5 infection and Adp53 infection decreased the growth rate of these cells. Treatment with either virus caused the number of cells to decrease by day 6. The kinetics of cell accumulation upon AdN5 or Adp53 infection appeared similar; AdN5 had a slightly greater effect on cell growth than did Adp53. Interestingly, infection with a combination of both viruses had an even greater effect on cell growth (FIG. 23). The number of cells infected with AdN5 and Adp53 at any one time were typically 2- to 4-fold less than the number of cells infected with either AdN5 or Adp53 alone. This difference is likely an underesti-mate, because the m.o.i. of each virus in the combination infection is half that of the m.o.i. in the single infections.

Discussion

Forced expression of p84N5, either by transfection or adenovirus-mediated gene transfer, renders cells inviable. Loss of viability is due to induction of apoptotic cell death, because p84N5-expressing cells exhibit many of the typical characteristics of this process, including fragmentation of DNA, exposure of phosphatidylserine on the outer leaflet of the plasma membrane, changes in membrane permeability, and changes in cellular and nuclear morphology. The p84N5 protein has significant sequence similarity to the death domains of other proteins involved in apoptosis (Feinstein et al., 1995), and characteristic point mutations known to inactivate other death domains.

Characterization of p84N5-induced Apoptosis p84N5 is unique among death domain containing proteins in its nuclear localization (Durfee et al., 1994) and nuclear localization is required for p84N5-induced cell death. There is a relatively small number of proteins that are known to initiate apoptosis from within the nucleus, including the expanded polyglutamine repeat proteins and possibly transcription factors like p53. To test whether the apoptotic pathway triggered by p84N5 expression is similar to that triggered by these other nuclear proteins, the inventors have examined the activation of NF-kB, changes in Bcl-2 family protein expression, the effects of p53, and caspase activation during p84N5-induced apoptosis. NF-kB activation during p84N5-induced apoptosis is indicated by the change in localization of p65RelA from the cytoplasm to the nucleus in AdN5-infected cells but not in AdGFP-infected cells. The change in subcellular localization is accompanied by an increase in NF-kB-dependent transcriptional activation as determined by increased levels of a luciferase reporter gene whose transcription is dependent on NF-kB transactivation. In contrast to p84N5, expression of p53 inhibits NF-kB activation (Webster and Perkins, 1999; Wadgaonkar et al., 1999). Activation of NF-kB is observed during apoptosis initiated by DNA-damaging agents like ionizing radiation (Devary et al., 1993; Singh and Lavin, 1990), among others (Kasibhatla et al., 1998; Legrand-Poels et al., 1995). Although similar mechanisms may be utilized to activate NF-kB, p84N5-induced apoptosis is unlikely to be mediated by NF-kB-mediated Fas ligand expression, and CD95 ligation as has been proposed for some DNA-damaging agents (Kasibhatla et al., 1998). Fas-mediated apoptosis requires activation of caspase-8 and is CrmA-sensitive, whereas p84N5-induced apoptosis does not require caspase-8 activation and is insensitive to Crm A (see below).

It is also demonstrate that apoptosis induced by p84N5 is accompanied by an increase in the relative expression of proapoptotic Bcl-2 family members Bak and Bcl-Xs. The expression of Bcl-2, Bax, and Bad are unchanged during p84N5-induced apoptosis. In contrast, p53-induced apoptosis involves an increase in the relative expression of Bax (Miyashita and Reed, 1995). Alteration in the levels of Bcl-2 family protein expression can change mitochondrial membrane permeability allowing release of cytochrome c. Cytoplasmic cytochrome c participates in a protein complex composed of caspase-9 and Apaf-1 that leads to caspase activation (Zou et al., 1997). For example, Bak can accelerate release of cytochrome c through mitochondrial porin channels (Shimizu et al., 1999). Bak can also disrupt association of Apaf-1 and the antiapoptotic Bcl-2 family protein Boo (Song et al., 1999). Hence, p84N5-induced apoptosis may be facilitated by the increase in Bak expression observed. Consistent with this hypothesis, the inventors demonstrate that coexpression of Bcl-2 can inhibit p84N5-induced apoptosis. Furthermore, like p84N5-induced apoptosis, apoptosis induced by forced expression of Bak is insensitive to CrmA (Orth and Dixit, 1997). However, because p84N5-induced apoptosis is initiated by caspase-6 activation rather than caspase-9, Bak either facilitates apoptosis by a different mechanism or it participates in the later execution stages of the process. Whether p84N5 can directly influence transcription is unknown. However, NF-kB can regulate the transcription of some Bcl-2 family genes (Lee et al., 1999; Tsukahara et al., 1999), so the effect of p84N5 on the expression of Bcl-2 family proteins may be indirect.

The inventors also show that p84N5-induced apoptosis does not require p53. Cells with wild-type p53 (MCF-7) or null for p53 (SAOS-2) are equally sensitive to p84N5-induced cell death. Furthermore, the inventors show that p84N5-induced apoptosis does not alter the level of p53 expression and that coexpression of p53 does not inhibit p84N5-induced apoptosis. Thus, N5 and p53 appear to function in different apoptotic pathways. As described above, p53 and p84N5 have different effects on NF-kB activation and Bcl-2 family protein expression. Furthermore, p53-induced apoptosis is de-pendent on caspase-3 and/or caspase-9 in many cases (Cregan et al., 1999; Soengas et al., 1999; Yu and Little, 1998). These caspases are not required for p84N5-induced apoptosis.

Finally, the inventors show that infection with both AdN5 and Adp53 causes a more dramatic reduction of Colo357 X cell growth than infection with either one alone. Genes that participate in or activate the same apoptotic pathway would not be expected to have such an additive or synergistic effect. Thus, N5 and p53 function in different pathways, N5-induced apoptosis is preceded by a G2/M cell cycle arrest while expression of p53 typically induces a G1 cell cycle arrest.

Characterization of p84N5-induced Apoptosis

Caspase-6 is the first caspase activated, and it makes up the majority of caspase activity observed in extracts of AdN5-infected cells. This conclusion is based upon cleavage of a peptide substrate, VEID, that is preferred by caspase-6 as well as by detection of proteolytically processed caspase-6. The pattern of caspase activation is unlikely to be influenced by adenoviral infection, because caspases are not activated in AdGFP-infected cells. Because activation of caspase-6 precedes or is coincident with DNA fragmentation, annexin V staining, and loss of cell viability, the inventors conclude that it may mediate p84N5-induced apoptosis.

Activation of caspase-9 and caspase-3 activity is also detected in AdN5-infected cells. However, activation of these caspases is unlikely to mediate p84N5-induced apoptosis. First, activation of caspase-9 or -3 occurs after execution of apoptosis has already begun. The activation of a caspase-3, for example, is not detected until 4 days after infection, well after the time when DNA fragmentation can be detected. This observation suggests activation of caspases-9 and -3 is a consequence of earlier caspase-6 activation. Second, MCF-7 cells, which lack caspase-3 (Janicke et al., 1998), are sensitive to AdN5. Hence, caspase-3 is not required for p84N5-induced apoptosis. This pattern of caspase activation suggests that p84N5 triggers an apoptotic pathway distinct from those triggered by expanded polyglutamine repeat proteins or death domain-containing receptors.

Apoptosis induced by these proteins require caspases-3, -8, or -9, whereas p84N5-induced apoptosis involves caspase-6. Short prodomain caspases are presumed responsible for the execution phase of apoptosis and typically rely on long prodomain caspases for initial proteolytic activation. Caspase-6 is a short prodomain caspase yet is activated before activation of any other caspase, including long prodomain caspases-8 or -9, during p84N5-induced apoptosis. The activation of caspase-6 is not likely to depend on caspase-9, because caspase-6 is a poor sub-strate for caspase-9 in vitro (Srinivasula et al., 1998). Caspase-8 is also unlikely to be involved, because an efficient caspase-8 peptide substrate is not cleaved by extracts of AdN5-treated cells and because p84N5-induced apoptosis is insensitive to CrmA (Doostzadeh-Cizeron et al., 1999), a potent inhibitor of caspase-8. Finally, caspase-3 is unlikely to be involved, because it is not required for p84N5-induced apoptosis. Caspase-6 is either activated by a protease whose activity has not been detected or is activated by a novel mechanism during p84N5-induced apoptosis. By analogy to other death domain-containing proteins, p84N5 may play an important part in caspase-6 activation. Thus, the inventors have characterized the apoptotic pathway triggered by the expression of the nuclear death domain-containing p84N5.

p84N5-induced apoptosis is characterized by activation of caspase-6, increases in the expression of Bcl-2 proapoptotic family members Bak and Bcl-Xs, and activation of NF-kB. Furthermore, this pathway does not require p53, nor does the presence of p53 affect the efficiency of cell killing. Expression of Rb, however, does inhibit p84N5-induced apoptosis, presumably mediated by physical association between the two proteins (Doostzadeh-Cizeron et al., 1999; Durfee et al., 1994). These observations, coupled with the fact that p84N5 is a death domain-containing protein localized within the nucleus, indicates that p84N5 participates in an apoptotic pathway that is different from those triggered by p53, death domain-containing receptors, or expanded polyglutamine repeat proteins.

Example 14

Adenovirus-mediated N5 Gene Transfer Inhibits Tumor Cell Proliferation by Induction of Apoptosis For gene therapy designed to initiate apoptotic cell death and provide a potentially effective methods to treat cancer a prerequisite is the identification of genes that function in distinct apoptotic pathways. Although apoptotic pathways initiated by receptors such as tumor necrosis factor receptor-1 are well characterized, little is known about apoptotic pathways initiated within the nucleus in response to genotoxic stress. Here the inventors test the usage of N5 for gene therapy of cancer. The inventors generated a recombinant adenovirus engineered to express N5 and tested the effects of viral infection on the growth and tumorigenicity of tumor cells. N5 adenovirus infection significantly reduced the proliferation and tumorigenicity of breast, ovarian, and osteosarcoma tumor cell lines. Reduced proliferation and tumorigenicity were mediated by an induction of apoptosis as indicated by DNA fragmentation in infected cells. Thus, N5 cDNA provides a tool for gene therapy of cancer.

N5 encodes a nuclear protein with an apparent molecular mass of 84 kDa.5 N5 protein (p84N5) contains a sequence similarity to the death domains of other proteins involved in the regulation of apoptosis. Transfection of N5 expression vectors can induce apoptotic cell death that is dependent upon an intact death domain and is inhibited by coexpression of Rb Furthermore, dominant interfering mutants of N5 inhibit the normal response of cells to ionizing radiation. As N5 is involved in a novel apoptotic pathway regulated by Rb and because defects in the RB regulatory pathway occur in many, if not all human tumors, N5 based gene therapy for cancer is envisioned. Thus, a recombinant adenovirus (AdN5) was designed to express N5 under control of the cytomegalovirus early promoter the effects of AdN5 infection on the growth and tumorigenicity of five tumor cell lines were examined.

Methods

Cell Lines and Cell Culture

All cell lines were obtained from the American Type Culture Collection (Manassas, Va.) and maintained in Dulbecco's modified Eagle's medium with 10% fetal bovine sera and antibiotics (100 U/mL penicillin, 100 mg/mL streptomycin) in a 5% CO2 incubator at 37° C. Recombinant adenovirus preparation and infection The recombinant p84N5 adenovirus is a modified serotype 5 adenovirus. The full-length N5 cDNA was cloned into the E1-deleted transfer vector pAdCMV(AS)-BGHpA (a gift of Dr. T. J. Liu, M D Anderson Cancer Center) containing the cytomegalovirus early promoter and bovine growth hormone polyadenylation signal. AdN5 was isolated by electroporation of the N5 transfer vector with pJM17 into 293 cells. The control wild-type (wt) RB and green fluores-cent protein (GFP)-expressing adenovirus were similarly constructed. Large scale viral preps were harvested from cells at 36–40 hours postinfection by resuspension in phosphate buffered saline (PBS) and lysis by freeze-thaw. Virus was purified from the cleared lysate by CsCl equilibrium density gradient centrifugation, and viral particles were quantitated by spectrophotometry. Infectious titer was estimated by an end point assay using the adenovirus direct immunofluorescence kit (Chemicon International, Temecula, Calif.). The concentrated virus was dialyzed against PBS plus 10% glycerol, aliquoted, and stored at −280° C. Infection was carried out by addition of the virus to the culture media and continued incubation at 37° C. for the desired length of time. Western blot analysis Infected cells were lysed in 50 mM tris (hydroxymethyl)aminomethane (Tris) (pH 7.4), 250 mM NaCl, 5 mM ethylenedia-minetetraacetic acid (EDTA), 0.1% Nonidet P-40, 50 mM NaF, 1 mM phenylmethylsulfonyl fluoride, and 1 mg/mL leupeptin on ice for 10 minutes. Cell debris was pelleted by centrifugation, and the total protein concentration of the soluble extract was determined by Bradford assay according to the manufacturer's instructions (Bio-Rad, Hercules, Calif.). A total of 17 mg of total protein for each sample was resolved by a 10% sodium dodecyl sulfate-polyacrylamide gel electro-phoresis gel. The proteins were transferred to a nitrocellulose membrane, and the membrane was blocked with 5% dry milk in PBS. The blot was stained with a mouse anti-human p84N5 monoclonal antibody (mAb)5 and mouse anti-human β-actin mAb. The blot was developed by enhanced chemiluminescence using a horseradish peroxidase-conjugated rabbit anti-mouse immunoglobulin G as described by the manufacturer (Amersham Life Science, Arlington Heights, Ill.).

Cell Growth Assay

Cells were plated at a density of $2 \times 10^4$ cells/mL in 12-well plates in triplicate. Cells were infected with either AdN5 or AdGFP at a multiplicity of infection (MOI) of 10 for all cell lines, except for the SKOV3 IP-1 cell line, which was infected at an MOI of 50. Cells were harvested at the indicated time intervals and stained with trypan blue; viable cells were counted using a hemocytometer. Tumorigenicity assays SKOV3 IP-1 cells were infected overnight at an MOI of 50 with AdN5 or AdGFP or were left untreated. U2OS cells were similarly infected at an MOI of 10. The cells were harvested by trypsinization, an aliquot of each sample was stained with trypan blue, and the number of viable cells was determined. One million cells of each sample were washed twice with PBS, and the cells in a final volume of 0.2 mL were injected subcutaneously (s.c.) into the flanks of nude mice. Tumor formation was evaluated weekly for 5 weeks. At least six mice were injected for each sample. Tumor volumes were estimated by measuring the diameter of the resulting tumors in three dimensions. DNA fragmentation analysis after infection with AdN5 or AdGFP for 5 days, cells were collected and resuspended in 0.1 mL of PBS, to which 1 mL of extraction buffer (10 mM Tris (pH 8.0), 0.1 M EDTA, 20 mg/mL ribonuclease, 0.5% SDS) was added before incubation at 37° C. for 1–2 hours. Proteinase K was then added to a final concentration of 100 mg/mL and the samples were incubated for an additional 3 hours at 50° C. NaCl was added to bring up the final NaCl concentration to 1 M, and the samples were incubated overnight at 4° C. The high molecular weight DNA was pelleted by centrifugation for 1 hour at 57,000 3 g. The supernatant was extracted once with an equal volume of 0.5 M Tris (pH 8.0)-saturated phenol and then again with phenol/chloroform. The precipitated DNA was resolved by a 1% agarose gel and stained with ethidium bromide.

Results

Figure 24:
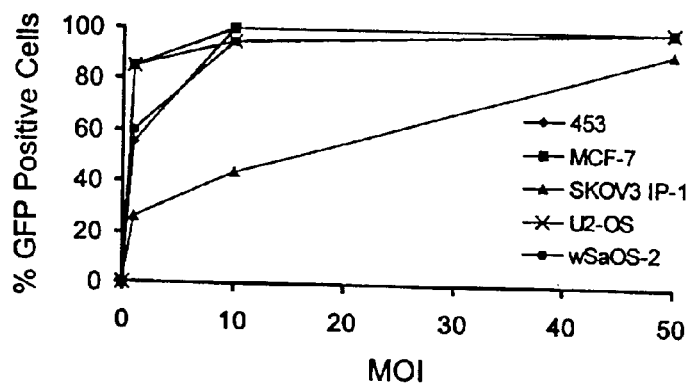
FIG. 24. Efficiency of adenoviral-mediated gene transduction in various cancer cell lines. MDA-MB-453, MCF-7, SKOV3 IP-1, U2OS, and SAOS2 cells were treated with AdGFP at MOIs ranging from 1 to 100 as indicated. The percentage of GFP-positive cells was scored for each sample by fluorescence microscopy. At least 100 total cells were counted in at least three randomly selected fields of view to determine the percentage of GFP-positive cells. The results presented are the mean of three independent infections.

Five tumor cell lines were used to study the effects of AdN5 infection: two breast carcinoma lines (MCF-7 and MDA-MB-453), an ovarian carcinoma line (SKOV3 IP-1), and two osteosarcoma cell lines (SAOS-2 and U2OS). To test the sensitivity of these cell lines to adenoviral infection, each cell line was treated with varying numbers of infectious, recombinant virus designed to express GFP (AdGFP). The percentage of infected cells was determined the following day by fluorescence microscopy. At an MOI of 10, 0.90% of MDA-MB-453, MCF-7, U2OS, or SAOS-2 cells expressed detectable GFP (FIG. 24). An MOI of 50 was required to observe similar levels of infection in SKOV3 IP-1 cells. For all subsequent experiments, an MOI of 50 was used to treat SKOV3 IP-1 cells, whereas an MOI of 10 was used to treat the remaining cell lines. Because the infectious titer of both AdGFP and AdN5 viral stocks was determined by infection of 293 cells (see Methods), the gene transduction efficiency for each of the viruses in each of the cell lines should be similar.

Figure 25:
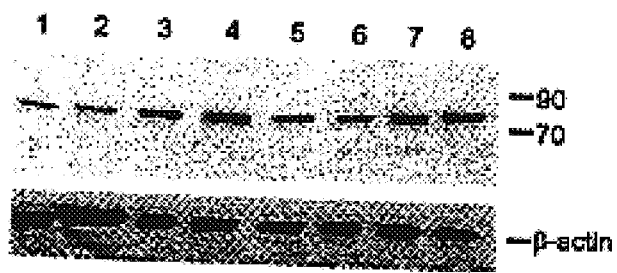
FIG. 25. Expression of p84N5 on AdN5 infection. The level of p84N5 expression after treatment was determined by Western blotting. Uninfected cells (lanes 1 and 5), cells at 24 hours after infection with AdGFP (lanes 2 and 6) or AdN5 (lanes 3 and 7), and cells at 48 hours after infection with AdN5 (lanes 4 and 8) were extracted; next, 17 mg of total protein from the cleared lysates was resolved by 10% SDS-PAGE, blotted to nitrocellulose, and probed with an antibody specific for N5 protein or a mouse anti-β-actin mAb. The position of molecular weight standards and β-actin are indicated.
Figure 26:
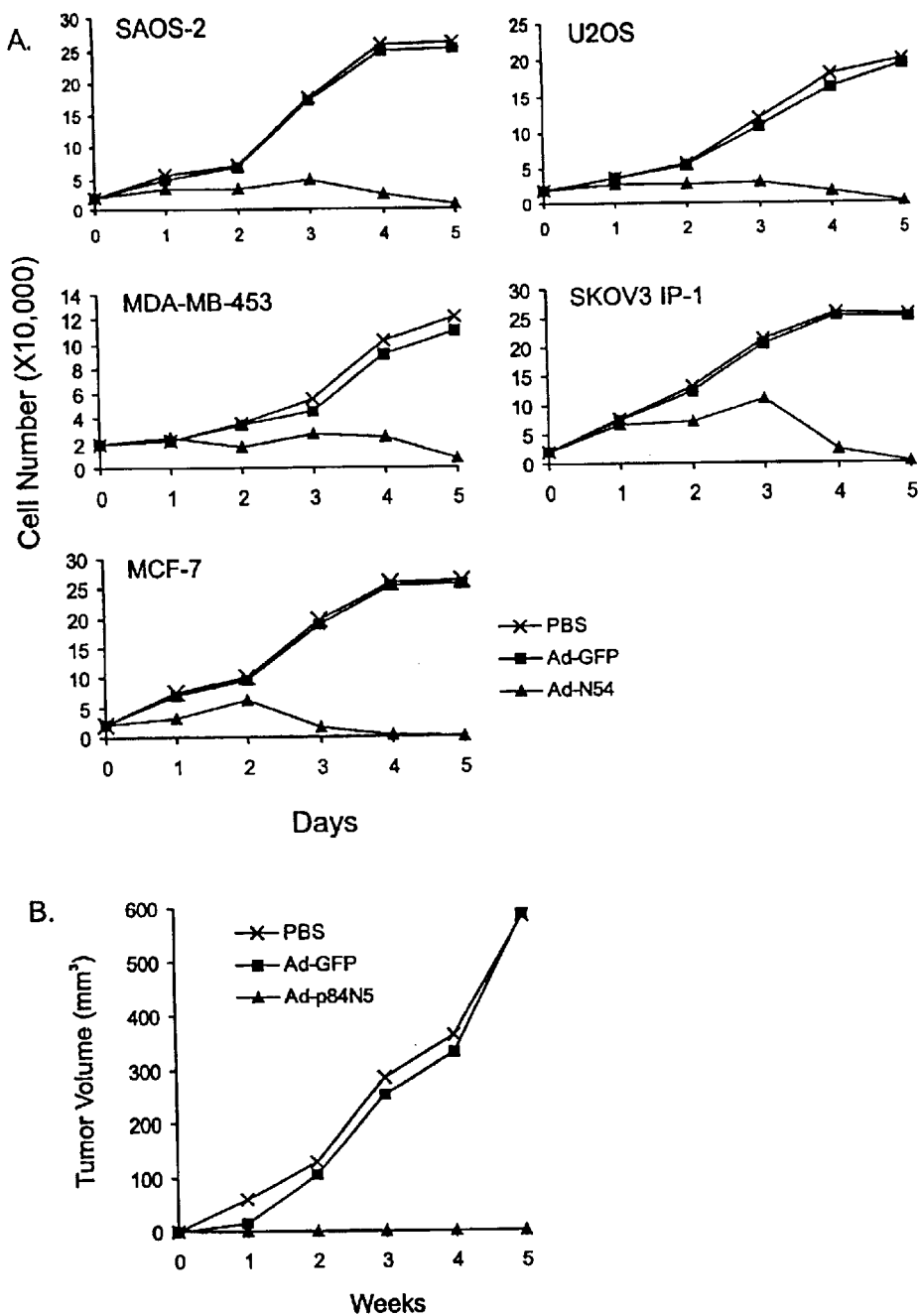
FIG. 26A. & FIG. 26B. AdN5 inhibits tumor cell proliferation in vitro and in vivo.
FIG. 26B. SKOV3 IP-1 cells were treated with AdN5 or AdGFP at an MOI of 50 or mock-infected with PBS. After an overnight infection, cells were washed and one million viable cells were injected s.c. into the flanks of nude mice. Tumor formation was evaluated weekly for 5 weeks. Tumor volumes were estimated by measuring the diameter of the resulting tumors in three dimensions. The data presented represent the mean of at least six mice for each treatment. All six mice injected with AdN5-treated cells were tumor-free for the entire 5 weeks of the study.

The level of p84N5 expression was characterized after treatment with AdN5 or AdGFP by Western blot analysis of protein extracts from treated SKOV3 IP-1 or U2OS cells (FIG. 25). An equal mass of total cell protein from each sample was resolved by SDS-PAGE and blotted; the Western blots were stained with a mAb specific for p84N5 or β-actin. The amount of p84N5 detected in untreated or AdGFP-treated cells of both cell lines was approximately the same relative to the β-actin loading control, indicating that AdGFP infection did not alter p84N5 expression. However, AdN5-infected U2OS or SKOV3 IP-1 cells contained 2- to 3-fold more p84N5 by 24 hours postinfection. This level of expression increased slightly by 48 hours postinfection. To determine the effect of AdN5 infection and increased p84N5 expression on the proliferation of each cell line in vitro, growth curves were measured for each of the five cell lines treated with AdN5, AdGFP, or PBS. Infection with AdN5 inhibited the cell proliferation of each cell line (FIG. 26A). By the day 2 postinfection, lower numbers of cells were consistently observed in cells treated with AdN5. The cell number in AdN5-treated cultures remained relatively constant until day 3 or day 4, at which point the cell number declined. By day 5, few viable cells treated with AdN5 remained. In contrast, cells treated with PBS or AdGFP continued to proliferate until reaching confluency around day 5. Treatment of cells with AdGFP had no detectable effect on cell proliferation relative to PBS cells. The effect of AdN5 infection on the tumorigenicity of SKOV3 IP-1 and U2OS in nude mice was also examined. Viable cells infected with AdN5 or AdGFP for 16 hours were injected s.c. into the flanks of nude mice. Both AdGFP-and PBS-treated SKOV3 IP-1 cells formed large tumors that were readily detectable by 2 weeks postinjection (FIG. 26B). Tumor volume increased exponentially over time.

Figure 27A:
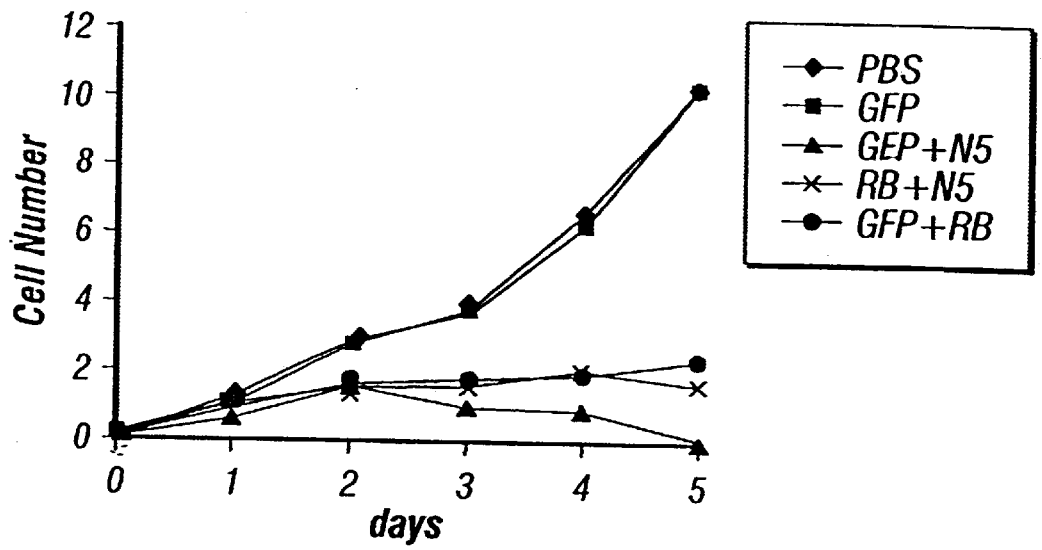
FIG. 27A & FIG. 27B. Coexpression of RB inhibits AdN5-induced cell death.
Figure 27B:
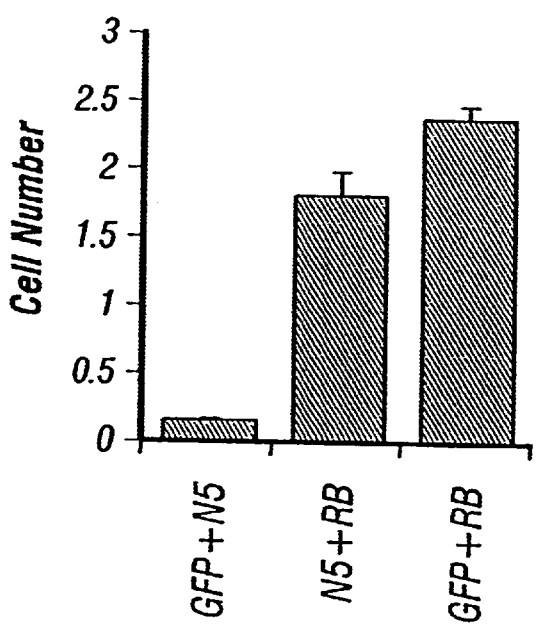
Figure 28:
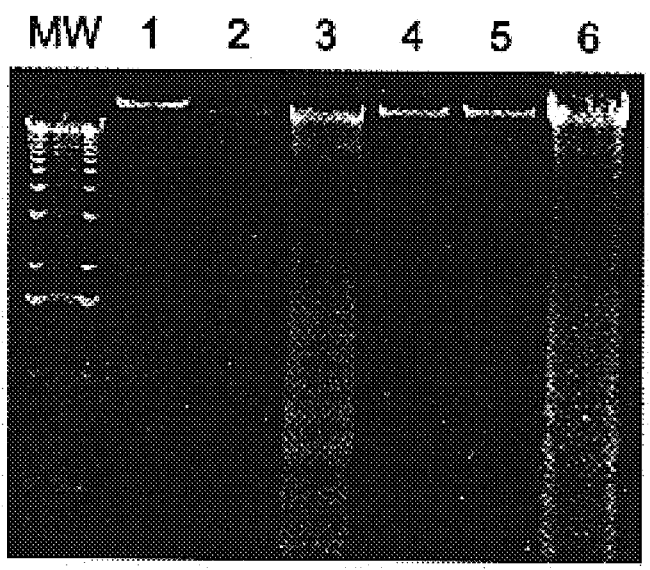
FIG. 28. AdN5-infected cells contain fragmented DNA. SKOV3 IP-1 cells (lanes 1–3) or U2OS cells (lanes 4–6) were treated with PBS (lanes 1 and 4), AdGFP (lanes 2 and 5), or AdN5 (lanes 3 and 6) at MOIs of 50 or 10, respectively. After 5 days, cells were collected and resuspended in 0.1 mL of PBS to which 1 mL of 10 mM Tris (pH 8.0), 100 mM EDTA, 20 mg/mL ribonuclease, and 0.5% SDS was added before incubation at 37° C. for 1–2 hours. Proteinase K was then added to a final concentration of 100 mg/mL and incubation continued at 50° C. for at least 3 hours. NaCl was added to a final concentration of 1 M and the samples were incubated at 4° C. overnight. High molecular weight DNA was pelleted by ultracentrif-ugation for 1 hour at 57,000 3 g. The supernatant was extracted once with an equal volume of 0.5 M Tris (pH 8.0)-saturated phenol and then again with phenol/chloroform. The DNA was ethanol-precipitated and analyzed in a 1% agarose gel. A 1-kbp DNA ladder served as the molecular weight (MW) marker.

Consistent with the in vitro proliferation data, no tumor growth could be detected in SKOV3 IP-1 cells treated with AdN5 even after 5 weeks. At this time, the tumor volume of AdGFP-infected cells reached 600 mm. Similar results were observed in U2OS cells. The tumor volume of AdGFP and PBS-treated U2OS cells reached a maximum of 43 mm, whereas no tumor growth could be detected in AdN5-infected cells. The inventors previous work had indicated that transfection of p84N5 expression vectors could inhibit cell proliferation by induction of apoptosis, and that coexpression of RB blocked this effect. The cell lines examined here vary with respect to expression of endogenous RB. For example, MCF-7 and U2OS express wt RB but SAOS-2 does not. Yet each of these cell lines is equally sensitive to AdN5. This may be due to the relative levels of p84N5 versus RB expression in AdN5-treated cells. To examine this possibility, the inventors measured the proliferation of cells treated with AdN5 and a recombinant adenovirus de-signed to express RB protein. Cells treated with PBS or AdGFP proliferate exponentially, whereas AdN5-treated cells proliferate slower until day 3, at which point cell numbers begin to decline. Like AdN5-treated cells, cells treated with both AdN5 and AdRB proliferate slower initially (FIG. 27A). However, the number of AdN5-plus AdRB-treated cells does not decline at later times like cells treated with AdN5 alone (FIG. 27B). Treatment of cells with AdRB alone also causes cell proliferation to slow substantially, consistent with the documented ability of RB protein to induce cell cycle arrest.

To determine whether AdN5 infection, like N5 gene transfection, inhibited tumor cell proliferation by induction of apoptotic cell death, DNA was extracted from cells 4 or 5 days after infection with AdN5, AdGFP, or PBS. The DNA was resolved by agarose gel electrophoresis and stained with ethidium bromide. DNA fragmentation resulting in laddering, which is characteristic of cells undergoing apoptosis, was observed in AdN5-infected cells, but not in cells treated with AdGFP or PBS (FIG. 27). Using a terminal deoxytransferase end labeling reaction, the inventors have determined that 80% of cells treated with AdN5 contain fragmented DNA at 3 days postinfection, whereas only 7% of AdGFP-infected cells contain fragmented DNA. The morphology of AdN5-infected cells at this time was also consistent with induction of apoptosis. Relative to AdGFP-infected cells, AdN5-infected cells exhibit a condensed and rounded morphology before detaching from the culture dish.

Discussion

The inventors demonstrate by means of this example that adenovirus-mediated N5 gene transfer can increase the expression of p84N5. The increase in p84N5 expression is modest relative to that achievable with other proteins using similarly constructed recombinant adenovirus. This observation may, in part, be due to the fact that p84N5 is likely targeted for degradation during the induction of apoptosis. Cells expressing high levels of p84N5, therefore, are triggered to undergo apoptosis, resulting in p84N5 degradation and in decreased levels of detectable p84N5. Indeed, examination of p84N5 expression in AdN5 infected cells at 3–4 days postinfection, when most cells are undergoing apoptosis, reveals lower levels of p84N5 than uninfected cells. The increase in p84N5 expression upon AdN5 infection is sufficient to inhibit the proliferation of several different types of tumor cells both in vitro and in vivo.

Inhibition of cell proliferation is not a consequence of adenoviral infection itself, because treatment of cells with AdGFP had no detectable effect on cells relative to mock infected cells. The block to tumor cell proliferation observed upon AdN5 infection is due, at least in part, to induction of apoptotic cell death as indicated by morphology and the presence of fragmented DNA. However, the inventors observed that treatment of cells with AdN5 causes a transient G2/M cell cycle arrest by day 2 postinfection that precedes the onset of apoptosis as measured by DNA fragmentation. This observation may explain the initial cytostatic effect of AdN5 that is followed by apoptosis. Therefore, N5-induced apoptosis may be a late event that follows a G2/M block to cell cycle progression. This behavior is similar to cellular responses to ionizing radiation.

The inventors have also shown that coexpression of RB can inhibit N5-induced apoptosis, and that their physical association mediates this block. However, all the cell lines tested here are sensitive to AdN5 yet vary in their RB status. For example, MCF-7 and U2OS cells contain apparently wt RB yet are as sensitive to AdN5 as cells lacking RB, such as SAOS-2 and SKOV3 IP-1. This apparent contradiction may be explained by the fact that sufficient endogenous RB protein is not expressed in these cells lines to block the apoptosis triggered by AdN5-mediated p84N5 expression. Consistent with this, treatment of cells with AdN5 and AdRB inhibits cell proliferation but delays the rapid decline in cell numbers that occurs in cells treated with AdN5 alone. This observation is consistent with the explanation that RB expression inhibits AdN5-induced apoptosis and cell proliferation due to its well characterized ability to induce cell cycle arrest. Therefore, cells with wt RB protein, including noncancerous cells, may be less sensitive to AdN5 than RB-negative tumor cells.

Example 15
Apoptosis Induced by the Nuclear Death Domain Protein p84N5 is Inhibited by Association with Rb Protein The Rb protein inhibits both cell cycle progression and apoptosis. Interaction of specific cellular proteins, including E2F1, with Rb C-terminal domains mediates cell cycle regulation. In contrast, the nuclear N5 protein associates with an Rb N-terminal domain with unknown function. The N5 protein contains a region of sequence similarity to the death domain of proteins involved in apoptotic signaling. The inventors demonstrate by means of this example that forced N5 expression potently induces apoptosis in several tumor cell lines. Mutation of conserved residues within the death domain homology compromise N5-induced apoptosis, indicating that it is required for normal function. Endogenous N5 protein is specifically altered in apoptotic cells treated with ionizing radiation. Furthermore, dominant interfering death domain mutants compromise cellular responses to ionizing radiation. Finally, it is demonstrated that physical association with Rb protein inhibits N5-induced apoptosis.

The C-terminal half of p110Rb is sufficient for many of its known molecular activities, including modulation of transcription factor function and induction of cell cycle arrest. The purpose of the N-terminal half of p110Rb is undefined. Several observations suggest that this region may be important for normal function. First, some mutations causing low-penetrance retinoblastoma specifically alter the N-terminal half of the protein (Dryja et al., 1993; Hogg et al., 1993; Lohmann et al., 1994). Second, the amino acid sequence of the N-terminal half of p110Rb is conserved between mouse, rat, chicken, frog, newt, and human. Finally, N-terminally truncated Rb transgenes are incapable of rescuing developmental defects observed in mice deficient in wild-type Rb (Riley et al., 1997).

To discover a role for this region of p110Rb, the N5 gene was isolated on the basis of its ability to encode a protein that specifically associates with the N-terminal half of p110Rb (Durfee et al., 1994). Three other proteins, a 70-kDa heat-shock protein (Inoue et al., 1995), a kinase (Sterner et al., 1996), and MCM7 (Sterner et al., 1998), have been discovered to bind the N-terminal half of p110Rb. The relevance of these interactions for Rb function is not completely understood, although association of p110Rb with MCM7 does inhibit DNA replication in vitro (Sterner et al., 1998). The N5 protein (p84N5) is normally localized exclusively to the nucleus during interphase and has a region of structural similarity to the death domains of several well characterized proteins involved in apoptosis, including tumor necrosis factor receptor 1 (TNFR-1) (Feinstein et al., 1995). The role of p84N5 is involved in regulating apoptosis and that Rb may modulate this activity through physical association with p84N5. The inventors demonstrate that forced expression of p84N5 potently induces apoptosis, that an intact death domain is required for this effect, that p84N5 is normally modified during apoptosis, that dominant interfering N5 mutants compromise cellular responses to ionizing radiation, and that physical association with p110Rb inhibits p84N5-mediated apoptosis. These findings suggest that Rb may have a direct role in the regulation of apoptosis through the inhibition of a novel nuclear death domain protein.

Furthermore, inhibition of p84N5-induced apoptosis identifies a novel function requiring the N-terminal domain of p110Rb. Because p84N5 is unique among death domain proteins in being localized exclusively to the nucleus, the study of p84N5 may uncover novel apoptotic signaling mechanisms within the nucleus. The inventors propose that Rb has a direct role in coordinating apoptosis and the cell cycle by interaction with distinct cellular proteins that affect each process.

Methods

Cell Culture

SAOS-2, 5637, and 293 cell lines were obtained from American Type Culture Collection (Manassas, Va.) and maintained in DMEM with 10% heat-inactivated fetal bovine serum and antibiotics (100 U/ml penicillin, 100 mg/ml streptomycin) in a 5% CO2 incubator at 37° C.

Plasmids

The cDNAs encoding p84N5 were subcloned into the pCEP4 expression vector (Invitrogen, San Diego, Calif.) to create pCMVN5. The p35 (Clem and Miller, 1994), Bcl-2 (McDonnell et al., 1990), p110Rb, and p110RbDCdk (Leng et al., 1997) cDNAs were also expressed under control of the cytomegalovirus promoter in pCDNA3.1 (p110RbDCdk) or pCMV (p35, Bcl-2). PCR-based site-directed mutagenesis was performed as previously described (Fisher and Pei, 1995). The template for PCR mutagenesis was the complete N5 cDNA inserted into pBSK (Stratagene, La Jolla, Calif.). The N5-PP mutant was created using the following pair of adjacent phosphorylated primers: N5DD1.2 (59-CT TGA TCT TGC SRG GCA ACC RSG AGC TGC TTA GC-39, SEQ ID NO: 3) and N5A4R (59-AG GGA GTT CAT GCA ACA CCT G-39, SEQ ID NO: 4). The N5Da4 deletion mutant was created with the phosphorylated primers NSA4F (59-TCA TGT CTT CAC TGT CAC ACT-39, SEQ ID NO: 5) and N5A4R. Mutagenesis creates an in-frame deletion of nucleotides 1843–1884 of the N5 cDNA. The Sculptor in vitro mutagenesis system (Amersham, Arlington Heights, Ill.) was used according to manufacturer's specifications to create the N5-R mutant. The HindIII to BamHI N5 fragment from pCMVN5 was inserted into M13mp19 and served as the single-strand DNA template for mutagenesis. The N5DD1.2 oligonucleotide was used as the primer. The mutations were confirmed by sequence analysis using the Thermo Sequenase radiolabeled terminator cycle sequencing kit according to manufacturer's recommendations (Amersham).

Transfection Assays

SAOS-2, 5637, or 293 cells were seeded in 100-mm dishes the day before transfection. Cells were transfected by the calcium phosphate precipitation method (Wigler et al., 1979) using 6–30 mg of total DNA. For cotransfections, 6 mg of pCMVN5 and 24 mg of Bcl-2, p35, pCrmA, or pRb were used. Subsequent to transfection, attached and detached cells were collected separately at the indicated times. Cell viability was assessed by trypan blue staining in each cell population. Cell populations were then pooled and analyzed further. β-Gal activity in transfected cells was visualized subsequent to fixation with 5% glutaraldehyde in PBS for 15 min followed by extensive washing in PBS containing 5 mM MgCl2. Cells were stained in PBS containing 20 mM K3 Fe(Cn)6, 20 mM K4 Fe(Cn)6 3H2 O, 1 mM MgCl2, and 1 mg/ml X-Gal (5-bromo-4-chloro-3-indoyl-b-d-galactopyranoside) until a suitable color developed, usually after ~6–12 h. Fragmented DNA was extracted from ~$10^7$ cells transfected with either pCMVN5 or pCMV in 10 mM Tris-HCl, pH 8.0, 10 mM EDTA, 0.5% Triton X-100. The lysate was clarified by centrifugation, and the cleared lysate was treated with RNase A (50 mg/ml) for 1 h at 37° C. This was followed by proteinase K treatment (100 mg/ml) in 0.5% SDS for 2 h at 50° C. The DNA solution was extracted with phenol/chloroform, and DNA was precipitated in EtOH. DNA was dissolved in 10 mM Tris, 1 mM EDTA in preparation for electrophoresis on a 1.8% agarose gel. DNA fragmentation was also as-sayed after transfection with the indicated expression vectors by labeling free DNA ends with terminal deoxytransferase (TUNEL). Cells were collected by trypsin-EDTA treatment, washed two times with PBS, and stained by TUNEL using the APO-DIRECT kit (Phoenix Flow Systems, San Diego, Calif.) according to manufacturer's directions. Flow cytometry analysis was performed on FACSCalibur instrument (Becton Dickinson, San Jose, Calif.). Clonogenicity assays were performed by transfection of 10 mg of the indicated plasmid along with 3 mg of pEGFP-C1 (Clontech, Palo Alto, Calif.). One day after transfection, cells were examined by fluorescence microscopy for green fluorescent protein (GFP)-positive cells to ensure that transfection had been successful. Transfection of pCMVN5 typically gave 30–50% of the GFP-positive cells that were observed with pCMV. Cultures were then incubated for an addi-tional 2 wk in the presence of 500 mg/ml G418 (Sigma, St. Louis, Mo.). After G418 selection, the number of GFP-positive colonies with >20 cells was determined per 100× microscope field under fluorescence microscopy. To assess the effects of N5 death domain mutants on sensitivity to ionizing radiation, SAOS-2 (SD8) cells, a subline of SAOS-2 cells, were transfected as above with the death domain mutant expression vectors and pEGFP-C1. One day after transfection, viable successfully transfected cells were collected by FACS (Becton Dickinson FACS Vantage) based on GFP fluorescence, and 7000 cells were plated per well of a 96-well plate. The following day, cells were treated with 0 or 20 Gy radiation from a Nasatron $^{137}$Cs irradiator (US Nuclear, Burbank, Calif.). Two days after irradiation, the relative number of remaining viable cells was determined by XTT (sodium 39-[1-(phenylamino-carbonyl)-3,4-tetrazolium]-bis-(4-methoxy-6-nitro)benzene sulfonic acid hydrate) assay according to manufacturers instructions (Boehringer Mannheim, Indianapolis, Ind.). The data are presented as the ratio of the $OD_{490}$ of treated versus untreated cells.

Microinjection

The N5 GST fusion protein was produced as described (Durfee et al., 1994). The fusion protein was eluted in PBS plus 5 mM glutathione and then dialyzed against 25 mM Tris, pH 7.2, 25 mM KCl, 2% glycerol in preparation for injection. The p110Rb and p56Rb were produced and purified as previously described (Connell-Crowley et al., 1997). The protein concentration of the injected samples is indicated by FIG. 34C. Injection was performed directly on cells growing on 35-mm culture dishes using an Eppendorf micromanipulator with femtotip capillary micropipettes. The injection pressure used was between 50 and 100 hPa with an injection time of 0.3–0.5 s. Apoptotic cells were detected 90 min after injection by observation of characteristic morphological changes under phase-contrast microscopy and by staining with the DNA binding fluorochrome bis-(benzimide)-trihydrochloride (Hoechst 33342; Sigma) and fluo-rescent microscopy as described previously (Ormerod et al., 1993).

Western Blotting

Transfected or treated cells were extracted in a buffer containing 50 mM Tris, pH 7.4, 250 mM NaCl, 5 mM EDTA, 0.1% NP-40, 50 mM NaF, 1 mM PMSF, 1 mg/ml leupeptin on ice for 10 min. Cell debris was pelleted by microcentrifugation, and the total protein concen-tration of the soluble extract was determined by Bradford assay according to manufacturers instructions (Bio-Rad, Hercules, Calif.). Total soluble protein (70 mg) for each sample was loaded on 10% SDS-polyacrylamide gel. After electrophoresis, the proteins were transferred to nitrocellulose, and the blot was blocked with a solu-tion of 10% dried milk powder in TTBS (100 mM Tris, pH 7.5, 150 mM NaCl, 0.1% Tween 20) for 1 h at room temperature. The blot was incubated with primary antibody diluted in fresh TTBS for 1 h at room temperature or 4° C. overnight. Primary antibody was detected using a peroxidase-conjugated secondary antibody and enhanced chemilumi-nescence as described by the manufacturer (Amersham).

Immunofluorescent Staining

SAOS-2 cells were seeded onto chamber slides 2 d before irradia-tion. Cells were irradiated with the indicated dose of g-irradiation, and incubation was continued for 3 d before fixation in 100% ice-cold MeOH. Fixed cells were washed in PBS and blocked with TTBS 15% dry milk. Fixed cells were incubated with primary antibody diluted in TTBS for 1 h atroom temperature. After washing, cells were incubated with FITC-conjugated secondary antibody (Vector Labs, Burlingame, Calif.) diluted in TTBS 11 mg/ml Hoechst 33342. After washing, slides were mounted with Vectashield (Vector Labs) before photography under fluorescence microscopy.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Agah, Kirshenbaum, Abdellatif, Truong, Chakraborty, Michael, Schneider, "Adenoviral delivery of E2F-1 directs cell cycle reentry and p53-independent apoptosis in postmitotic adult myocardium in vivo," *J.Clin.Invest.*, 100: 2722–2728, 1997.

An and Dou, "Cleavage of retinoblastoma protein during apoptosis: an interleukin 1 beta-converting enzyme-like protease as candidate," *Cancer Res.* 56, 438–442, 1996.

Arcone, et al., *Nucl. Acids Res.,* 16(8): 3195–3207, 1988.

Bagchi, Weinmann, and Raychaudhuri, "The retinoblastoma protein copurifies with E2F-I, an E1A-regulated inhibitor of the transcription factor E2F," *Cell* 65, 1063–1072, 1991.

Baichwal and Sugden, In: *Gene Transfer,* Kucherlapati R, ed., New York, Plenum Press, pp. 117–148, 1986.

Bartlett et al., *Proc. Nat'l Acad. Sci. USA,* 93:8852–8857, 1996.

Bennett, Macdonald, Chan, Luzio, Simari, Weissberg, *Science* 282:290–293, 1998.

Benvenisty and Neshif, *Proc. Nat'l Acad. Sci. USA,* 83:9551–9555, 1986.

Blasina, Price, Turenne, McGowan, *Curr.Biol.* 9:1135–1138, 1999.

Boise, Gonzalez-Garcia, Postema, Ding, Lindsten, Turka, Mao, Nunez, Thompson, *Cell,* 74:597–608, 1993.

Boldin et al., *J. Biol. Chem.* 270:387–391, 1995.

Bookstein, Rio, Madreperia, Hong, Allred, Grizzie, Lee, "Promoter deletion and loss of retinoblastoma gene expression in human prostate carcinoma," *Proc. Nat'l Acad. Sci. USA.* 87:7762–7766, 1990a.

Bookstein, Shew, Chen, Scully Lee, "Suppression of tum-origenicity of human prostate carcinoma cells by replacing a mutated Rb gene," *Science* 247,712–715, 1990b.

Buchkovich, Duffy, Harlow, "The retinoblastoma protein is phosphorylated during specific phase of the cell cycle," *Cell* 58, 1097–1105, 1989.

Carter and Flotte, *Ann. N.Y. Acad. Sci.,* 770:79–90, 1995.

Chandar, Billig, McMaster, and Novak, "Inactivation of p53 gene in human and murine osteosarcoma cells," *Br. J. Cancer* 65, 208–214, 1992.

Chatterjee, et al., *Ann. N.Y. Acad. Sci.,* 770:79–90, 1995.

Chen and Okayama, *Mol. Cell Biol.,* 7:2745–2752, 1987.

Chen, Chen, Arnaiz, Goodrich, Lee, *Oncogene* 6:1799–1805, 1991.

Chen, Chen, Shan, Bookstein, Lee, "Stability of Rb expression determines the tumorigenicity of reconstituted ret-inoblastoma cells," *Cell Growth Diff.* 3,119–125, 1992.

Chen, Scully, Shew, Wang, Lee, "Phosphorylation of the retinoblastoma gene product is modulated during the cell cycle and cellular differentiation," *Cell* 58, 1193–1198, 1989.

Chiao, Miyamoto, Verma, *Proc. Natl. Acad. Sci. U.S.A.* 91:28–32, 1994.

Chittenden, Harrington, O'Connor, Flemington, Lutz, Evan, Guild, *Nature* 374:733–736, 1995.

Clem and Miller, "Control of programmed cell death by the baculovirus genes p35 and iap," *Mol. Cell. Biol.* 14, 5212–5222, 1994.

Cleveland and Ihle, *Cell* 81:479–482, 1995.

Coffin, In: *Virology,* ed., New York: Raven Press, pp. 1437–1500, 1990.

Connell-Crowley, Harper, and Goodrich, "Cyclin D1/Cdk4 regulates retinoblastoma protein-mediated cell cycle arrest by site-specific phosphorylation," *Mol. Biol. Cell* 8, 287–301, 1997.

Coupar et al., *Gene,* 68:1–10, 1988.

Cregan, MacLaurin, Craig, Robertson, Nicholson, Park, Slack, *J. Neurosci.,* 19:7860–7869, 1999.

Dani, et al., *J. Biol. Chem.,* 264:10119–10125, 1989.

Darbon, Penary, Escalas, Casagrande, Goubin-Gramatica, Baudouin, Ducommun, *J.Biol.Chem.,* 275:15363–15369, 2000.

Datta, Kojima, Banach, Bump, Talanian, Alnemrik, Weichselbaum, Wong., and Kufe, "Acitvation of a CrmA-insensitive, p35-sensitive pathway in ionizing radiation-induced apoptosis," *J. Biol. Chem.* 272, 1965–1969, 1997.

DeCaprio, Ludlow, Figge, Shew, Huang, Lee, Marsillo, Paucha, Livingston, "SV40 large tumor antigen forms a specific complex with the product of the retinoblastoma susceptibility gene," *Cell* 54, 275–283, 1988.

DeCaprio, Ludlow, Lynch, Furukawa, Griffin, Pawnica-Worms, Huang, Livingston, "The product of the retino-blastoma susceptibility gene has properties of a cell cycle regulatory element," *Cell* 58,1085–1095, 1989.

Defeo-Jones, Huang, Jones, Haskell, Vuocolo, Hanobik, Huber, Oliff, "Cloning of cDNAs for cellular proteins that bind to the retinoblastoma gene product," *Nature* 352, 251–254, 1991.

Descamps, Duffour, Mathieu, Fernandez, Cordier, Abina, Kremer, Perricaudet, Haddada, "Strategies for cancer gene therapy using adenoviral vectors," *J.Mol.Med.*, 74, 183–189, 1996.

Devary, Rosette, DiDonato, Karin, *Science* 261, 1442–1445, 1993.

Doostzadeh-Cizeron and Goodrich, *J.Biol.Chem.*, 2000.

Doostzadeh-Cizeron, Evans, Yin, Goodrich, *Mol. Biol. Cell*, 10:3251–3261, 1999.

Dryja, Rapaport, McGee, Nork, and Schwartz, "Molecular etiology of low-penetrance retinoblastoma in two pedigrees," *Am. J. Hum. Genet.* 52, 1122–1128, 1993.

Dubensky et al., *Proc. Nat'l Acad. Sci. USA*, 81:7529–7533, 1984.

Durfee, Mancini, Jones, Elledge, and Lee, "The amino-terminal region of the retinoblastoma gene product binds a novel nuclear matrix protein that co-localizes to centers for RNA processing," *J. Cell Biol.*, 127, 609–622, 1994.

Dyson, Howley, Munger Harlow, "The human papilloma virus-16 E7 oncoprotein is able to bind to the retinoblastoma gene product," *Science* 243, 934–937, 1989.

Ellis, Yuan, Horvitz, *Annu. Rev. Cell Biol.*, 7:663–698, 1991.

Fechheimer et al., *Proc. Nat'l Acad. Sci. USA*, 84:8463–8467, 1987.

Feinstein, Kimchi, Wallach, Boldin, and Varfolomeev, "The death domain: a module shared by proteins with diverse cellular functions," *TIBS* 20, 342–344, 1995.

Ferkol et al., *FASEB J.*, 7:1081–1091, 1993.

Ferrari et al., *J. Virol.*, 70:3227–3234, 1996.

Fischer, Huber, Boelens, Mattaj, Luhrmann, *Cell*, 82:75–483, 1995.

Fisher and Pei, "Modification of a PCR-based site-directed mutagenesis method," *Biotechniques* 23, 570–571, 1995.

Fisher and Pei, *Biotechniques*, 23:570–574.14, 1997.

Fisher et al., *J. Virol.*, 70:520–532, 1996.

Flemington, Speck, and Kaelin, "E2F-1-mediated transactivation is inhibited by complex formation with the retinoblastoma susceptibility gene product," *Proc. Nat'l Acad. Sci. U.S.A.* 90, 6914–6918, 1993.

Flotte et al., *Proc. Nat'l Acad. Sci. USA*, 90:10613–10617, 1993.

Fraley et al., *Proc. Nat'l Acad. Sci. USA*, 76:3348–3352, 1979.

Friedmann, "Progress toward human gene therapy," *Science*, 244:1275–1281, 1989.

Friend, Bernards Rogelj, Weinberg, Rapaport, Albert, Dryja, "A human DNA segment with properties of the gene that predisposes to retinoblastoma and osteosarcoma," *Nature* (London) 323, 643–646, 1986.

Fung, Murphree, Tang, Qian, Hinrichs, Benedict, "Structural evidence for the authenticity of the human retinoblastoma gene," *Science* 236, 1657–1661, 1987.

Ghosh and Bachhawat, In: *Liver diseases, targeted diagnosis and therapy using specific receptors and ligands*, (Wu G, Wu C ed.), New York: Marcel Dekker, pp. 87–104, 1991.

Goodman et al., *Blood*, 84:1492–1500, 1994.

Goodrich and Lee, "Molecular characterization of the retinoblastoma susceptibility gene," *Biochim. Biophys. Acta.* 1155, 43–61, 1993.

Goodrich, Chen, Scully, Lee, "Expression of the retinoblastoma gene product in bladder carcinoma cells associates with a low frequency of tumor formation," *Can. Res.* 52, 1968–1973, 1992.

Goodrich, Wang, Qian, Lee, and Lee, "The retinoblastoma gene product regulates progression through the G1 phase of the cell cycle," *Cell* 67, 293–302, 1991.

Gopal, *Mol. Cell Biol.*, 5:1188–1190, 1985.

Gossen and Bujard, *Proc. Nat'l Acad. Sci. USA*, 89:5547–5551, 1992.

Gossen et al., *Science*, 268:1766–1769, 1995.

Graham and Van Der Eb, *Virology*, 52:456–467, 1973.

Gross, McDonnell, Korsmeyer, *Genes Dev.* 13:1899–1911, 1999.

Haas-Kogan, Kogan, Levi, Dazin, T'Ang, Fung, and Israel, "Inhibition of apoptosis by the retinoblastoma gene product," *EMBO J.* 14, 461–472, 1995.

Haimovitz-Friedman, *Rad.Res.* 150:S102–S108, 1998.

Harbour, Lai, Whang-Peng, Gazdar, Minna, Kaye, "Abnormalities in structure and expression of the human retinoblastoma gene in SCLC," *Science* 241; 353–357, 1988.

Harris, *Cancer Surv.*, 4:601–624.16, 1985.

Harris, Sutjipto, Wills, Hancock, Cornell, Johnson, Gregory, Shepard, Maneval, "Adenovirus-mediated p53 gene transfer inhibits growth of human tumor cells expressing mutant p53 protein," *Cancer Gene Ther.*, 3: 121–130, 1996.

Haupt, Rowan, and Oren, "p53-mediated apoptosis in HeLa cells can be overcome by excess pRb," *Oncogene* 10, 1563–1571, 1995.

Hay et al., *J. Mol. Biol.*, 175:493–510, 1984.

Hearing and Shenk, J. Mol. Biol. 167:809–822, 1983.

Hearing et al., *J. Virol.*, 67:2555–2558, 1987.

Hedlund, Meech, Srikanth, Kraft, Miller, Schaack, Duke, "Adenovirus-mediated expression of Fas ligand induces apoptosis of human prostate cancer cells," *Cell Death & Differ.*, 6:175–182, 1999.

Hengartner and Horvitz, *Cell*, 76:65–676,1994.

Herrmann, Beham, Sarkiss, Chiao, Rands, Bruckheimer, Brisbay, McDonnell, *Exp. Cell Res.*, 237:101–109, 1997.

Hirao, Kong, Matsuoka, Wakeham, Ruland, Yoshida, Liu, Elledge, Mak, *Science*, 287:1824–1827, 2000.

Hogg, Bia, Onadim, and Cowell, "Molecular mechanisms of oncogenic mutations in tumors from patients with bilateral and unilateral retinoblastoma," *Proc. Nat'l Acad. Sci. U.S.A.* 90, 7351–7355, 1993.

Horowitz, Yandell, Park, Canning, Whyte, Buchkovich, Harlow, Weinberg, Dryja, "Point mutational inactivation of the retinoblastoma antioncogene," *Science* 243, 937–940, 1989.

Hsieh, Fredersdorf, Kouzarides, Martin, and Lu, "E2F1-induced apoptosis requires DNA binding but not transactivation and is inhibited by the retinoblastoma protein through direct interaction," *Genes & Dev.* 11, 1840–1852, 1997.

Hu, Dyson, Harlow, "The regions of the retinoblastoma protein needed for binding to adenovirus E1A or SV40 T antigen are common sites for mutations," *EMBO J.* 9,1147–1155, 1990.

Huang, Lee, Lee, "Identification of a cellular protein that competes with SV40 T antigen for binding to the retinoblastoma gene product," *Nature* 160–162, 1991.

Huang, Wang, Tseng, Lee, Lee, "Two distinct and frequently mutated regions of retinoblastoma protein are required for binding to SV40 T antigen," *EMBO J.* 9, 1815–1822, 1990.

Huang, Yee, Shew, Chen, Bookstein, Friedmann, Lee, Lee, "Suppression of the neoplastic phenotype by replacement of the retinoblastoma gene product in human cancer cells," *Science* 242, 1563–1566, 1988.

Hunt et al., *Proc. Nat'l Acad. Sci. USA*, 83:3786–3790, 1986.

Hunt, Deng, Liu, Wilson-Heiner, Swisher, Clayman, Hung, "Adenovirus-mediated overexpression of the transcription factor E2F-1 induces apoptosis in human breast and ovarian carcinoma cell lines and does not require p53," *Cancer Res.*, 57: 4722–4726, 1997.

Hunter, "Braking the cycle," *Cell* 75, 839–841, 1993.

Huyghe, Liu, Sutjipto, Sugarman, Horn, Shepard, Scandella, Shabram, "Purification of a type 5 recombinant adenovirus encoding human p53 by column chromatography," *Human Gene Therapy* 6:1403–1416, 1995.

Iliakis, *Sem. Oncology,* 24:602–615, 1997.

Inouye et al., *Nucleic Acids Res.,* 13:3101–3109, 1985.

Inouye, Torigoe, Sogahata, Kamiguchi, Takahashi, Sawada, Saijo, Taya, Ishii, and Sato, "70-kDa heat shock cognate protein interacts directly with the N-terminal region of the retinoblastoma gene product pRb. Identification of a novel region of pRb-mediating protein interaction," *J. Biol. Chem.* 270, 22571–22576, 1995.

Itoh et al., *J. Biol. Chem.* 268:10932–10937, 1993.

Jacobson, Weil, and Raff, "Programmed cell death in animal development," *Cell* 88, 347–354, 1997.

Janicke, Sprengart, Wati, Porter, *J. Biol. Chem.,* 273:9357–9360, 1998.

Janicke, Walker, Lin, and Porter, "Specific cleavage of the retinoblastoma protein by an ICE-like protease in apoptosis," *EMBO J.* 15, 6969–6978, 1996.

Joki et al., *Human Gene Ther.,* 6:1507–1513, 1995.

Kaelin, Krek, Sellers, DeCaprio, Ajchenbaum, Fuchs, Chittenden, Li, Farnham, Blanar, et al., "Expression cloning of a cDNA encoding a retinoblastoma-binding protein with E2F-like properties," *Cell* 70, 351–364, 1992.

Kaelin, Pallas, DeCaprio, Kaye, Livingston, "Identification of cellular proteins that can interact specifically with the T/E1A-binding region of the retinoblastoma gene product," *Cell* 64, 521–532 1991.

Kageyama, et al., *J. Biol. Chem.,* 262(5):2345–2351, 1987.

Kaneda et al., *Science,* 243:375–378, 1989.

Kaplitt et al., *Nat'l Genet.,* 8:148–153, 1994.

Kasibhatla, Brunner, Genestier, Echeverri, Mahboubi, Green, *Mol. Cell,* 1:543–551, 1998.

Kato et al, *J. Biol. Chem.,* 266:3361–3364, 1991.

Kerr et al., *Br. J. Cancer* 26:239–257, 1972.

Kessler et al., *Proc. Nat'l Acad. Sci. USA,* 93:14082–14087, 1996.

Kidd, "Proteolytic activities that mediate apoptosis," *Annu. Rev. Physiol.* 60, 533–573, 1998.

Kiefer, Brauer, Powers, Wu, Umansky, Tomei, Barr, *Nature,* 374:736–739, 1995.

Klein et al., *Nature,* 327:70–73, 1987.

Klement, Skinner, Kaytor, Yi, Hersch, Clark, Zoghbi, Orr, *Cell* 95:41–53, 1998.

Knudson, "Mutation and cancer: Statistical study of retinoblastoma," *Proc. Nat'l Acad. Sci.,* 68:820–23, 1971.

Koeberl et al., Proc. Nat'l Acad. Sci. USA, 94:1426–1431, 1997.

Korhonen et al., *Blood,* 86:1828–1835, 1995.

Kroemer, "The proto-oncogene Bcl-2 and its role in regulating apoptosis," *Nat'l Med.* 3, 614–620, 1997.

Lazebnik, Kaufmann, Desnoyers, Poirier, and Earnshaw, "Cleavage of poly(ADP-ribose) polymerase by a proteinase with properties like ICE," *Nature* 371, 346–347, 1994.

Le, Vallian, Mu, Hung, Chang, "Recombinant PML adenovirus supresses growth and tumorigenicity of human breast cancer cells by inducing G1 cell cycle arrest and apoptosis," *Oncogene,* 16: 1839–1849, 1998.

Lee, Dadgostar, Cheng, Shu, Cheng, *Proc. Natl. Acad. Sci. U.S.A.,* 96:9136–9141, 1999.

Lee, Hollingsworth, Qian, Chen, Hong, Lee, "The Rb Protein as a Cellular 'Corral' for Growth-Promoting Proteins," *Cold Spring Harbor Symp. Quanti. Biol.: Cell. Cycle.* 61, 211–217, 1991.

Lee, Shew, Hong, Sery, Donoso, Young, Bookstein, Lee, "The retinoblastoma susceptibility gene product is a nuclear phosphoprotein associated with DNA binding activity," *Nature* 329, 642–645, 1987b.

Lee, To, Shew, Bookstein, Scully, Lee, "Inactivation of the retinoblastoma susceptibility gene in human breast cancers," *Science* 241, 218–221, 1988.

Legrand-Poels, Bours, Piret, Pflaum, Epe, Rentier, Piette, *J. Biol. Chem.,* 270:6925–6934, 1995.

Leng, Connell-Crowley, Goodrich, and Harper, "S-phase entry upon ectopic expression of G1 cyclin-dependent kinases in the absence of retinoblastoma protein phosphorylation," *Curr. Biol.* 7, 709–712, 1997.

Letsou et al., *Proc. Nat'l Acad. Sci. USA* 88:810–814, 1991.

Levrero et al., *Gene,* 101: 195–202, 1991.

Lin, Gruenwald, Morla, Lee, Wang, "Retinoblastoma cancer Suppressor gene product is a substrate of the cell cycle regulator cdc2 kinase," *EMBO J.* 10, 857–864, 1991.

Liu, Zhang, Taylor, Roth, Goepfert, Clayman, "Growth suppression of human head and neck cancer cells by the introduction of a wild-type p53 gene via a recombinant adenovirus," *Cancer Res.,* 54: 3662–3667, 1994.

Liu, Zou, Slaughter, and Wang, "DFF, a heterodimeric protein that functions downstream of caspase-3 to trigger DNA fragmentation during apoptosis," *Cell* 89:175–184, 1997.

Lohmann, Brandt, Hopping, Passarge, and Horsthemke, "Distinct Rb1 gene mutations with low penetrance in hereditary retinoblastoma," *Hum. Genet.* 94, 349–354, 1994.

Luo, Budihardjo, Zou, Slaughter, and Wang, "Bid, a Bcl2 interacting protein, mediates cytochrome c release from mitochondria in response to activation of cell surface death receptors," *Cell* 94:481–490, 1998.

Macleod, Hu, Jacks, *EMBO J.,* 15:6178–6188, 1996.

Mann et al., *Cell,* 33:153–159, 1983.

McConkey, Goodrich, Bucana, and Klostergaard, "The human retinoblastoma gene product suppresses ceramide-induced apoptosis in human bladder tumor cells," *Oncogene* 13, 1693–1700, 1996.

McCown et al., *Brain Res.,* 713:99–107, 1996.

McDonnell, Nunez, Platt, Hockenberry, London, McKearn, and Korsmeyer, "Deregulated Bcl-2-immunoglobulin transgene expands a resting but responsive immunoglobulin M and D-expressing B-cell population," *Mol. Cell. Biol.* 10, 1901–1907, 1990.

Meng, Shih, Prabhu, George, El-Deiry, "Bypass of abnormal MDM2 inhibition of p53-dependent growth suppression," *Clin. Cancer Res.,* 4: 251–259, 1998.

Miyashita and Reed, *Cell,* 80:293–299, 1995.

Mizukami et al., *Virology,* 217:124–130, 1996.

Murnane, *Cancer Med. Rev.,* 14:17–29, 1995.

Nicolas and Rubenstein, In: *Vectors: A survey of molecular cloning vectors and their uses,* Rodriguez and Denhardt (eds.), Stoneham: Butterworth, pp. 493–513, 1988.

Nicolau and Sene, *Biochim. Biophys. Acta,* 721:185–190, 1982.

Nicolau et al., *Methods Enzymol.,* 149:157–176, 1987.

Olivierio, et al., *EMBO J.,* 6(7):1905–1912, 1987.

Ormerod, Sun, Snowden, Davies, Fearnhead, and Cohen, "Increased membrane permeability of apoptotic thymocytes: a flow cytometric study," *Cytometry* 14, 595–602, 1993.

Orth and Dixit, *J. Biol. Chem.,* 272:8841–8844, 1997.

Pape and Kim, *Mol. Cell. Biol.,* 974–982, 1989.

Park and Baichwal, "Systematic mutational analysis of the death domain of the tumor necrosis factor receptor 1-associated protein TRADD," *J.Biol.Chem.* 271, 9858–9862, 1996.

Park, Morris, Bremner, Keramaris, Padmanabhan, Rosenbaum, Shelanski, Geller, Greene, *J. Neurosci.,* 20:3104–3114, 2000.

Paskind et al., *Virology,* 67:242–248, 1975.

Perales et al., *Proc. Nat'l Acad. Sci.* 91:4086–4090, 1994.

Phillips, Ernst, Bates, Rice, Vousden, *Molecular Cell,* 4:771–781, 1999.

Ping et al., *Microcirculation,* 3:225–228, 1996.

Poli and Cortese, *Proc. Nat'l Acad. Sci. USA,* 86:8202–8206, 1989.

Pomerantz, Schreiber-Agus, Liegeois, Silverman, Alland, Chin, Potes, Chen, Orlow, Lee, Cordon-Cardo, DePinho, *Cell,* 92:713–723, 1998.

Potter et al., *Proc. Nat 'l Acad. Sci. USA,* 81:7161–7165, 1984.

Prowse and Baumann, *Mol Cell Biol,* 8(1):42–51, 1988.

Quignon, DeBels, Koken, Feunteun, Ameisen, de The, "PML induces a novel caspase-independent death process," *Nat. Genet.,* 20:259–265, 1998.

Radler et al., *Science,* 275:810–814, 1997.

Rb Protein Inhibits p84N5-induced Apoptosis, 10:3261, October 1999.

Renan, *Radiother. Oncol.,* 19:197–218, 1990.

Ridgeway, In: *Vectors: A survey of molecular cloning vectors and their uses,* Rodriguez R L, Denhardt D T, ed., Stoneham:Butterworth, pp. 467–492, 1988.

Riley, Liu, and Lee, "Mutations of N-terminal regions render the retinoblastoma protein insufficient for functions in development and tumor suppression," *Mol. Cell. Biol.* 17, 7342–7352, 1997.

Rippe et al., *Mol. Cell Biol.,* 10:689–695, 1990.

Ron et al., *Mol. Cell. Biol.,* 2887–2895, 1991.

Roth, "Restoration of tumor suppressor gene expression for cancer," *Forum* 8:368–376, 1998.

Rotman, G. and Shiloh, Y. (1997) *Cancer Surv.* 29, 285–304

Roux et al., *Proc. Nat'l Acad. Sci. USA,* 86:9079–9083, 1989.

Rustgi, Dyson, Bernards, "Amino-terminal domains of c-myc. and N-myc proteins mediate binding to the retinoblastoma gene product," *Nature* 352,541–544, 1991.

Samulski et al., *J. Virol.,* 61(10):3096–3101, 1987.

Sanchez, Xu, Juo, Kakizaka, Blenis, Yuan, *Neuron,* 22:623–633, 1999.

Saudou, Finkbeiner, Devys, Greenberg, "Huntington acts in the neucleus to induce apoptosis but death does not correlate with the formation of internuclear inclusions," *Cell,* 95:55–66, 1998.

Sheikh and Fornace, Jr. *J. Cell Physiol.* 182, 171–181, 2000.

Shelton and Wasserman, *Cell* 72, 515–525, 1993.

Shimizu, Narita, Tsujimoto, *Nature,* 399:483–87, 1999.

Singh and Lavin, *Mol. Cell. Biol.,* 10:5279–5285, 1990.

Sionov and Haupt, *Oncogene* 18:6145–6157, 1999.

Soengas, Alarcon, Yoshida, Giaccia, Hakem, Mak, Lowe, *Science,* 284:156–159, 1999.

Song, Kuang, Dixit, Vincenz, *EMBO J.,* 18:167–178, 1999.

Speigelman, et al., *J. Biol. Chem.,* 264(3), 1811–1815, 1989.

Srinivasula, Ahmad, Fernandes-Alnemri, Alnemri, *Mol. Cell,* 1:949–957, 1998.

Steller, *Science* 267:1445–1449, 1995.

Sterner, Dew-Knight, Musahl, Kornbluth, and Horowitz, "Negative regulation of DNA replication by the retinoblastoma protein is mediated by its association with MCM7,"*Mol. Cell. Biol.* 18, 2748–2757, 1998.

Sterner, Tao, Kennett, Kim, and Horowitz, "The amino terminus of the retinoblastoma (Rb) protein associates with a cyclin-dependent kinase-like kinase via Rb amino acids required for growth suppression," *Cell Growth Differ.* 7, 53–64, 1996.

Sumegi, Uzvolgyi, Klein, "Expression of the Rb gene under the control of MuLV-LTR suppresses tumorigenicity of WERI-Rb-27 retinoblastoma cells in immunodefective mice," *Cell Growth Differ.* 1:247–250, 1990.

Takahashi, Hashimoto, Hong-Ji, Hu, Matsui, Miki, Bigo-Marshall, Aaronson, Benedict, "The retinoblastoma gene functions as a growth and tumor suppressor in human bladder carcinoma cells," *Proc. Nat'l Acad. Sci. USA.* 88, 5257–5261, 1991.

Talanian, Quinlan, Trautz, Hackett, Mankovich, Banach, Ghayur, Brady, and Wong, "Substrate specificities of caspase family proteases," *J. Biol. Chem.* 272, 9677–9682,1997.

Tartaglia, Ayres, Wong, and Goeddel, "A novel domain within the 55 kd TNF receptor signals cell death," *Cell* 74, 845–853, 1993.

Temin, In: *Gene Transfer,* Kucherlapati (ed.), New York: Plenum Press, pp. 149–188, 1986.

Terry and White, *Clin. Immunol. News,* 16:46–50, 1996.

Terry White, Meistrich, and Calkins, *Cytometry,* 12:234–241, 1991.

Thompson, *Science* 267:1456–1462, 1995.

Thornberry, Rano, Peterson, Rasper, Timkey, Garcia-Calvo, Houtzager, Nordstrom, Roy, Vaillancourt, Chapman, Nicholson, *J. Biol. Chem.,* 272:17907–17911, 1997.

Tibbetts *Cell,* 12:243–249, 1977.

Toguchida, Ishizaki, Sasaki, Ikenaga, Sugimoto, Kotoura, Yamamuro, "Chromosomal-reorganization for the expression of recessive mutation of retinoblastoma susceptibility gene in the development of osteosarcoma," *Cancer Res.* 48,3939–943, 1988.

Tsai, Hu, Macleod, Crowley, Yamasaki, Jacks, *Molecular Cell,* 2:293–304, 1998.

Tsukahara, Kannagi, Ohashi, Kato, Arai, Nunez, Iwanaga, Yamamoto, Ohtani, Nakamura, Fujii, *J. Virol,.* 73:7981–7987, 1999.

Tur-Kaspa et al., *Mol. Cell Biol.,* 6:716–718, 1986.

Uhlik, Good, Xiao, Harhaj, Zandi, Karin, Sun, *J. Biol. Chem.,* 273:21132–21136, 1998.

Vaishnaw, Orlinick, Chu, Krammer, Chao, and Elkon, "The molecular basis for apoptotic defects in patients with CD95 (Fas/Apo-1) mutations," *J.Clin.Invest.* 103, 355–363, 1999.

Vaux, Haecker, and Strasser, "An evolutionary perspective on apoptosis," *Cell* 76, 777–779, 1994.

Wadgaonkar, Phelps, Haque, Williams, Silverman, Collins, *J. Biol. Chem.,* 274:1879–1882, 1999.

Wagner et al., *Proc. Nat'l Acad. Sci.* 87(9):3410–3414, 1990.

Walther and Stein, *J. Mol. Med,* 74:379–392, 1996.

Wang, *Curr. Opin. Genet. Dev.,* 7:39–45, 1997.

Wang, Guo, Wills, and Walsh, "Rb functions to inhibit apoptosis during myocyte differentiation," *Cancer Res.,* 57:351–354, 1997.

Wang, Mayo, Baldwin, Jr., *Science,* 274:784–787 27,1996.

Wang, Qian, Chung, Lee, Lee, "Expression of the human retinoblastoma gene product pp110Rb in insect cells using the baculovirus system," *Cell Growth Diff.* 1, 429–437, 1990.

Wang, Zelenski, Yang, Sakai, Brown, Goldstein, "Cleavage of sterol regulatory element binding proteins (SREBPs) by CPP32 during apoptosis," *EMBO J.,* 15:1012–1020, 1996.

Watt et al., *Proc. Nat'l Acad. Sci.,* 83(2): 3166–3170, 1986.
Webster and Perkins, *Mol. Cell. Biol.,* 19:3485–3495, 1999.
Weintraub, Prater, and Dean, "Retinoblastoma protein switches the E2F site from positive to negative element," *Nature* 358, 259–261, 1992.
White, Meistrich, Pollack, Terry, *Cytometry,* 2000.
White, Terry, Meistrich, Calkins, *Cytometry,* 11:314–317, 1990b.
White, Terry, Meistrich, *Cell & Tissue Kinetics* 23:561–573, 1990a.
Whyte, Buchkovich, Horowitz, Friend, Raybuck, Weinbierg, Harlow, "Association between an oncogene and an anti-oncogene: the adenovirus E1A proteins bind to the retinoblastoma gene product," *Nature* 334, 124–129, 1988.
Wiegmann et al., *Cell* 78:1005–1015, 1994.
Wigler, Sweet, Sim, Wold, Pellicer, Lacy, Maniatis, Silverstein, and Axel, "Transformation of mammalian cells with genes from procaryotes and eucaryotes," *Cell,* 16:777–785, 1979.
Wilson, et al., *Mol. Cell. Biol.,* 6181–6191, 1990.
Wolf and Green, *J.Biol.Chem.* 274:20049–20052, 1999.
Wong et al., *Gene,* 10:87–94, 1980.
Wu and Wu, *Adv. Drug Delivery Rev.,* 12:159–167, 1993.
Wu and Wu, *Biochem.,* 27:887–892, 1988.
Wu and Wu, *J. Biol. Chem.,* 262:4429–4432, 1987.
Wyllie, *Nature* 284:555–556, 1980.
Xiao et al., *J. Virol.,* 70:8098–8108, 1996.
Xu, Sneige, Liu, Nandagiri, Lee, Lukmanji, Hortobagyi, Lippman, Dhingra, Lotan, "Progressive decrease in nuclear retinoic acid receptor beta messenger RNA level during breast carcinogenesis," *Cancer Research* 57, 4992–4996, 1997.
Yang et al., *Proc. Nat'l Acad. Sci USA,* 87:9568–9572, 1990.
Yin, Hung, Goodrich, *Cancer Gene Ther.,* 2000.
Yin, Knudson, Korsmeyer, Van Dyke, *Nature* 385:637–640, 1997.
Yin, Knudson, Korsmeyer, Van Dyke, *Nature,* 385:637–640, 1997.
Yokota, Akiyama, Fung, Benedict, Namba, Hanaoka, Wada, Terasaki, Shimosato, Sugimura, Terada, "Altered expression of the retinoblastoma (Rb) gene in small cell carcinoma of the lung," *Oncogene* 3, 471–475, 1988.
Yu and Little, *Cancer Res.,* 58:4277–4281, 1998.
Yuan, *Curr. Opin. Cell Biol.* 9:247–251, 1997.
Yuan, Shaham, Ledoux, Ellis, Horvitz, *Cell,* 75:641–652, 1993.
Zacksenhaus, Jiang, Chung, Marth, Phillips, and Gallie, "pRb controls proliferation, differentiation, and death of skeletal muscle cells and other lineages during embryogenesis," *Genes & Dev.* 10, 3051–3064, 1996.
Zechner, et al., *Mol. Cell. Biol.,* 2394–2401, 1988.
Zhang, Fang, Branch, Mazur, French, Roth, "Generation and identification of recombinant adenovirus by liposome-mediated transfection and PCR analysis," *Biotechniques,* 15: 868–872, 1993.
Zhou, Chaturvedi, Spring, Scott, Johanson, Mishra, Mattern, Winkler, Khanna, *J.Biol. Chem.,* 275, 10342–10348, 2000.
Zimmerman, "Retinoblastoma and retinocytoma," In W. H. Spencer (ed.), Ophthalmic Pathology: an Atlas and Textbook, Vol. II, Philadelphia: W. B. Saunders Co., pp. 1292–1351, 1985.
Ziv, Bar-Shira, Pecker, Russell, Jorgensen, Tsarfati, Shiloh, *Oncogene,* 15:159–167, 1997.
Zou, Henzel, Liu, Lutschg, Wang, *Cell,* 90:405–413, 1997.

What is claimed is:

1. A viral composition comprising a recombinant viral vector comprising a DNA segment encoding the polypeptide of SEQ ID NO:2 or a DNA death domain-containing fragment thereof.

2. The composition of claim 1, wherein said recombinant viral vector is an adenoviral, adeno-associated viral, or retroviral vector.

3. The composition of claim 1, wherein said polypeptide is fused to a second protein.

4. The composition of claim 1, wherein said DNA segment encodes SEQ ID NO:2.

5. A method of treating cancer in a mammalian subject, comprising directly contacting a cancer cell in said subject with a recombinant vector comprising a DNA segment encoding SEQ ID NO:2, or a DNA death domain-containing fragment thereof, wherein said DNA segment is operably linked to a promoter that is active in said cancer cell, and wherein said cancer cell does not express wild-type Rb.

6. The method of claim 5, wherein said DNA segment encodes SEQ ID NO:2.

7. The method of claim 5, wherein said recombinant vector is a viral vector.

8. The method of claim 7, wherein said viral vector is an adenoviral, adeno-associated viral, or retroviral vector.

9. The method of claim 8, wherein said viral vector is an adenovirus.

10. The method of claim 9, wherein said adenovirus is administered at a dose of about $10^{10}$ to about $10^{12}$ pfu.

11. The method of claim 5, wherein treating cancer is by inducing apoptosis in a cancer cell in said subject, inhibiting cell division in a cancer cell in said subject, inhibiting metastatic potential in a cancer cell in said subject, reducing tumor burden in said subject, increasing sensitivity to chemotherapy or radiotherapy in a cancer cell in said subject, killing a cancer cell in said subject, inhibiting the growth of a cancer cell in said subject, or inducing tumor regression in a cancer cell in said subject.

12. The method of claim 5, wherein said subject is human.

13. The method of claim 5, further comprising treating the subject with a second agent, wherein the second agent is a chemotherapeutic agent, or a radiotherapeutic agent.

14. The method of claim 13, wherein said second agent is administered at a different time than the recombinant vector.

15. The method of claim 5, wherein directly contacting said cancer cells is by intravenous, intraperitoneal, intradermal, intratumoral, intramuscular, oral, dermal, nasal, buccal, rectal, vaginal, inhalation, or topical administration.

16. A method of inhibiting growth of a cancer cell that fails to express wild-type Rb, comprising directly contacting said cancer cell with a recombinant vector comprising a DNA segment encoding SEQ ID NO:2, or a death domain-containing fragment thereof, wherein said DNA segment is operably linked to a promoter that is active in said cancer cell.

17. The method of claim 16, wherein said inhibiting a cancer cell is by inducing apoptosis in said cancer cell, inhibiting cell division in said cancer cell, inhibiting metastatic potential in said cancer cell, increasing sensitivity to chemotherapy or radiotherapy in said cancer cell, or killing said cancer cell.

* * * * *

SEQUENCE LISTING

```
<160> NUMBER OF SEQ ID NOS: 17

<210> SEQ ID NO 1
<211> LENGTH: 2092
<212> TYPE: DNA
<213> ORGANISM: Human

<400> SEQUENCE: 1
ggccttcgtc gaagatgtct ccgacgccgc cgctcttcag tttgcccgaa gcgcggacgc      60
ggtttacgaa gtctaccaga gaggccttga acaacaaaaa catcaagcca ttgttaagta     120
ccttcagcca ggtacctggc agtgaaaatg aaaaaaaatg taccettgac caagctttca     180 gaggtattct agaagaagaa attataaatc attcatcatg tgaaaacgtt ttagctatta     240
tttctcttgc tattggggga gtaactgaag gtatttgtac cgcatctaca ccttttgtat     300
tgttgggaga tgttttggat tgtcttcctt tggatcagtg tgacacaata ttcacttttg     360
tcgaaaaaaa tgttgctact tggaaatcaa ataccttcta tgctgctggg aaaaattact     420
tactacgtat gtgcaatgat ctcctaagaa gattgtctaa atcccagaat acagtcttct     480
gtggacggat tcagctcttt ttggccaggc ttttccctct gtctgagaaa tcaggtctta     540
acttgcagag tcagtttaat ctggaaaatg tcactgtttt caatacaaat gagcaggaaa     600
gcaccctggg tcagaagcac actgaagata gagaagaagg aatggatgta gaagaaggcg     660
aaatgggaga tgaggaagct ccaacaacgt gctctattcc aattgattac aacctgtatc     720
gaaaattctg gtcacttcag gattacttca ggaaccctgt gcaatgctat gagaagattt     780
```

-continued

```
catggaaaac ttttctcaag tattctgaag aagttttagc tgttttttaag agttataaat    840
tagatgatac tcaggcctca agaaaaaaga tggaagaatt gaaaacagga ggagaacatg    900
tatattttgc aaaattttta acaagtgaaa agctgatgga tttacaactg agtgacagta    960
actttcgtcg acacatcctg ttgcagtatc tcattttatt ccaatatctc aaggggcagg   1020
tcaaattcaa aagttcaaac tatgttttaa ctgatgagca atcactttgg attgaagata   1080
ctacaaaatc agtttatcaa ctactatctg aaaaccccccc cgatggagaa agattttcaa   1140
agatggtaga gcatatatta aacactgaag aaaactggaa ctcgtggaaa aatgaaggtt   1200
gcccaagttt tgtgaaagaa agaacatcag ataccaaacc tacgagaata attcggaaga   1260
gaacagcacc cgaggacttc ctagggaaag gacccaccaa aaaaattctg acgggaaatg   1320
aggagttaac aaggctttgg aatctttgcc ctgataatat ggaagcctgt aaatcagaga   1380
caagggaaca catgcccact ttggaggaat tctttgaaga agccattgaa caggcagacc   1440
ctgaaaatat ggcggaaaat gaatataagg ctatgaacaa ttcaaattat ggttggagag   1500
ccctgaaaact attagcacgg agaagccctc acttcttcca gccaaccaac cagcagttta   1560
aaagtttaca agaatatctt gaaaatatgg taataaagct agccaaggaa ttaccgcctc   1620
cttctgaaga aataaaaaca ggtgaggatg aagatgagga agataatgat gctctactga   1680
aggaaaatga aagtcctgat gttcggcgag acaaacctgt aacaggagaa caaatagagg   1740
tatttgccaa caagctgggt gaacaatgga agattctggc tccctacttg gaaatgaaag   1800
actcagaaat taggcagatt gagtgtgaca gtgaagacat gaagatgaga gctaagcagc   1860
tcctggttgc ctggcaagat caagagggag ttcatgcaac acctgagaat ctgattaatg   1920
cactgaataa gtctggatta agtgaccttg cagaaagtct aactaatgac aatgagacaa   1980
atagttagct tctttttttt ttcttttttat taaaactgtg atagattttg ttaccaagca   2040
gcatttgata agaggtccac tggttttggt aaacaataaa cattttata ac            2092
```

<210> SEQ ID NO 2
<211> LENGTH: 657
<212> TYPE: PRT
<213> ORGANISM: Human

<400> SEQUENCE: 2

```
Met Ser Pro Thr Pro Pro Leu Phe Ser Leu Pro Glu Ala Arg Thr Arg
  1               5                  10                  15

Phe Thr Lys Ser Thr Arg Glu Ala Leu Asn Asn Lys Asn Ile Lys Pro
             20                  25                  30

Leu Leu Ser Thr Phe Ser Gln Val Pro Gly Ser Glu Asn Glu Lys Lys
         35                  40                  45

Cys Thr Leu Asp Gln Ala Phe Arg Gly Ile Leu Glu Glu Glu Ile Ile
     50                  55                  60

Asn His Ser Ser Cys Glu Asn Val Leu Ala Ile Ile Ser Leu Ala Ile
 65                  70                  75                  80

Gly Gly Val Thr Glu Gly Ile Cys Thr Ala Ser Thr Pro Phe Val Leu
                 85                  90                  95

Leu Gly Asp Val Leu Asp Cys Leu Pro Leu Asp Gln Cys Asp Thr Ile
                100                 105                 110

Phe Thr Phe Val Glu Lys Asn Val Ala Thr Trp Lys Ser Asn Thr Phe
            115                 120                 125

Tyr Ala Ala Gly Lys Asn Tyr Leu Leu Arg Met Cys Asn Asp Leu Leu
        130                 135                 140
```

```
Arg Arg Leu Ser Lys Ser Gln Asn Thr Val Phe Cys Gly Arg Ile Gln
145                 150                 155                 160

Leu Phe Leu Ala Arg Leu Phe Pro Leu Ser Glu Lys Ser Gly Leu Asn
                165                 170                 175

Leu Gln Ser Gln Phe Asn Leu Glu Asn Val Thr Val Phe Asn Thr Asn
            180                 185                 190

Glu Gln Glu Ser Thr Leu Gly Gln Lys His Thr Glu Asp Arg Glu Glu
            195                 200                 205

Gly Met Asp Val Glu Gly Glu Met Gly Asp Glu Glu Ala Pro Thr
210                 215                 220

Thr Cys Ser Ile Pro Ile Asp Tyr Asn Leu Tyr Arg Lys Phe Trp Ser
225                 230                 235                 240

Leu Gln Asp Tyr Phe Arg Asn Pro Val Gln Cys Tyr Glu Lys Ile Ser
                245                 250                 255

Trp Lys Thr Phe Leu Lys Tyr Ser Glu Glu Val Leu Ala Val Phe Lys
            260                 265                 270

Ser Tyr Lys Leu Asp Asp Thr Gln Ala Ser Arg Lys Lys Met Glu Glu
        275                 280                 285

Leu Lys Thr Gly Gly Glu His Val Tyr Phe Ala Lys Phe Leu Thr Ser
290                 295                 300

Glu Lys Leu Met Asp Leu Gln Leu Ser Asp Ser Asn Phe Arg Arg His
305                 310                 315                 320

Ile Leu Leu Gln Tyr Leu Ile Leu Phe Gln Tyr Leu Lys Gly Gln Val
                325                 330                 335

Lys Phe Lys Ser Ser Asn Tyr Val Leu Thr Asp Glu Gln Ser Leu Trp
            340                 345                 350

Ile Glu Asp Thr Thr Lys Ser Val Tyr Gln Leu Leu Ser Glu Asn Pro
            355                 360                 365

Pro Asp Gly Glu Arg Phe Ser Lys Met Val Glu His Ile Leu Asn Thr
        370                 375                 380

Glu Glu Asn Trp Asn Ser Trp Lys Asn Glu Gly Cys Pro Ser Phe Val
385                 390                 395                 400

Lys Glu Arg Thr Ser Asp Thr Lys Pro Thr Arg Ile Ile Arg Lys Arg
                405                 410                 415

Thr Ala Pro Glu Asp Phe Leu Gly Lys Gly Pro Thr Lys Lys Ile Leu
            420                 425                 430

Thr Gly Asn Glu Glu Leu Thr Arg Leu Trp Asn Leu Cys Pro Asp Asn
        435                 440                 445

Met Glu Ala Cys Lys Ser Glu Thr Arg Glu His Met Pro Thr Leu Glu
450                 455                 460

Glu Phe Glu Glu Ala Ile Glu Gln Ala Asp Pro Glu Asn Met Ala
465                 470                 475                 480

Glu Asn Glu Tyr Lys Ala Met Asn Asn Ser Asn Tyr Gly Trp Arg Ala
                485                 490                 495

Leu Lys Leu Leu Ala Arg Arg Ser Pro His Phe Phe Gln Pro Thr Asn
            500                 505                 510

Gln Gln Phe Lys Ser Leu Gln Glu Tyr Leu Glu Asn Met Val Ile Lys
            515                 520                 525

Leu Ala Lys Glu Leu Pro Pro Pro Ser Glu Glu Ile Lys Thr Gly Glu
        530                 535                 540

Asp Glu Asp Glu Glu Asp Asn Asp Ala Leu Leu Lys Glu Asn Glu Ser
545                 550                 555                 560
```

```
Pro Asp Val Arg Arg Asp Lys Pro Val Thr Gly Glu Gln Ile Glu Val
            565                 570                 575

Phe Ala Asn Lys Leu Gly Glu Gln Trp Lys Ile Leu Ala Pro Tyr Leu
            580                 585                 590

Glu Met Lys Asp Ser Glu Ile Arg Gln Ile Glu Cys Asp Ser Glu Asp
            595                 600                 605

Met Lys Met Arg Ala Lys Gln Leu Leu Val Ala Trp Gln Asp Gln Glu
        610                 615                 620

Gly Val His Ala Thr Pro Glu Asn Leu Ile Asn Ala Leu Asn Lys Ser
625                 630                 635                 640

Gly Leu Ser Asp Leu Ala Glu Ser Leu Thr Asn Asp Asn Glu Thr Asn
                645                 650                 655

Ser

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (12)
<223> OTHER INFORMATION: S = G or C
<220> FEATURE:
<221> NAME/KEY: modified_base
<222> LOCATION: (22)
<223> OTHER INFORMATION: S = G or C
<220> FEATURE:
<221> NAME/KEY: modified_base
<222> LOCATION: (13)
<223> OTHER INFORMATION: R = A or G
<220> FEATURE:
<221> NAME/KEY: modified_base
<222> LOCATION: (21)
<223> OTHER INFORMATION: R = A or G

<400> SEQUENCE: 3
cttgatcttg csrggcaacc rsgagctgct tagc                              34

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
agggagttca tgcaacacct g                                            21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
tcatgtcttc actgtcacac t                                            21

<210> SEQ ID NO 6
<211> LENGTH: 37
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 6

Gln Ala Phe Gln Leu Leu Arg Arg Phe Val Gln Ala Glu Gly Ala Thr
 1               5                  10                  15

Leu Gln Arg Leu Val Glu Ala Ile Glu Glu Asn Glu Leu Thr Ser Leu
             20                  25                  30

Ala Glu Asp Leu Leu
             35

<210> SEQ ID NO 7
<211> LENGTH: 37
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Gln Val Gln Leu Leu Arg Asn Trp His Gln Leu His Gly Lys Lys Ala
 1               5                  10                  15

Tyr Asp Thr Leu Ile Lys Asp Leu Lys Lys Ala Asn Leu Cys Thr Leu
             20                  25                  30

Ala Glu Lys Ile Gln
             35

<210> SEQ ID NO 8
<211> LENGTH: 42
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Arg Ala Lys Gln Leu Leu Val Ala Trp Gln Asp Gln Glu Gly Val His
 1               5                  10                  15

Ala Thr Pro Glu Asn Leu Ile Asn Ala Ile Asn Ala Ile Asn Lys Ser
             20                  25                  30

Gly Leu Ser Asp Leu Ala Glu Ser Leu Thr
             35                  40

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Arg Lys Arg Thr Ala Pro Glu Asp Phe Leu Gly Lys Gly Pro Thr Lys
 1               5                  10                  15

Lys

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
```

-continued

Peptide

<400> SEQUENCE: 10

Arg Tyr Ala Gln Glu Met Glu Gly Glu Glu Ala
 1               5                  10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 11

Leu Ala Pro Pro Leu Glu Arg Leu Thr Leu
 1               5                  10

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 12
aattattctc gtaggtttgg tatctgatg                                    29

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 13
attctgacgg gaaatgagga gttaacaagg                                   30

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 14
catctcctgg gcataacgaa ttattctcgt aggtttggta tc                     42

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 15
gaaggcgaag aagaagccat tctgacggga aatgaggagt ta                     42

<210> SEQ ID NO 16
<211> LENGTH: 39
<212> TYPE: DNA
<213> ORGANISM: Artificial Sequence
<220> FEATURE:

-continued

```
<223> OTHER INFORMATION: Description of Artificial Sequence:  Synthetic
      Primer

<400> SEQUENCE: 16
gaacttcttc gtcataatta ttctcgtagg tttggtatc                              39

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 17
ggcacgctca cgatcattct gacgggaaat gaggag                                 36
```